(12) United States Patent
Venditto et al.

(10) Patent No.: US 11,660,269 B2
(45) Date of Patent: May 30, 2023

(54) LIPOSOMAL COMPOUNDS AND METHODS OF USE THEREOF

(71) Applicant: University of Kentucky Research Foundation, Lexington, KY (US)

(72) Inventors: Vincent J. Venditto, Lexington, KY (US); Ahmed Abdel-Latif, Lexington, KY (US); Ahmed Al-Darraji, Lexington, KY (US); Dave Feola, Lexington, KY (US); John C. Gensel, Versailles, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 16/834,764

(22) Filed: Mar. 30, 2020

(65) Prior Publication Data

US 2020/0315966 A1 Oct. 8, 2020

Related U.S. Application Data

(60) Provisional application No. 62/826,821, filed on Mar. 29, 2019.

(51) Int. Cl.
| | | |
|---|---|---|
| *A61K 9/127* | (2006.01) | |
| *A61P 37/06* | (2006.01) | |
| *A61K 31/7048* | (2006.01) | |
| *A61P 9/00* | (2006.01) | |

(52) U.S. Cl.
CPC .......... *A61K 9/127* (2013.01); *A61K 31/7048* (2013.01); *A61P 9/00* (2018.01); *A61P 37/06* (2018.01)

(58) Field of Classification Search
CPC ..... A61K 9/127; A61K 31/7048; A61P 37/06; A61P 9/00
See application file for complete search history.

(56) References Cited

U.S. PATENT DOCUMENTS

| | | | | |
|---|---|---|---|---|
| 5,593,688 A | * | 1/1997 | Baldeschwieler ..... | A61K 9/127 424/1.21 |
| 6,281,199 B1 | * | 8/2001 | Gupta ..................... | A61P 9/10 514/29 |
| 2004/0266734 A1 | * | 12/2004 | Danenberg .............. | A61P 43/00 514/89 |

OTHER PUBLICATIONS

European Heart Journal (2004) 25, 1197-1207 (Year: 2004).*
Al-Darraji, A., D. Haydar, L. Chelvarajan, H. Tripathi, B. Levitan, E. Gao, V. J. Venditto, J. C. Gensel, D. J. Feola and A. Abdel-Latif (2018). "Azithromycin therapy reduces cardiac inflammation and mitigates adverse cardiac remodeling after myocardial infarction: Potential therapeutic targets in ischemic heart disease." PLoS One 13(7): e0200474.
Amantea, D., M. Certo, F. Petrelli, C. Tassorelli, G. Micieli, M. T. Corasaniti, P. Puccetti, F. Fallarino and G. Bagetta (2016). "Azithromycin protects mice against ischemic stroke injury by promoting macrophage transition towards M2 phenotype." Exp Neurol 275 Pt 1: 116-125.
Aoki, Y. and P. N. Kao (1999). "Erythromycin inhibits transcriptional activation of NF-kappaB, but not NFAT, through calcineurin-independent signaling in T cells." Antimicrob Agents Chemother 43(11): 2678-2684.
Aoshiba, K., A. Nagai and K. Konno (1995). "Erythromycin shortens neutrophil survival by accelerating apoptosis." Antimicrob Agents Chemother 39(4): 872-877.
Caride, V. J., J. Twickler and B. L. Zaret (1984). "Liposome kinetics in infarcted canine myocardium." J Cardiovasc Pharmacol 6(6): 996-1005.
Cheraghi, M., B. Negahdari, H. Daraee and A. Eatemadi (2017). "Heart targeted nanoliposomal/nanoparticles drug delivery: An updated review." Biomed Pharmacother 86: 316-323.
Cigana, C., B. M. Assael and P. Melotti (2007). "Azithromycin selectively reduces tumor necrosis factor alpha levels in cystic fibrosis airway epithelial cells." Antimicrob Agents Chemother51(3): 975-981.
Cory, T. J., S. E. Birket, B. S. Murphy, D. Hayes, Jr., M. I. Anstead, J. F. Kanga, R. J. Kuhn, H. M. Bush and D. J. Feola (2014). "Impact of azithromycin treatment on macrophage gene expression in subjects with cystic fibrosis." J Cyst Fibros 13(2): 164-171.
Dasa, S. S. K., R. Suzuki, M. Gutknecht, L. T. Brinton, Y. Tian, E. Michaelsson, L. Lindfors, A. L. Klibanov, B. A. French and K. A. Kelly (2015). "Development of target-specific liposomes for delivering small molecule drugs after reperfused myocardial infarction." J Control Release 220(Pt A): 556-567.
Desaki, M., H. Takizawa, T. Ohtoshi, T. Kasama, K. Kobayashi, T. Sunazuka, S. Omura, K. Yamamoto and K. Ito (2000). "Erythromycin suppresses nuclear factor-kappaB and activator protein-1 activation in human bronchial epithelial cells." Biochem Biophys Res Commun 267(1): 124-128.
Feola, D. J., B. A. Garvy, T. J. Cory, S. E. Birket, H. Hoy, D. Hayes, Jr. and B. S. Murphy (2010). "Azithromycin alters macrophage phenotype and pulmonary compartmentalization during lung infection with Pseudomonas." Antimicrob Agents Chemother 54(6): 2437-2447.
Foulds, G., R. M. Shepard and R. B. Johnson (1990). "The pharmacokinetics of azithromycin in human serum and tissues." J Antimicrob Chemother 25 Suppl A: 73-82.
Gensel, J. C., T. J. Kopper, B. Zhang, M. B. Orr and W. M. Bailey (2017). "Predictive screening of M1 and M2 macrophages reveals the immunomodulatory effectiveness of post spinal cord injury azithromycin treatment." Sci Rep 7: 40144.
Gensel, J. C. and B. Zhang (2015). "Macrophage activation and its role in repair and pathology after spinal cord injury." Brain Res 1619: 1-11.
Hodge, S., G. Hodge, S. Brozyna, H. Jersmann, M. Holmes and P. N. Reynolds (2006). "Azithromycin increases phagocytosis of apoptotic bronchial epithelial cells by alveolar macrophages."Eur Respir J 28(3): 486-495.

(Continued)

*Primary Examiner* — Snigdha Maewall
(74) *Attorney, Agent, or Firm* — Stites & Harbison PLLC; Mandy Wilson Decker

(57) ABSTRACT

A composition and method for treating a subject following myocardial infarction are provided. The composition includes a non-PEGylated liposome. The method includes administering a non-PEGylated liposome to a subject in need thereof following myocardial infarction.

10 Claims, 25 Drawing Sheets

(56) References Cited

OTHER PUBLICATIONS

Imamura, Y., K. Yanagihara, Y. Mizuta, M. Seki, H. Ohno, Y. Higashiyama, Y. Miyazaki, K. Tsukamoto, Y. Hirakata, K. Tomono, J. Kadota and S. Kohno (2004). "Azithromycin inhibits MUC5AC production induced by the Pseudomonas aeruginosa autoinducer N-(3-Oxododecanoyl) homoserine lactone in NCI-H292 Cells." Antimicrob Agents Chemother 48(9): 3457-3461.

Inamura, K., N. Ohta, S. Fukase, N. Kasajima and M. Aoyagi (2000). "The effects of erythromycin on human peripheral neutrophil apoptosis." Rhinology 38(3): 124-129.

Ivetic Tkalcevic, V., B. Bosnjak, B. Hrvacic, M. Bosnar, N. Marjanovic, Z. Ferencic, K. Situm, O. Culic, M. J. Parnham and V. Erakovic (2006). "Anti-inflammatory activity of azithromycin attenuates the effects of lipopolysaccharide administration in mice." Eur J Pharmacol 539(1-2): 131-138.

Kaneko, Y., K. Yanagihara, M. Seki, M. Kuroki, Y. Miyazaki, Y. Hirakata, H. Mukae, K. Tomono, J. Kadota and S. Kohno (2003). "Clarithromycin inhibits overproduction of muc5ac core protein in murine model of diffuse panbronchiolitis." Am J Physiol Lung Cell Mol Physiol 285(4): L847-853.

Kanoh, S. and B. K. Rubin (2010). "Mechanisms of action and clinical application of macrolides as immunomodulatory medications." Clin Microbiol Rev 23(3): 590-615.

Kelly, C., C. Jefferies and S. A. Cryan (2011). "Targeted liposomal drug delivery to monocytes and macrophages." J Drug Deliv 2011: 727241.

Koch, C. C., D. J. Esteban, A. C. Chin, M. E. Olson, R. R. Read, H. Ceri, D. W. Morck and A. G. Buret (2000). "Apoptosis, oxidative metabolism and interleukin-8 production in human neutrophils exposed to azithromycin: effects of *Streptococcus pneumoniae*." J Antimicrob Chemother 46(1): 19-26.

Levchenko, T. S., W. C. Hartner and V. P. Torchilin (2012). "Liposomes in diagnosis and treatment of cardiovascular disorders." Methodist Debakey Cardiovasc J 8(1): 36-41.

Mueller, T. M., M. L. Marcus, H. E. Mayer, J. K. Williams and K. Hermsmeyer (1981). "Liposome concentration in canine ischemic myocardium and depolarized myocardial cells." Circ Res49(2): 405-415.

Murphy, B. S., V. Sundareshan, T. J. Cory, D. Hayes, Jr., M. I. Anstead and D. J. Feola (2008). "Azithromycin alters macrophage phenotype." J Antimicrob Chemother 61(3): 554-560.

Oh, Y. K., D. E. Nix and R. M. Straubinger (1995). "Formulation and efficacy of liposome-encapsulated antibiotics for therapy of intracellular *Mycobacterium avium* infection." Antimicrob Agents Chemother 39(9): 2104-2111.

Ohara, H., Y. Nakamura, Y. Watanabe, X. Cao, Y. Yamazaki, H. Izumi-Nakaseko, K. Ando, H. Yamazaki, J. Yamazaki, T. Ikeda and A. Sugiyama (2015). "Azithromycin Can Prolong QT Interval and Suppress Ventricular Contraction, but Will Not Induce Torsade de Pointes." Cardiovasc Toxicol 15(3): 232-240.

Peters, D. H., H. A. Friedel and D. McTavish (1992). "Azithromycin. A review of its antimicrobial activity, pharmacokinetic properties and clinical efficacy." Drugs 44(5): 750-799.

Rapp, R. P. (1998). "Pharmacokinetics and pharmacodynamics of intravenous and oral azithromycin: enhanced tissue activity and minimal drug interactions." Ann Pharmacother 32(7-8): 785-793.

Ribeiro, C. M., H. Hurd, Y. Wu, M. E. Martino, L. Jones, B. Brighton, R. C. Boucher and W. K. O'Neal (2009). "Azithromycin treatment alters gene expression in inflammatory, lipid metabolism, and cell cycle pathways in well-differentiated human airway epithelia." PLoS One 4(6): e5806.

Shinkai, M., G. H. Foster and B. K. Rubin (2006). "Macrolide antibiotics modulate ERK phosphorylation and IL-8 and GM-CSF production by human bronchial epithelial cells." Am J Physiol Lung Cell Mol Physiol 290(1): L75-85.

Ter Horst, E. N., N. Hakimzadeh, A. M. van der Laan, P. Krijnen, H. W. Niessen and J. J. Piek (2015). "Modulators of Macrophage Polarization Influence Healing of the Infarcted Myocardium." Int J Mol Sci 16(12): 29583-29591.

Tsai, W. C., M. L. Rodriguez, K. S. Young, J. C. Deng, V. J. Thannickal, K. Tateda, M. B. Hershenson and T. J. Standiford (2004). "Azithromycin blocks neutrophil recruitment in Pseudomonas endobronchial infection." Am J Respir Crit Care Med 170(12): 1331-1339.

Yamaryo, T., K. Oishi, H. Yoshimine, Y. Tsuchihashi, K. Matsushima and T. Nagatake (2003). "Fourteen-member macrolides promote the phosphatidylserine receptor-dependent phagocytosis of apoptotic neutrophils by alveolar macrophages." Antimicrob Agents Chemother 47(1): 48-53.

Zarogoulidis, P., N. Papanas, I. Kioumis, E. Chatzaki, E. Maltezos and K. Zarogoulidis (2012). "Macrolides: from in vitro anti-inflammatory and immunomodulatory properties to clinical practice in respiratory diseases." Eur J Clin Pharmacol 68(5): 479-503.

Zhang, B., W. M. Bailey, T. J. Kopper, M. B. Orr, D. J. Feola and J. C. Gensel (2015). "Azithromycin drives alternative macrophage activation and improves recovery and tissue sparing in contusion spinal cord injury." J Neuroinflammation 12: 218.

Zimmermann, P., V. C. Ziesenitz, N. Curtis and N. Ritz (2018). "The Immunomodulatory Effects of Macrolides—A Systematic Review of the Underlying Mechanisms." Front Immunol 9: 302.

Zlatanova, I., C. Pinto and J. S. Silvestre (2016). "Immune Modulation of Cardiac Repair and Regeneration: The Art of Mending Broken Hearts." Front Cardiovasc Med 3: 40.

Stuhne-Sekalec, et al., Liposomes as carriers of macrolides: preferential association of erythromycin A and azithromycin with liposomes of phosphatidylglycerol containing unsaturated fatty acid(s), J. Microencapsulation, 1991 vol. 8, No. 2, 171-183.

Onyeji, et al., Activities of liposome-encapsulated azithromycin and rifabutin compared with that of clarithromycin against *Mycobacterium avium*-intracellulare complex in human macrophages, International Journal of Antimicrobial Agents 4 (1994) 281-289.

Montenez, et al., Interaction of the macrolide azithromycin with phospholipids. II. Biophysical and computer-aided conformational studies, European Journal of Pharmacology 314 (1996) 215-227.

Van Bambeke, et al., Interaction of the macrolide azithromycin with phospholipids. I. Inhibition of lysosomal phospholipase A 1 activity, European Journal of Pharmacology 314 (1996) 203-214.

Montenez, et al., Interactions of Macrolide Antibiotics (Erythromycin A, Roxithromycin, Erythromycylamine [Dirithromycin], and Azithromycin) with Phospholipids: Computer-Aided Conformational Analysis and Studies on Acellular and Cell Culture Models, Toxicology and Applied Pharmacology 156, 129-140 (1999).

Tyteca, et al., The Macrolide Antibiotic Azithromycin Interacts with Lipids and Affects Membrane Organization and Fluidity: Studies on Langmuir-Blodgett Monolayers, Liposomes and J774 Macrophages, J. Membrane Biol. 192, 203-215 (2003).

Tiukinhoy, et al., Novel Echogenic Drug-Immunoliposomes for Drug Delivery, Investigative Radiology • vol. 39, No. 2, Feb. 2004.

Berquand, et al., Interaction of the Macrolide Antibiotic Azithromycin with Lipid Bilayers: Effect on Membrane Organization, Fluidity, and Permeability, Pharmaceutical Research, vol. 22, No. 3, Mar. 2005, pp. 465-475.

Salem, et al., Liposome-Encapsulated Antibiotics, Methods in Enzymology, vol. 391, 2005, pp. 261-291.

Fa, et al., Effect of the antibiotic azithromycin on thermotropic behavior of DOPC or DPPC bilayers, Chemistry and Physics of Lipids 144 (2006) 108-116.

Liu, et al., Lipid emulsions as a potential delivery system for ocular use of azithromycin, Drug Development and Industrial Pharmacy, 2009; 35(7): 887-896.

Cory, et al., Azithromycin increases in vitro fibronectin production through interactions between macrophages and fibroblasts stimulated with Pseudomonas aeruginosa, J Antimicrob Chemother 2013; 68: 840-851.

Wallace, et al., Physicochemical Aspects of the Coformulation of Colistin and Azithromycin Using Liposomes for Combination Antibiotic Therapies, Journal of Pharmaceutical Sciences, vol. 102, No. 5, May 2013, pp. 1578-1587.

Shirey, et al., Agents that increase AAM differentiation blunt RSV-mediated lung pathology, Journal of Leukocyte Biology, vol. 96, Dec. 2014, pp. 951-955.

(56) References Cited

OTHER PUBLICATIONS

Solleti, et al., Antimicrobial properties of liposomal azithromycin for Pseudomonas infections in cystic fibrosis patients, J Antimicrob Chemother 2015; 70: 784-796.

Liu, et al., Novel antimicrobial peptide-modified azithromycin-loaded liposomes against methicillin-resistant *Staphylococcus aureus*, International Journal of Nanomedicine 2016:11 6781-6794.

Rajabi, et al., Topical liposomal azithromycin in the treatment of acute cutaneous leishmaniasis, Dermatologic Therapy, vol. 00, 2016, 00-00.

Madan, et al., Design, Preparation and Evaluation of Liposomal Gel Formulations for Treatment of Acne: In vitro and In vivo Studies, Drug Development and Industrial Pharmacy, vol. 45, 2019—Issue 3, Nov. 30, 2018, pp. 395-404.

Orr, et al., Spinal Cord Injury Scarring and Inflammation: Therapies Targeting Glial and Inflammatory Responses, Neurotherapeutics (2018) 15:541-553.

Ren, et al., Encapsulation of azithromycin ion pair in liposome for enhancing ocular delivery and therapeutic efficacy on dry eye, Molecular Pharmaceutics, Sep. 25, 2018.

Rukavina, et al., Azithromycin-loaded liposomes for enhanced topical treatment of methicil.lin-resistant *Staphyloccocus aureus* (MRSA) infections, International Journal of Pharmaceutics 553 (2018) 109-119.

Gensel, et al., Sexual Dimorphism of Pain Control: Analgesic Effects of Pioglitazone and Azithromycin in Chronic Spinal Cord Injury, Journal of Neurotrauma 36:2372-2376 (Aug. 1, 2019).

Ghosh, et al., Role of nanostructures in improvising oral medicine, Toxicology Reports 6 (2019) 358-368.

Haydar, et al., Azithromycin Polarizes Macrophages to an M2 Phenotype via Inhibition of the STAT1 and NF-kB Signaling Pathways, J Immunol published online Jul. 1, 2019.

Kopper, et al., Delayed Azithromycin Treatment Improves Recovery After Mouse Spinal Cord Injury, frontiers in Cellular Neuroscience, Nov. 8, 2019.

Vanic, et al., Azithromycin-liposomes as a novel approach for localized therapy of cervicovaginal bacterial infections, International Journal of Nanomedicine 2019:14 5957-5976.

Zhang, et al., Macrolide derivatives reduce proinflammatory macrophage activation and macrophage-mediated neurotoxicity, CNS Neurosci Ther. 2019;25:591-600.

Creameans, et al., Liposomal azithromycin modulates macrophage polarization toward an alternatively activated state, Autumn Immunology Conference, Nov. 22-25, 2019.

Creameans, et al., Liposomal azithromycin modulates macrophage polarization toward an alternatively activated state, 48th Autumn Immunology Conference, Nov. 24, 2019.

Creameans, et al., Liposomal azithromycin modulates macrophage polarization toward an alternatively activated state, Autumn Immunology Conference, Nov. 24, 2019.

* cited by examiner

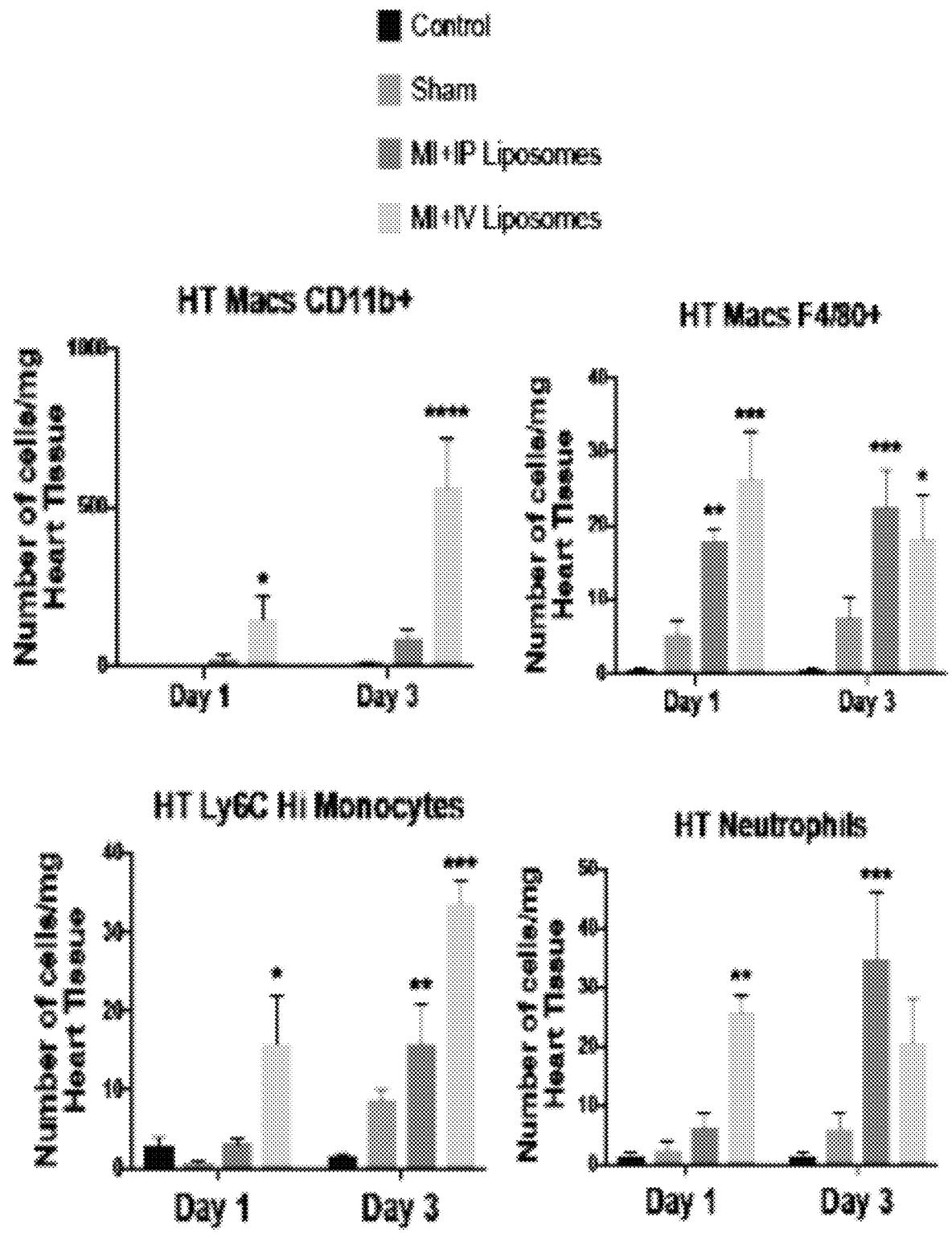
FIG. 2, Cont'd

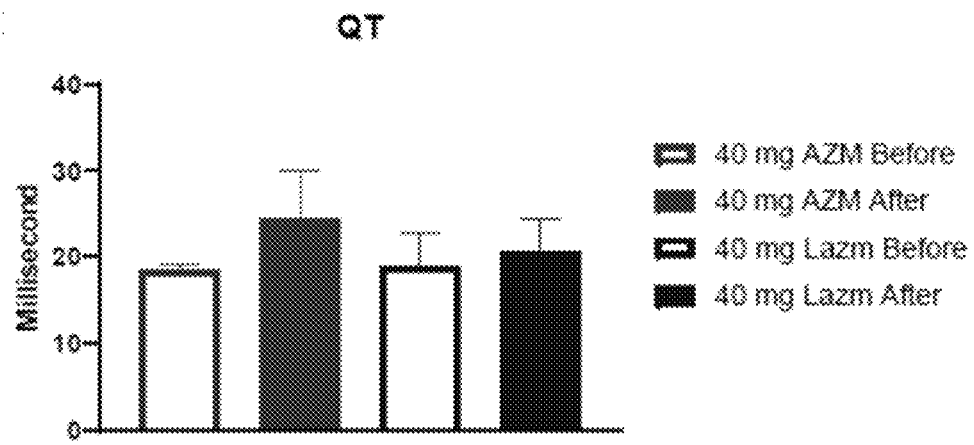
FIG. 4C
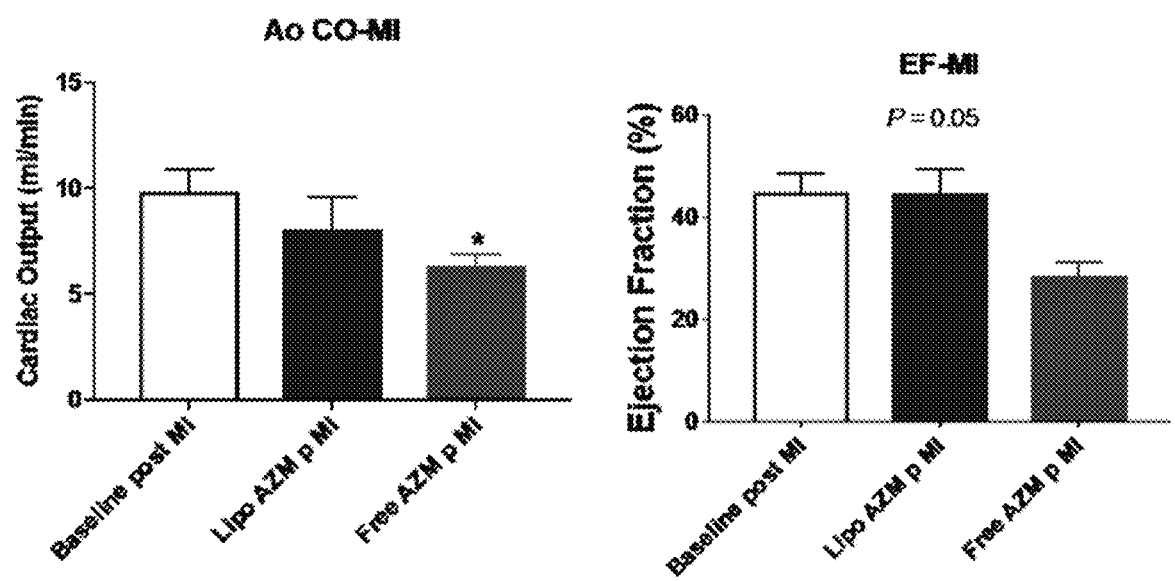
FIG. 4D
FIG. 4E

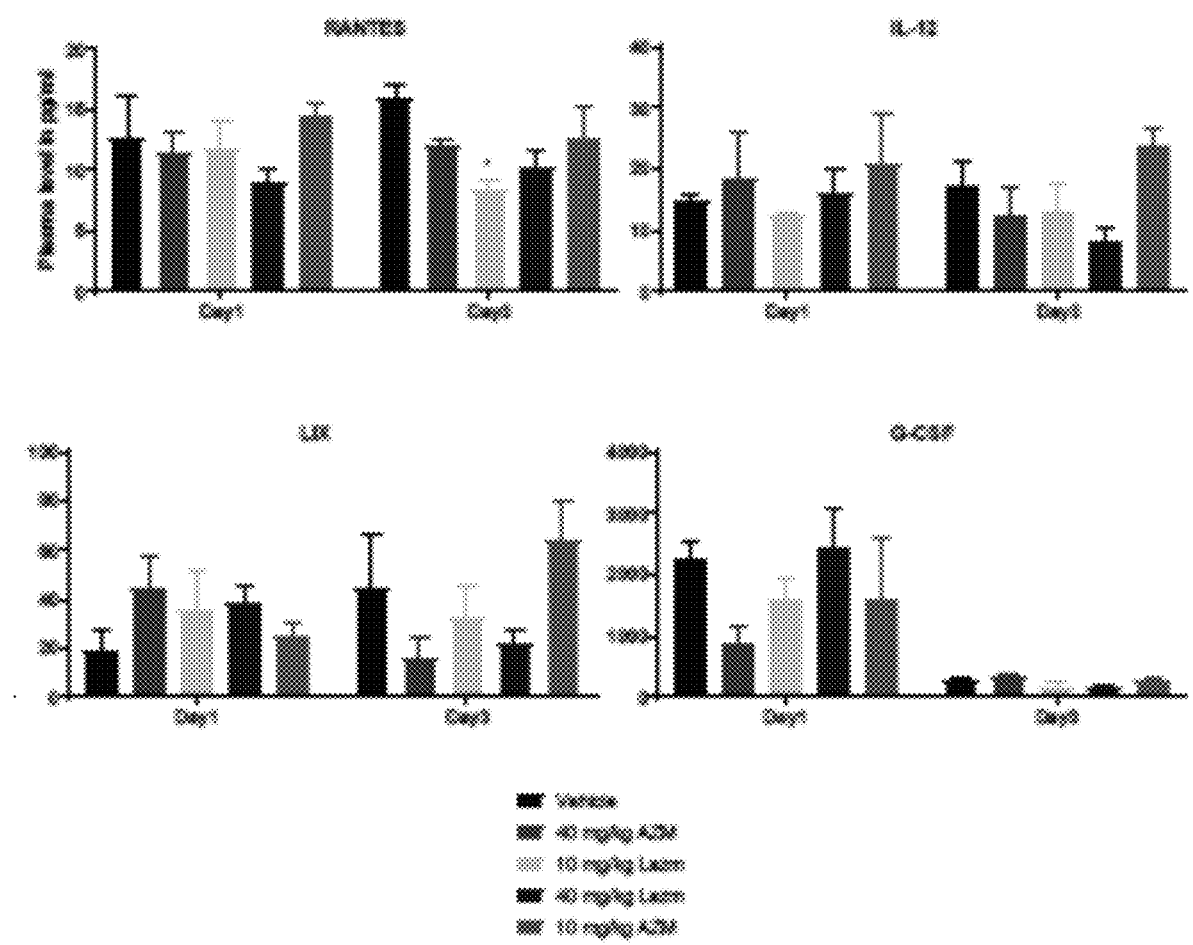
FIG. 13, Cont'd

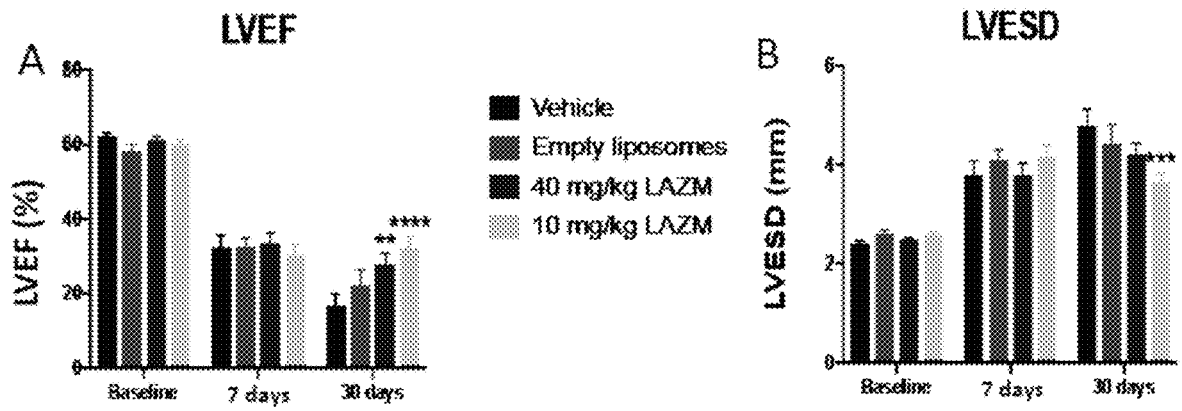
FIG. 18A
FIG. 18B
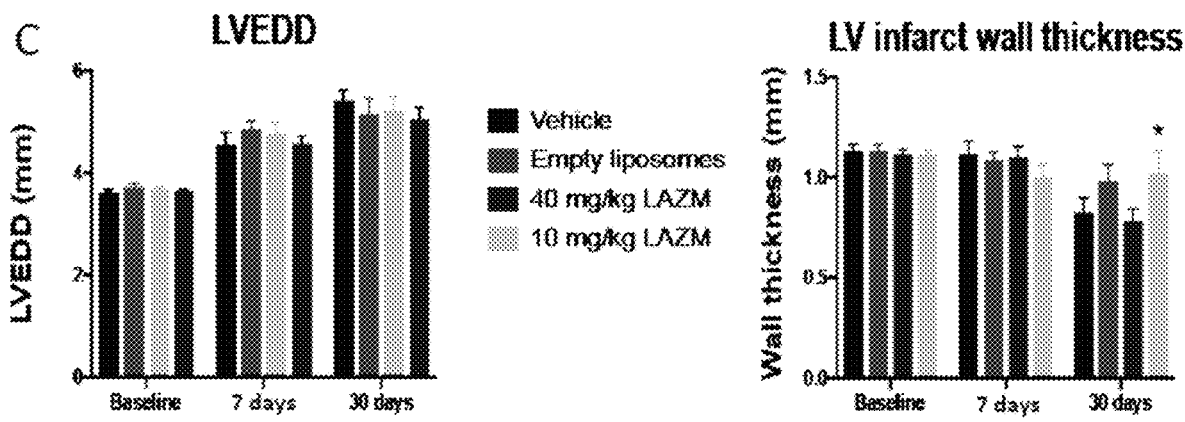
FIG. 18C
FIG. 18D
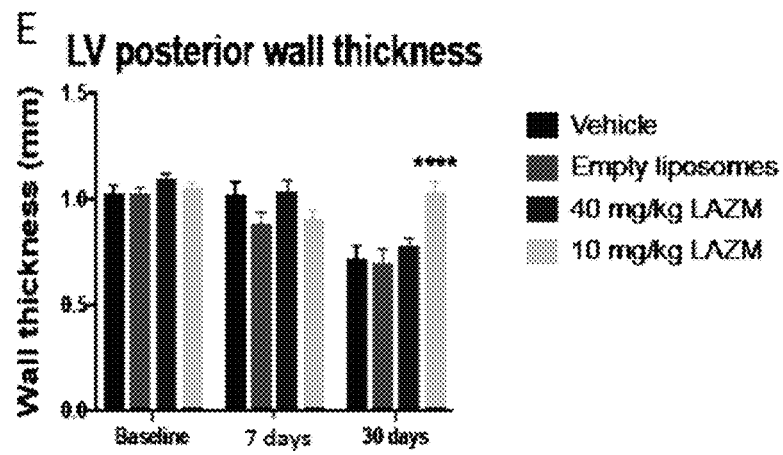
FIG. 18E

LIPOSOMAL COMPOUNDS AND METHODS OF USE THEREOF

RELATED APPLICATIONS

This application claims the benefit of U.S. Provisional Application Ser. No. 62/826,821, filed Mar. 29, 2019, the entire disclosure of which is incorporated herein by this reference.

GOVERNMENT INTEREST

This invention was made with government support under grant number R01 HL124266-02, awarded by the National Institutes of Health (NIH). The Government has certain rights in the invention.

TECHNICAL FIELD

The present disclosure is directed to liposomal compounds and methods of use thereof. In particular, the disclosure is directed to liposomal azithromycin and methods of use thereof for immune-suppression therapy.

BACKGROUND

Myocardial infarction (MI) remains a primary cause of morbidity and mortality globally, albeit hospitalization rates reduced in the last 15 years. Heart failure resulting from post-infarction remodeling is a major driver of cardiac death. Cardiomyocyte death and extracellular matrix (ECM) breakdown at the area of cardiac injury induce a potent and poorly controlled inflammatory response, interfering with healing and scar formation processes. Innate immune cells such as neutrophils, monocytes, and macrophages are key players in this response. After infarction, neutrophils are the first inflammatory cells to infiltrate the infarcted myocardium. While neutrophils play an important role in removing dead cells and debris, their byproducts may exacerbate cardiac damage. A recent study reveals that there are two activation states of neutrophils in the post-ischemic heart: pro-inflammatory (N1) and anti-inflammatory (N2) neutrophils. N1 neutrophils dominate the heart immediately after infarction and contribute to the development of adverse cardiac remodeling and heart failure while N2 neutrophils increase gradually after MI and have cardio-protective effects. Additionally, neutrophils can negatively impact post-MI healing through preferential recruitment of pro-inflammatory ($Ly6C^{hi}$), rather than anti-inflammatory monocytes) ($Ly6C^{lo}$).

Macrophages are essential in organizing the early post-MI inflammatory and subsequent reparative phase. They are generally classified into pro-inflammatory/classically activated/M1 and anti-inflammatory/alternatively activated/reparative/M2 macrophages based on gene profile and function. Pro-inflammatory macrophages are dominant at day 1-3 post-MI and mediate the inflammatory process. Following this early inflammatory phase, at day 5-7, reparative macrophages are the most prevalent and are characterized by high expression levels of IL-10, IL-1ra, and decoy type II receptors. As a result of the production of these mediators, M2 macrophages play a central role in inflammation resolution and demonstrate robust anti-inflammatory effects, potentially involved in tissue remodeling and angiogenesis.

There is a growing body of evidence showing that repolarization of macrophages to the reparative phenotype is protective against early development of ischemic lesion and its subsequent cardiac remodeling. In view thereof, several therapeutic agents have been tested to alleviate cardiac remodeling post-MI through systemic administration. However, the therapeutic agents tested to date suffer limited efficacy due to poor bioavailability in the heart or dose-limiting adverse effects. Accordingly, there remains a need for articles and methods to treat post-infarction remodeling.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a composition for improving cardiac recovery following myocardial infarction, the composition including a non-PEGylated liposome. In some embodiments, the non-PEGylated liposome comprises a liposomal azithromycin formulation. In some embodiments, the azithromycin is encapsulated by the liposome. In some embodiments, the azithromycin is included at between 10 and 30 mol % based on phospholipid content of the composition.

Also provided herein, in some embodiments, is a method of treating a subject following myocardial infarction, the method including administering a pharmaceutically effective amount of a non-PEGylated liposome to the subject. In some embodiments, the non-PEGylated liposome comprises liposomal azithromycin. In one embodiment, the liposomal azithromycin includes azithromycin encapsulated in a liposome. In one embodiment, the azithromycin is included at between 10 and 30 mol % based upon phospholipid content.

In some embodiments, administering the non-PEGylated liposome reduces susceptibility to chronic scar enlargement. In some embodiments, administering the non-PEGylated liposome decreases inflammatory change in the heart. In some embodiments, administering the non-PEGylated liposome reduces the ratio of pro-/anti-inflammatory macrophages. In one embodiment, administering the non-PEGylated liposome reduces the ratio without affecting total macrophage count. In another embodiment, administering the non-PEGylated liposome decreases pro-inflammatory macrophages. In a further embodiment, the pro-inflammatory macrophages include $CD45^+/Ly6G^-/F4-80^+CD11c^+$. In another embodiment, administering the non-PEGylated liposome increases reparative macrophages. In a further embodiment, the reparative macrophages include $CD45^+/Ly6G^-/F4-80^+/CD11c^-/CD206^+$.

Further provided herein, in some embodiments, is a method of treating a sterile inflammatory disease in a subject, the method including administering a pharmaceutically effective amount of a non-PEGylated liposome to the subject. In some embodiments, the sterile inflammatory disease shares a similar inflammatory profile with myocardial infarction. In one embodiment, the sterile inflammatory disease is ischemic stroke. In one embodiment, the sterile inflammatory disease is a spinal cord injury.

Further features and advantages of the presently-disclosed subject matter will become evident to those of ordinary skill in the art after a study of the description, figures, and non-limiting examples in this document.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein:

FIGS. 4A-E show graphs illustrating hemodynamic effects of free and liposomal AZM. Changes in (A) heat rate, (B) RR interval, (C) QT interval, (D) ejection fraction, and (E) cardiac output after retro-orbital administration of various doses of Lazm or free AZM. Data shows that the liposomal formulation of AZM is protective against hemodynamic changes induced by free AZM. (N=3, P<0.01 and *P<0.001 compared to baseline of the corresponding group). Data presented as mean±SEM. AZM, azithromycin; Lazm, liposomal azithromycin.

P<0.01, *P<0.001, and ****P<0.0001 compared to vehicle control). Data presented as mean±SEM. AZM, azithromycin; Lazm, liposomal azithromycin; Ht, heart.

Figure 10A:
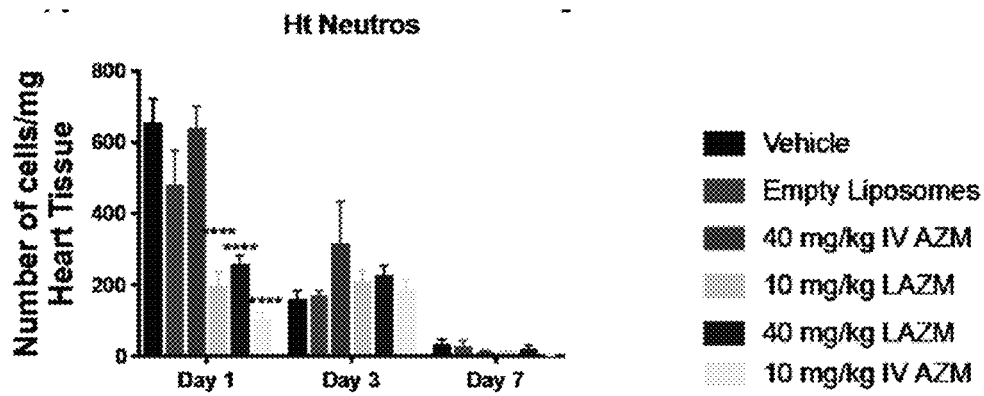
Figure 10B:
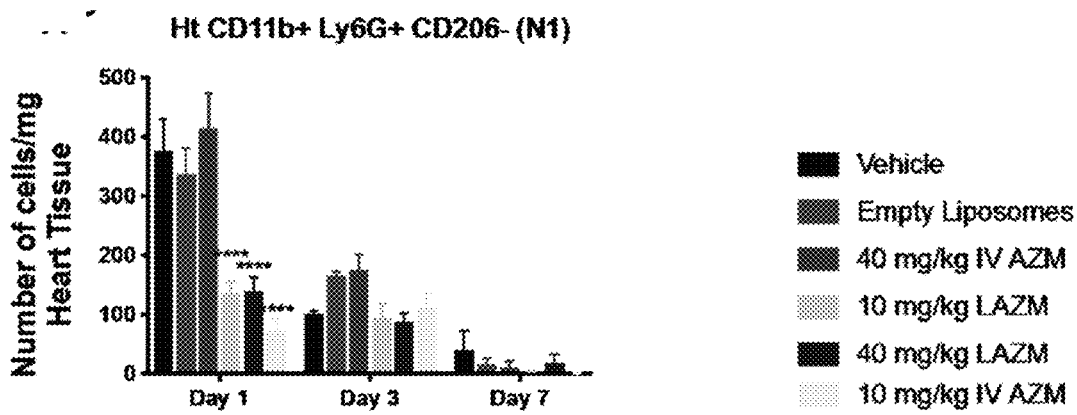
Figure 10C:
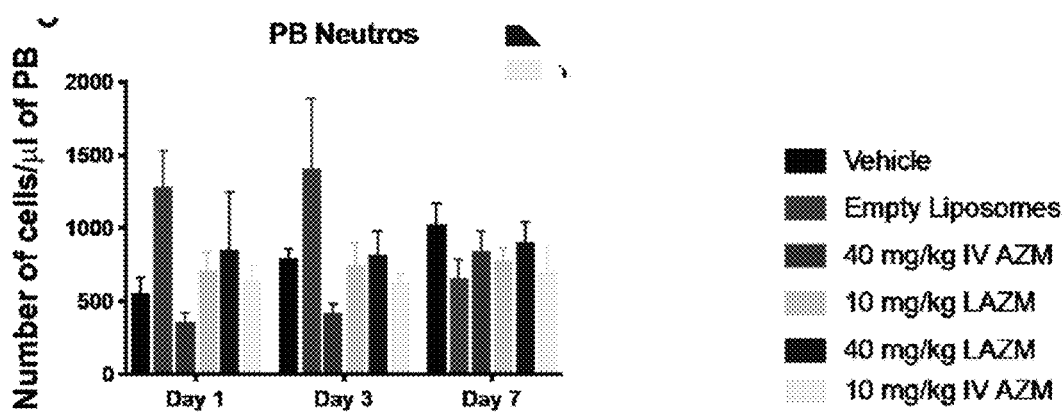

FIGS. 10A-C show graphs illustrating Lazm treatment reducing neutrophil counts, in particular N1 neutrophils. (A) FACS analyses suggest that neutrophil counts are significantly decreased in the Ht, (B) specifically N1 (CD11b+ Ly6G+CD206−) neutrophils in Lazm treated mice on day 1 post-MI. No changes in neutrophils were noted with free AZM treatment. (C) Neutrophils were reduced on day 7 in Lazm groups in blood (N=4 animals/group/time point, P<0.01 and *P<0.001 compared to vehicle control). Data presented as mean±SEM. AZM, azithromycin; Lazm, liposomal azithromycin; Ht, heart; PB, peripheral blood.

Figure 11A:
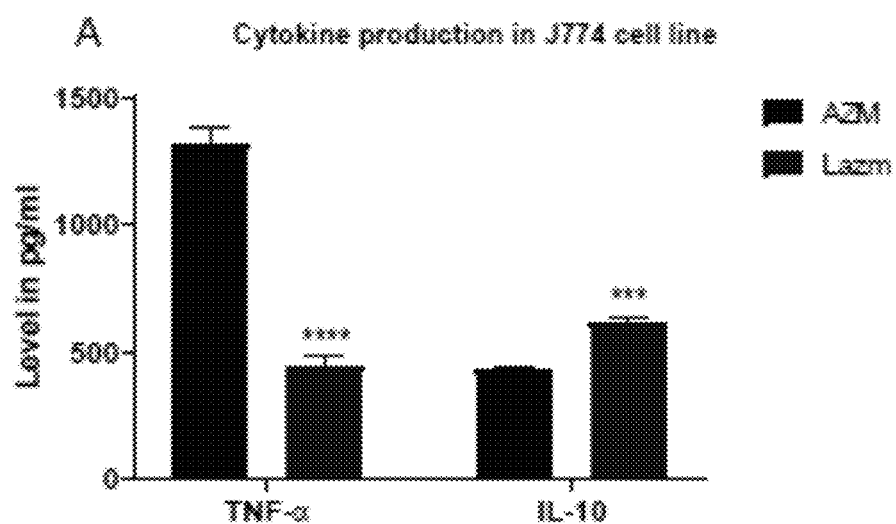
Figure 11B:
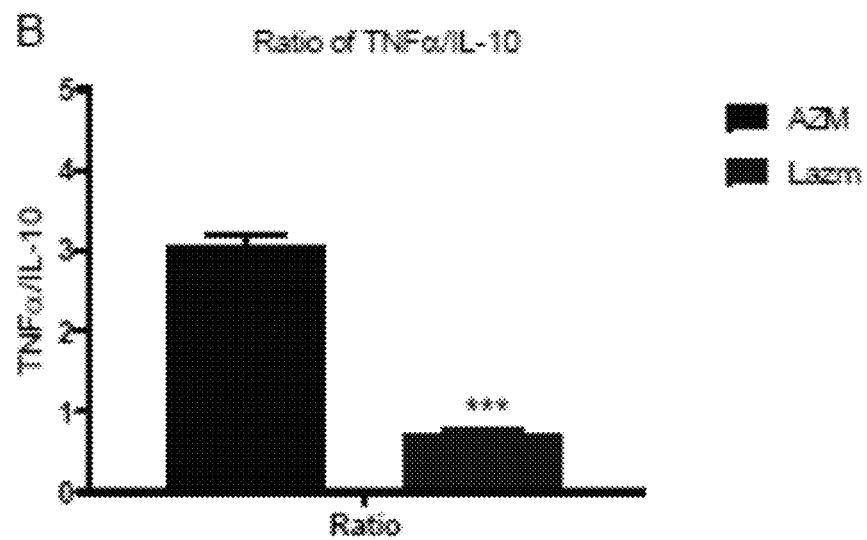

FIGS. 11A-B show graphs illustrating Liposomal azithromycin producing a more significant shift in macrophage response towards the anti-inflammatory state. (A) Quantitative analyses of pro-inflammatory cytokine, TNF-α, and anti-inflammatory cytokine, IL-10, production from J774 macrophages subjected to LPS stimulation for 48 hours. (B) The analyses demonstrate a more significant reduction of TNF-α with Lazm compared to free AZM at 48 hours post-MI. Moreover, IL-10 production is additionally enhanced with Lazm. Treatment (two independent experiments and 4 replicates/time point, *P<0.001 and **P<0.0001 compared to free AZM). Data presented as mean±SEM. AZM, azithromycin; Lazm, liposomal azithromycin; IL-10, interleukin 10; TNF-α, tumor necrosis factor-alpha.

FIGS. 12A-D show graphs illustrating Lazm modulating pro- and anti-inflammatory cytokine expression. (A) Heart homogenate (Ht) cells were used to quantify pro-inflammatory cytokine secretion via RT-PCR. Pro-inflammatory cytokine expression, including iNOS, TNF-α, MCP-1, IL-1β and IL-6c. Data shows significant reduction in inflammatory cytokines at days 1 and 3 with Lazm treatment in Ht. (B) Heart homogenate (HT) cells were used to quantify anti-inflammatory cytokine secretion via RT-PCR. Anti-inflammatory IL-10, TGF-β, Fizz1, and YM1, ARG, PPARg, IL-4 expression. Data shows significant increase in anti-inflammatory cytokines on days 1, 3 and, 7 with Lazm treatment in HT. (C) Peripheral blood cells were used to quantify pro-inflammatory cytokine secretion via RT-PCR. Pro-inflammatory cytokine expression, including TNF-α, MCP-1, IL-1β and IL-6. Data show significant reduction in inflammatory cytokines at days 1 and 3, and 7 with Lazm treatment in blood. (D) Peripheral blood cells were used to quantify anti-inflammatory cytokine secretion via RT-PCR. Anti-inflammatory TGF-β, Fizz1, and YM1 expression. Data show significant increase in anti-inflammatory cytokines in days 1, 3 and, 7 with Lazm treatment in blood. n=4 animals/group/time point, *P<0.05, P<0.01, *P<0.001, and ****P<0.0001 compared to the vehicle control. Data presented as mean±SEM. ARG, arginase; AZM, azithromycin; Fizz1, found in inflammatory zone 1; Ht, heart; IL-1β, interleukin 1 beta; IL-4, interleukin 4; IL-6, interleukin 6; IL-10, interleukin-10; iNOS, inducible nitric oxide synthase; Lazm, liposomal azithromycin; MCP-1, monocyte chemoattractant protein-1; PB, peripheral blood; PPARγ, peroxisome proliferator-activated receptor gamma; TGF-10, tissue growth factor 1 beta; TNF-α, tumor necrosis factor-alpha; YM1 (Chil3), chitinase-like 3.

Figure 13:
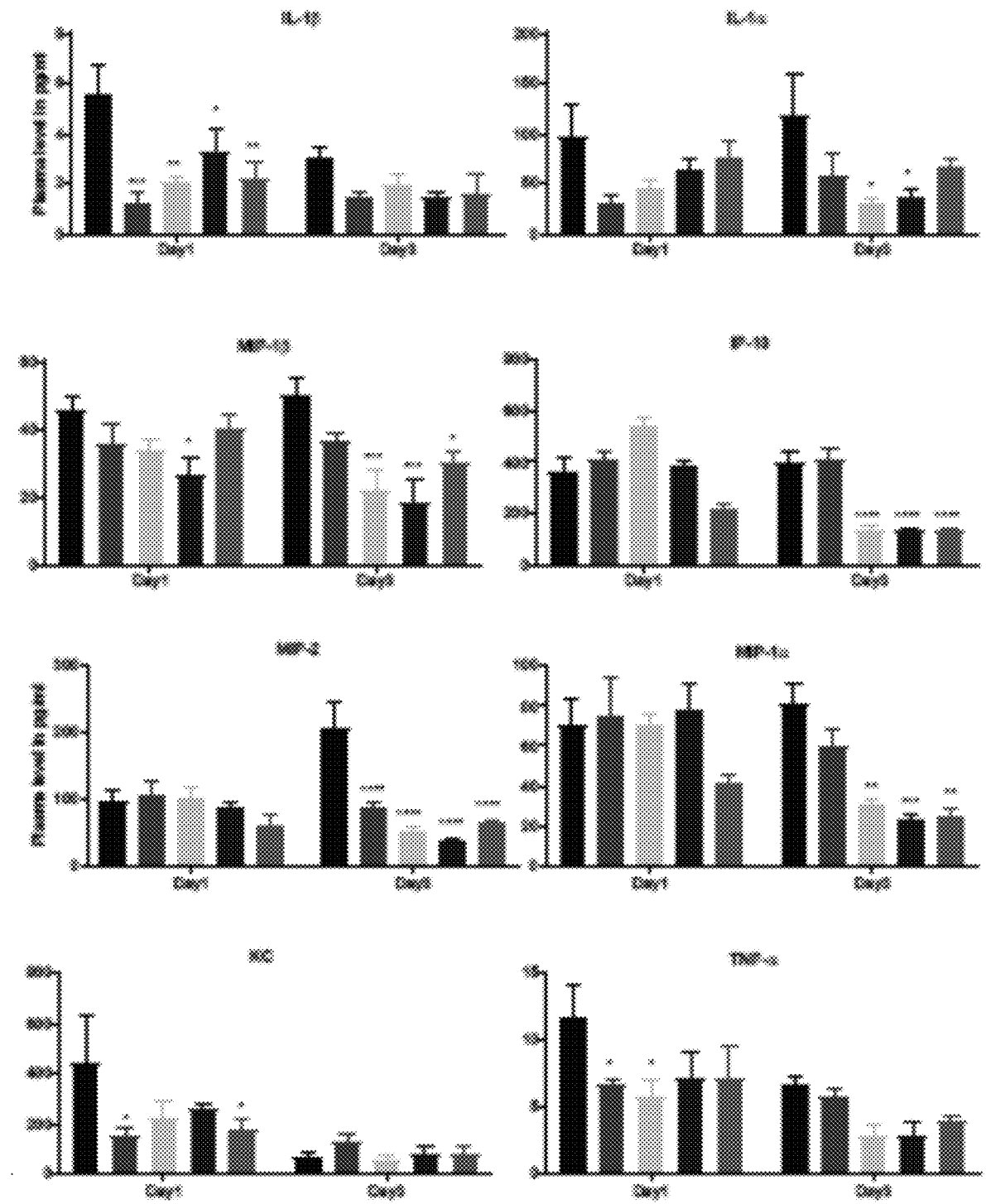

FIG. 13 shows graphs illustrating Lazm modulating pro-inflammatory cytokine and chemokine production. Plasma quantification of pro-inflammatory cytokine and chemokine secretion via Luminex assay. Data shows significant reduction in inflammatory cytokines and chemokines at days 1 and 3 with Lazm therapy (n=4 animals/group/time point, *P<0.05, P<0.01, *P<0.001, and ****P<0.0001 compared to the vehicle control). Data presented as mean±SEM. AZM, azithromycin; Lazm, liposomal azithromycin; IL-1, interleukin 1; TNF-α, tumor necrosis factor-alpha; RANTES, regulated on activation, normal T cell expressed and secreted; 11-12, interleukin 12; MW, macrophage inflammatory protein; KC, Keratinocyte chemoattractant; IP, Inducible protein; LIX, Lipopolysaccharide-induced CXC chemokine; G-MCSF, Granulocyte-Macrophage Colony-Stimulating Factor.

Figure 14A:
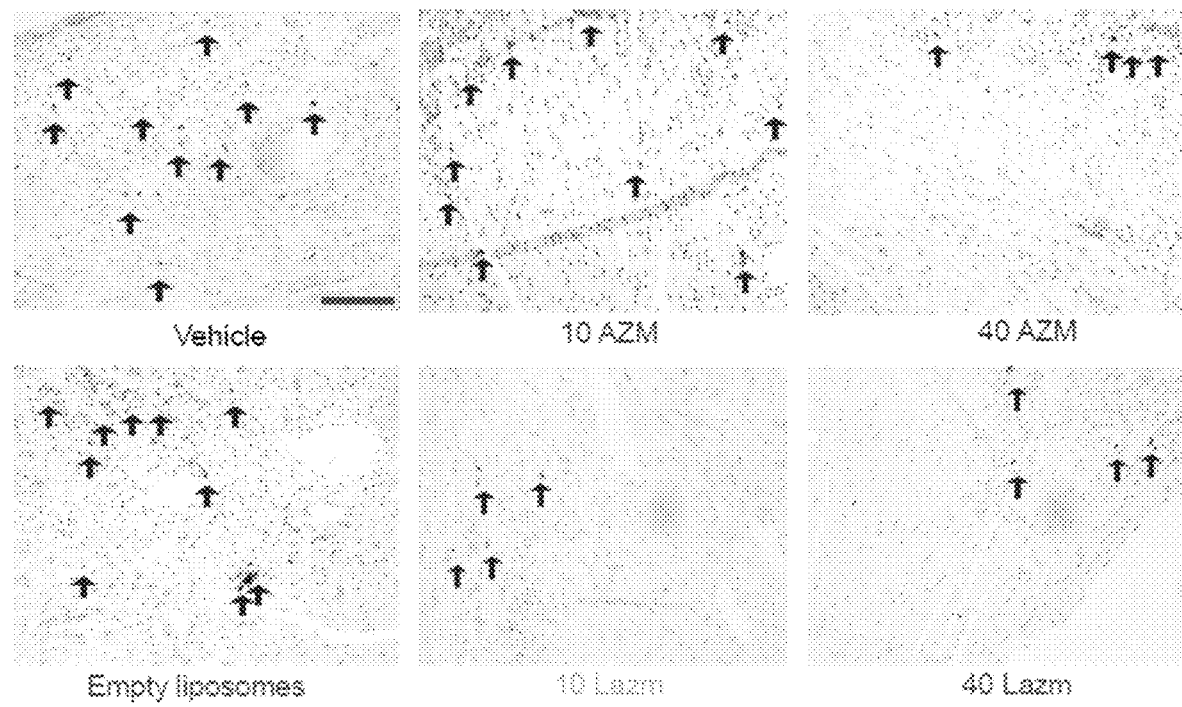
Figure 14B:
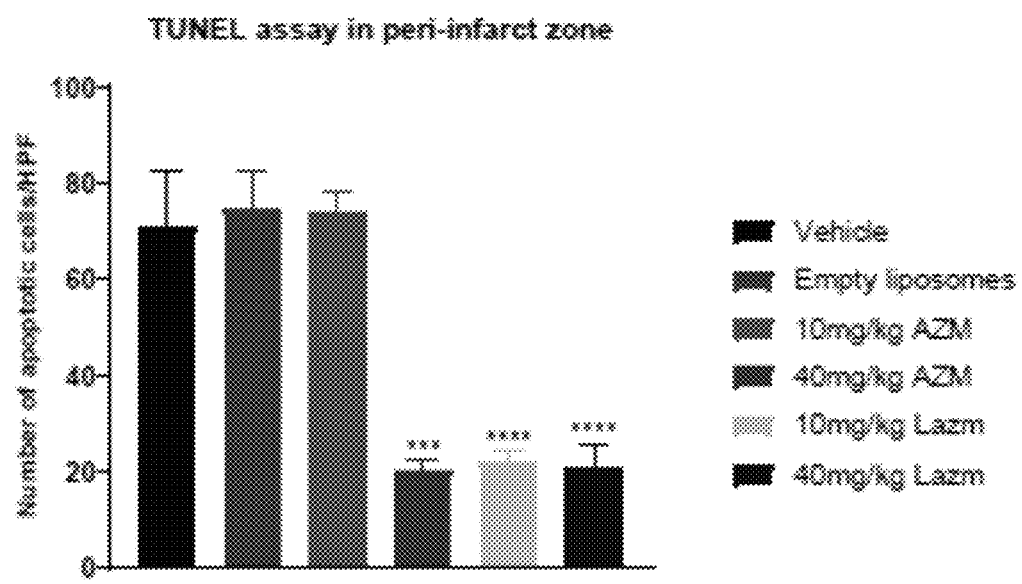

FIGS. 14A-B show images and graphs illustrating AZM reducing apoptosis in the heart post-infarction. (A) shows representative light microscope images of TUNEL staining of peri-infarct regions in controls, free AZM, and Lazm treated mice 3 days post-MI. (B) represents quantitative analysis of apoptosis which reveals a remarkable reduction of TUNEL positive cells in free and liposomal AZM treated groups compared to the vehicle control group (n=4 animals/group, P<0.01 and *P<0.001 compared to vehicle control). Scale bars represent 100 ηm. Data presented as mean±SEM. AZM, azithromycin; Lazm, liposomal azithromycin.

Figure 15A:
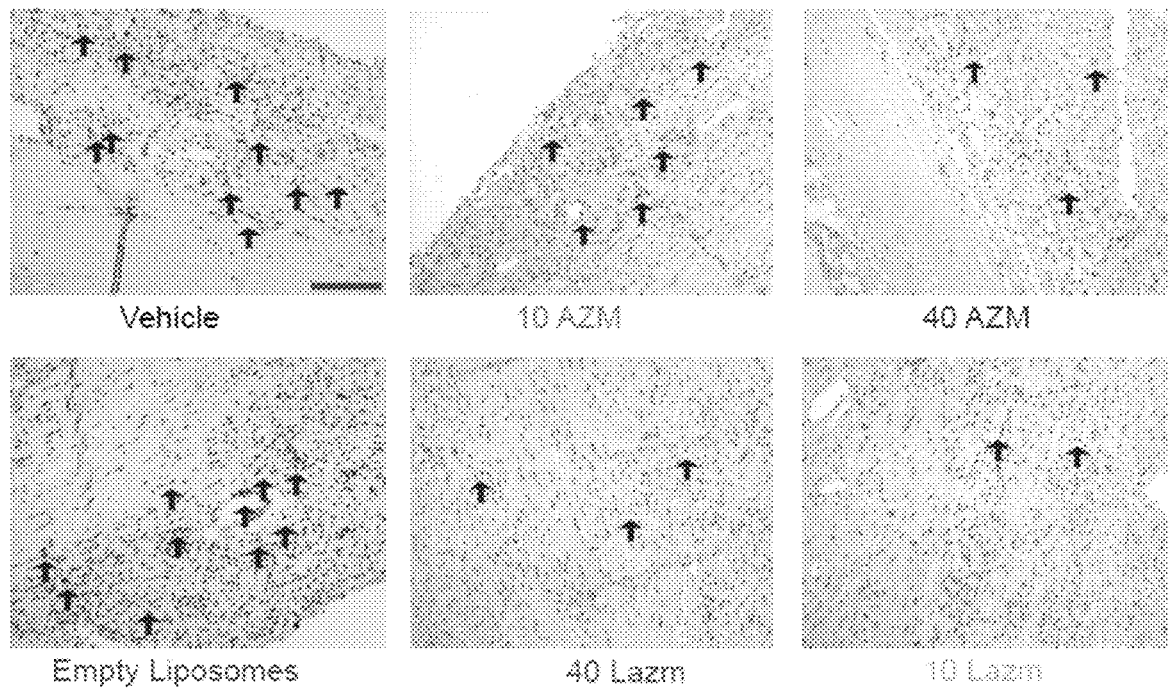
Figure 15B:
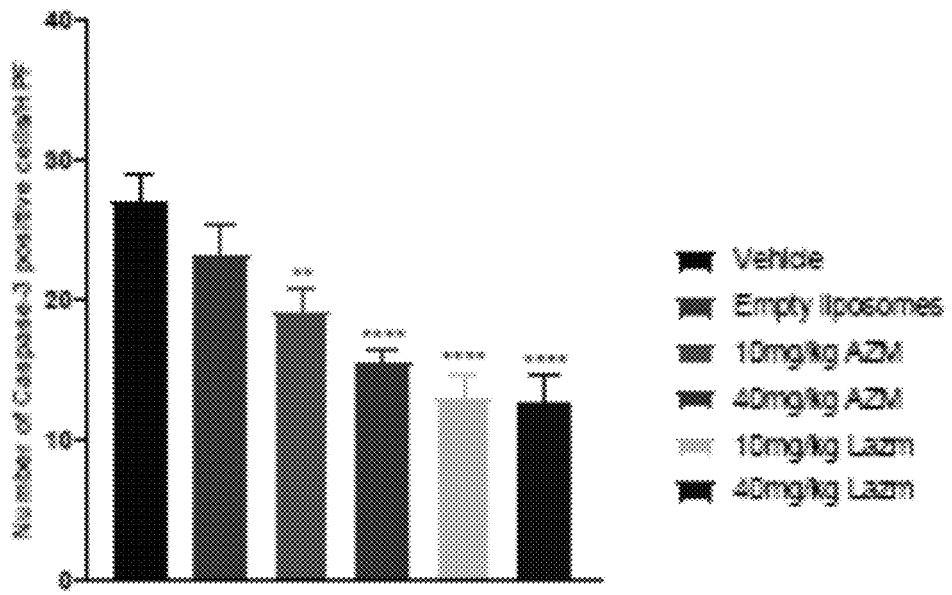

FIGS. 15A-B show images and a graph illustrating AZM reducing apoptosis in the heart post-infarct. (A) shows representative light microscope images of caspase-3 staining for peri-infarct regions in controls, free AZM, and Lazm treated mice 3 days post-MI. (B) represents quantitative analyses of apoptosis which reveal a remarkable reduction of caspase-3 positive cells in free and liposomal AZM treated groups compared to the vehicle control group (n=4 animals/group, P<0.01 and **P<0.0001 compared to vehicle control). Scale bars represent 100 μm. Data presented as mean±SEM. AZM, azithromycin; Lazm, liposomal azithromycin.

Figure 16A:
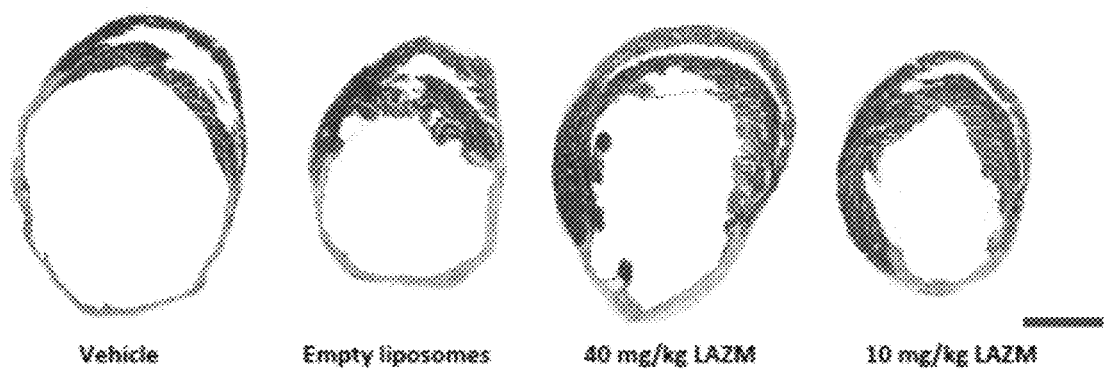
Figure 16B:
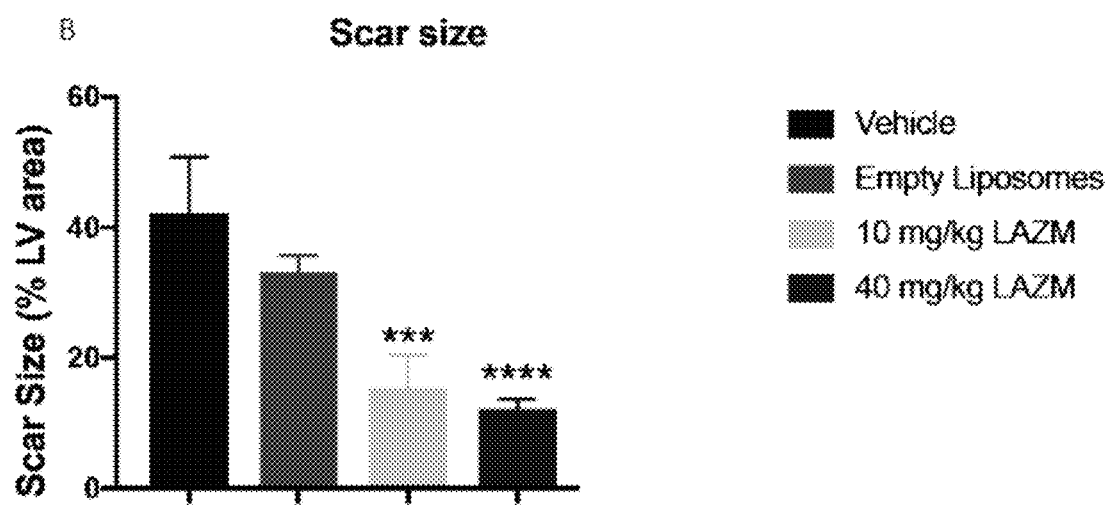

FIGS. 16A-B show an image and a graph illustrating Lazm therapy reducing scar size after infarct. (A) shows representative Masson's trichrome staining at 30 days post-MI in control, free AZM, and Lazm treated groups, indicating a marked reduction in scar size with liposomal and free AZM. (B) represents quantitative analysis of scar as a percentage of LV area, which shows significant reduction in liposomal and free AZM treated groups relative to the vehicle control group (n=6-10 animals/group, P<0.01, *P<0.001 and ****P<0.0001 compared to the vehicle control). Scale bars represent 50 Data presented as mean±SEM. AZM, azithromycin; Lazm, liposomal azithromycin.

Figure 17A:
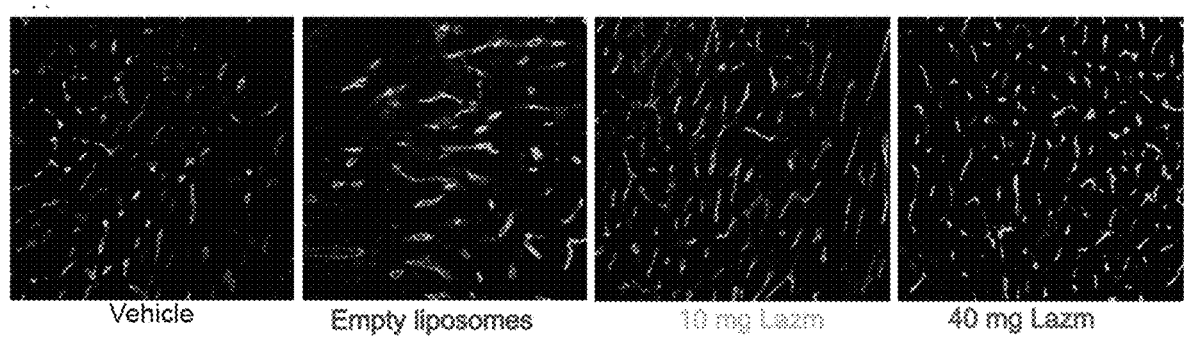
Figure 17B:
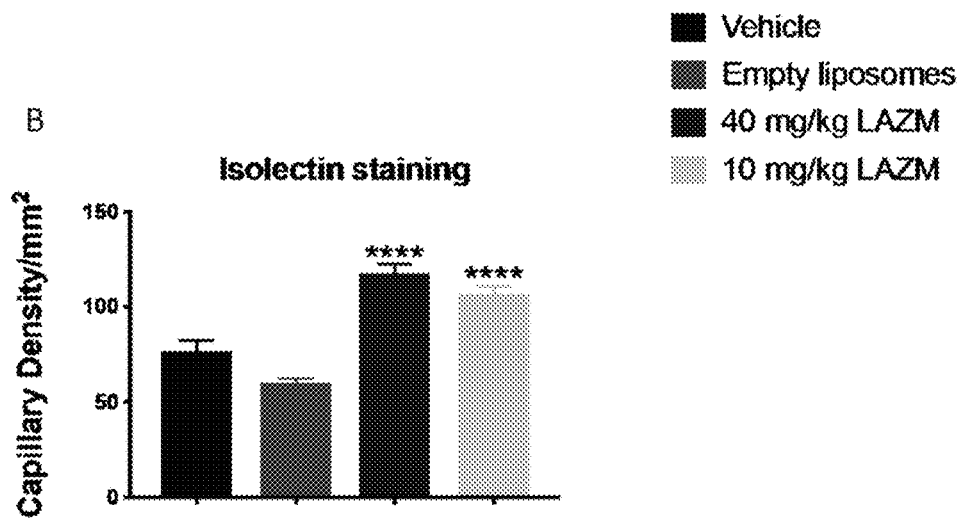

FIGS. 17A-B show images and a graph illustrating Lazm therapy promoting angiogenesis after infarct. (A) shows representative isolectin staining (Green) at 30 days post-MI for capillary density in the peri-infarct region in control, free AZM, and Lazm treated animals. This data demonstrates higher capillary density in Lazm groups compared to vehicle control. (B) is quantitative analysis of capillary density, which confirms a higher rate of angiogenesis and capillary density in Lazm treated groups (n=6-10 animals/group, ****P<0.0001 compared to the vehicle control). Scale bars represent 50 μm. Data presented as mean±SEM. AZM, azithromycin; Lazm, liposomal azithromycin.

FIGS. 18A-E show graphs illustrating Lazm therapy improving adverse cardiac remodeling. 30 days following MI, echocardiography was performed on control, free AZM, and Lazm treated animals to evaluate left ventricular function and remodeling parameters. Quantitative analyses demonstrate significant recovery in LV function as assessed by (A) ejection fraction (LVEF), which significantly improved in Lazm groups. Data also shows significant improvement in LV adverse remodeling parameters such as (B) end-systolic diameter (LVESD) and (C) end-diastolic diameter (LVEDD). (D-E)Additionally, significantly thicker infarct walls suggestive of enhanced recovery and regeneration were observed, which are more significantly enhanced with low dose Lazm. (n=6-10 animals/group, *P<0.05,P<0.01, *P<0.001, and ****P<0.0001 compared to the vehicle control). Data presented as mean±SEM. AZM, azithromycin; Lazm, liposomal azithromycin.

Figure 19:
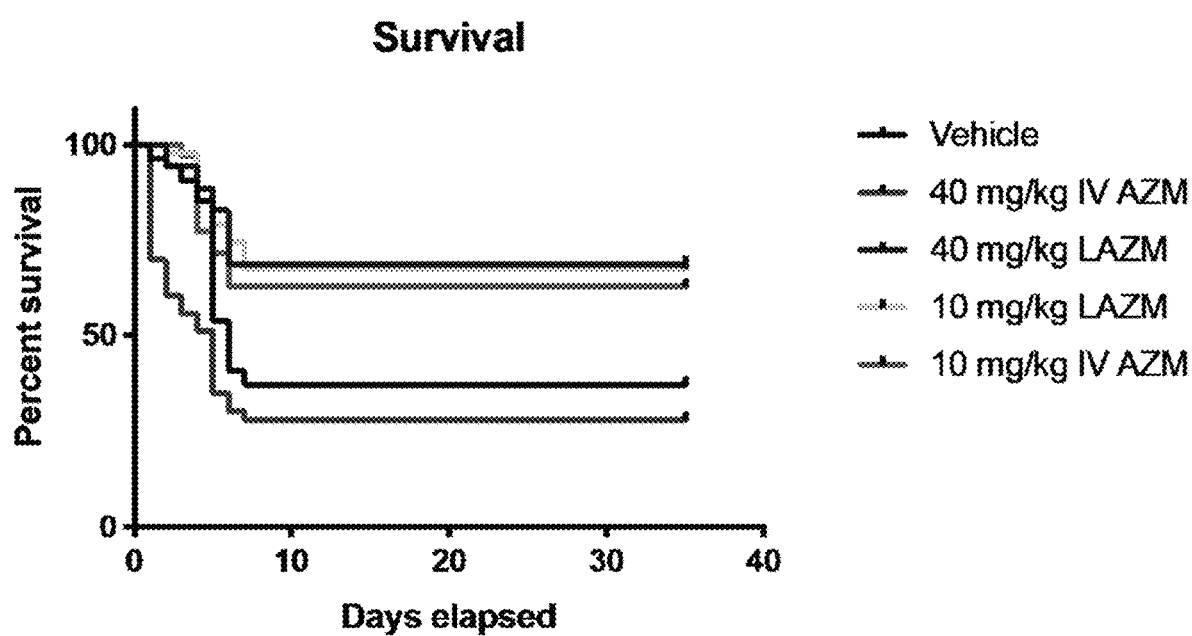

FIG. 19 shows a graph illustrating AZM therapies enhancing survival. Survival curves of free/liposomal AZM and vehicle-treated mice 35 days post-MI demonstrate a marked improvement in survival with AZM treatment. Mortality in 40 mg/kg IV AZM group occurs during the drug administration due to severe changes in cardiac conduction and hemodynamic parameters. While mice in other groups died of cardiac rupture, a common complication after MI surgery. (vehicle group, n=34, 40 mg/kg IV AZM group, n=33, 40 mg/kg Lazm group, n=35, 10 mg/kg Lazm group, n=31, 10 mg/kg IV AZM, n=35). AZM, azithromycin; Lazm, liposomal azithromycin.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as commonly understood by one of ordinary skill in the art to which the disclosure belongs. Any methods and materials similar to or equivalent to those described herein can be used in the practice or testing of the present disclosure, including the methods and materials are described below.

Following long-standing patent law convention, the terms "a," "an," and "the" refer to "one or more" when used in this application, including the claims. Thus, for example, reference to "a cell" includes a plurality of cells, and so forth.

The terms "comprising," "including," and "having" are intended to be inclusive and mean that there may be additional elements other than the listed elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration, percentage, or the like is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

All combinations of method or process steps as used herein can be performed in any order, unless otherwise specified or clearly implied to the contrary by the context in which the referenced combination is made.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with an ischemic injury, such as a myocardial infarction.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

The presently-disclosed subject matter relates to compositions and methods for improving cardiac functional recovery following myocardial infarction (MI). In some embodiments, the composition includes a non-PEGylated liposome. For example, in one embodiment, the composition is a liposomal formulation of azithromycin (Lazm). In another embodiment, the azithromycin, which is a macrolide antibiotic, is encapsulated by the liposome. As will be appreciated by those skilled in the art, liposomes include one or more phospholipid bilayers surrounding an aqueous core, which can hold both lipophilic and hydrophilic compounds.

The liposomal azithromycin may be formed by any suitable method. For example, in some embodiments, the Lazm is formed using a thin film hydration method. In one embodiment, the method includes equal molar ratios of distearyl phosphatidylcholine (DSPC), distearyl phosphatidylglycerol (DSPG), and cholesterol. In another embodiment, the azithromycin is included at between 10 and 30 mol % based on phospholipid content. In a further embodiment, the lipids and the azithromycin are mixed in chloroform and methanol at the desired ratio, and then the organic solvents are removed by rotary evaporation to yield a thin film. This lipid/drug film is hydrated (e.g., in phosphate buffered saline) and sonicated to form unilamellar vesicles. Finally, these unilamellar vesicles are extruded (e.g., through 200 nm polycarbonate membranes) to obtain uniform particle size.

In some embodiments, liposomal dosage forms are effective as a drug delivery strategy for phagocyte-targeted therapy, producing lower immunogenic reaction, higher biocompatibility and specificity, and greater drug stability, as compared to free therapeutic agents. Additionally, in some embodiments, as compared to free azithromycin, the liposomal formulations disclosed herein achieve higher drug concentration at sites of cardiac injury. Furthermore, in some embodiments, liposomes provide enhanced capacity to specifically deliver therapeutic agents to the site of injury through increased cellular and vascular permeability in the injured myocardium. For example, after parenteral administration, liposomes are naturally taken up by mononuclear phagocytes, and thus can harness the physiological function of these cells to mediate a targeted delivery and promote the therapeutic efficacy of the agent. Still further, in some embodiments, the liposomal formulation reduces or eliminates potential off-target effects and/or cardiac toxicity as compared to free azithromycin.

Also provided herein, in some embodiments, are methods of treating myocardial infarction (MI) and/or improving cardiac functional recovery following MI. In some embodiments, the method includes administering the non-PEGylated liposomal composition to a subject in need thereof. Without wishing to be bound by theory, it is believed that the non-PEGylated liposomal compositions disclosed herein shift macrophages to the reparatory state post-MI, which enhances cardiac recovery. For example, in some embodiments, administration of the liposomal azithromycin following ischemic injury alters inflammation and polarizes macrophages to the alternatively activated state in inflammatory conditions. Repolarizing macrophages towards the anti-inflammatory activation state in peri-infarct zones can protect more cardiomyocytes from death, reducing infarct expansion and the subsequent adverse cardiac remodeling. Accordingly, in some embodiments, the alternatively activated state following administration of the non-PEGylated liposomal composition, such as Lazm, enhances post-MI cardiac recovery, preserves the heart from acute injury after ischemia, reduces susceptibility to chronic scar enlargement, and/or reduces mortality.

In some embodiments, the administration of Lazm decreases tissue edema, decreases inflammatory change, reduces the ratio of pro-/anti-inflammatory macrophages, reduces neutrophil counts, shifts cytokine production (e.g., TNF-α and IL-10) towards an anti-inflammatory pattern, reduce apoptosis, reduce scar size, increase the density of newly formed blood vessels (i.e., enhance angiogenesis), preserve the thickness of the infarcted wall, or a combination thereof. In one embodiment, reducing the ratio of pro-/anti-inflammatory macrophages includes decreasing pro-inflammatory macrophages (e.g., CD45$^+$/Ly6G$^-$/F4-80$^+$/CD11c$^+$) and/or increasing reparative macrophages (e.g., CD45$^+$/Ly6G$^-$/F4-80$^+$/CD11c$^-$/CD206$^+$). In another embodiment, decreasing pro-inflammatory macrophages and/or increasing reparative macrophages does not affect total macrophage count, but rather influences polarization in favor of the reparative phenotype. In a further embodiment, this effect is increased with liposomal azithromycin as compared to free azithromycin.

Additionally or alternatively, in some embodiments, in contrast to free azithromycin where pre-MI administration and high doses limit the clinical translation, the liposomal azithromycin promotes early bioavailability. For example, in one embodiment, after administration, the increased vascular permeability in the injured post-infarct myocardium facilitates accumulation of the non-PEGylated liposomes. In another embodiment, the non-PEGylated liposomes disclosed herein are readily engulfed by phagocytes at sites of tissue injury. In a further embodiment, the non-PEGylated liposomes preferentially accumulate in phagocytes, such as neutrophils and macrophages, while being taken up by less than 1% of non-immune cells in the heart. In such embodiments, the non-PEGylated liposomes accumulate in the infarct and peri-infarct regions of the heart, consistent with geographic accumulation of infiltrating phagocytes. As such, in contrast to free therapeutic agents, the liposomal composition disclosed herein provides similar or greater efficacy with decreased amounts of the therapeutic agent. Accordingly, in some embodiments, the low dose of liposomal azithromycin, started after MI, effectively resolves post-MI inflammation and improves adverse cardiac remodeling with lower risk of adverse effects.

As will be appreciated by those skilled in the art, the method is not limited to treating myocardial infarction and includes other sterile inflammatory diseases that share similar inflammatory profile with MI, such as, but not limited to, ischemic stroke and spinal cord injury. Other treatments include, but are not limited to, lung infection or other traumatic inflammatory conditions. In some embodiments, the liposomal encapsulation is truly protective from the potential unwanted effects of AZM. Furthermore, the prepared liposomes in this study can be harnessed to deliver other therapeutic agents to the injured myocardium.

The presently-disclosed subject matter is further illustrated by the following specific but non-limiting examples. The following examples may include compilations of data that are representative of data gathered at various times during the course of development and experimentation related to the presently-disclosed subject matter. Those skilled in the art will recognize, or be able to ascertain, using no more than routine experimentation, numerous equivalents to the specific substances and procedures described herein.

EXAMPLES

Example 1

This Example discusses the design and testing of liposomal azithromycin for post-myocardial infarction recovery. There is a growing body of evidence showing that altering the inflammatory response by alternative macrophage polarization towards the reparative phenotype is protective against acute ischemic injury and improves cardiac functional recovery. Research has shown that AZM, a macrolide antibiotic, alters inflammation and polarizes macrophages to the alternatively activated state in inflammatory conditions. The instant inventors have demonstrated that free AZM treatment (160 mg/kg/day, orally), initiated 3 days pre-MI, enhances post-MI cardiac recovery as a result of shifting macrophages to the reparatory state. Due to the limited clinical translational perspective (pre-MI treatment and relatively high dose of AZM) of the initial proof-of-concept study, this study was planned using a liposomal formulation of AZM (Lazm) to achieve rapid onset of action via targeted accumulation in inflammatory phagocytes.

Materials and Methods

Study Design

Figure 1A:
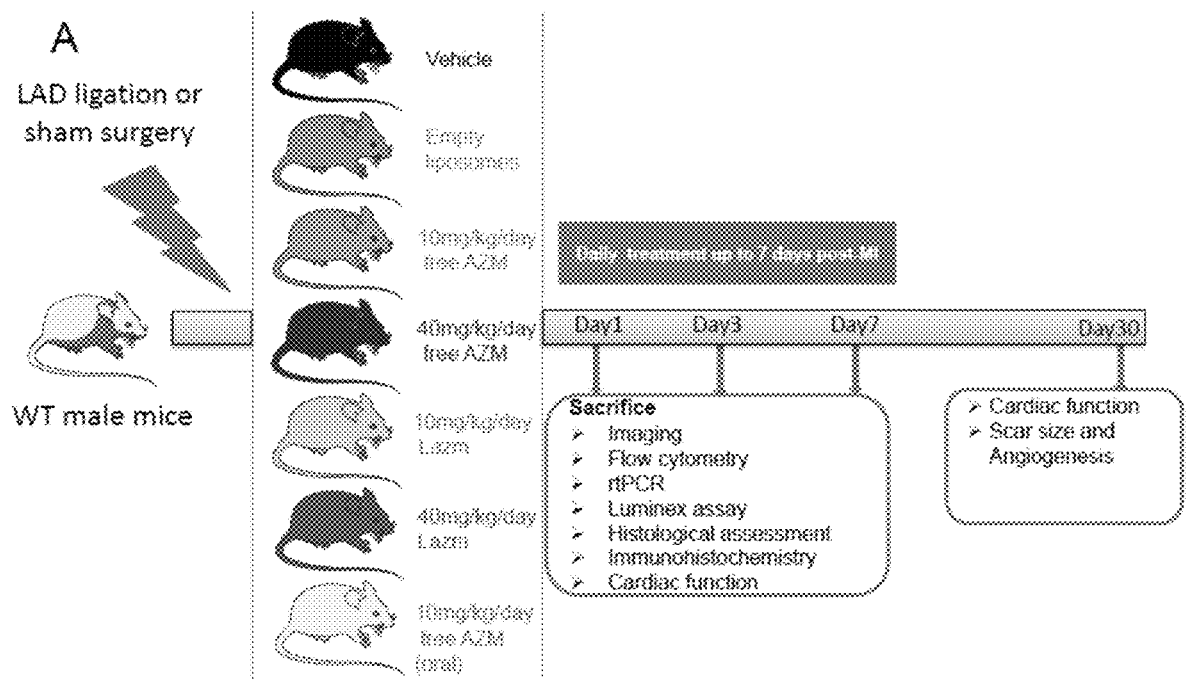
FIGS. 1A-C show experimental design targeting myocardium with labeled Lazm after infarction. (A) Experimental design for the in vivo study. (B) Maestro images of mice (in vivo) injected with labeled Lazm 1, 2, 3, and 6 days after infarction. Hearts were collected 24 hours after injection and imaged (ex vivo). Images show that Lazm liposomes accumulate in the heart starting the first day after infarction, an effect persisting through the time of follow-up (6 days). No signal was determined from the heart of the mouse with sham surgery either in vivo or ex vivo. The ex vivo imaging shows that liposomes preferably accumulate in the infarct and peri-infarct regions of the heart (red arrow). (C) Representative quantitative assessment of signal intensity emitted from the infarcted heart day 1, 2, 3, and 6 after infarct, which shows a marked increase in the intensity of the signal during all time points, in comparison to the control (a mouse injected with vehicle). Lazm, liposomal azithromycin.

C57BL/6 male mice (Jackson Laboratory, BarHarbor, Me.), age 6-8 weeks, were treated with two clinically-relevant low doses of liposomal or free AZM (10 mg/kg/day or 40 mg/kg/day) or vehicle (PBS or empty liposomes) using retro-orbital injection, starting immediately after MI or sham surgery for 7 days (FIG. 1A). Treatments were continued for 7 days to span the duration of the post-MI inflammatory period. All procedures were conducted under the approval of the University of Kentucky IACUC in accordance with the NIH Guide for the Care and Use of Laboratory Animals (DHHS publication No. [NIH] 85-23, rev. 1996).

Murine Model of Myocardial Infarction

Anesthesia was induced through a small animal vaporizer system with 1-3% isoflurane. Pain reflexes were appropriately tested to confirm adequate anesthesia before and during the surgical procedure. Lateral thoracotomy was performed between the left fourth and fifth ribs, the pericardial space was accessed, and the heart protruded from the intercostal space. The left anterior descending coronary artery (LAD) was identified and permanently ligated with 6-0 silk suture 3 mm distal to its origin, as previously described (Al-Darraji, Haydar et al. 2018). Sham surgery consisted of the same procedure without LAD ligation. The heart was immediately returned to the intrathoracic cavity and air was manually evacuated to prevent pneumothorax. Finally, the muscle and skin were sutured using a 4-0 Prolene running suture.

Preparation of Liposomes

Liposomal formulations were prepared according to previously established protocol (Kierstead, Okochi et al. 2015), using the thin film hydration method with equal molar ratios of distearyl phosphatidylcholine (DSPC), distearyl phosphatidylglycerol (DSPG) and cholesterol (Avanti polar lipids). AZM was included at 10 and 30 mol % based on phospholipid content. Formulations containing fluorophores were prepared in the same manner with 0.5 mol % of the lipophilic dye with 1,1'-dioctadecyl-3,3,3',3'-tetramethylindodicarbocyanine (DiD). Lipids and AZM were mixed in chloroform and methanol at the desired ratio and the organic solvents removed by rotary evaporation to yield a thin film. After placing under a vacuum overnight, the lipid/drug films were hydrated in phosphate buffered saline (pH 7.4) and sonicated at 65° C. for 30 min. The resulting unilamellar vesicles were extruded through 200 nm polycarbonate membranes to obtain uniform particle size. Liposome size, polydispersity and stability over time were determined by dynamic light scatter testing.

Flow Cytometry

Blood

Cell phenotype, in addition to gene analyses, of monocytes and neutrophils were investigated in peripheral blood as previously described (Al-Darraji, Haydar et al. 2018). Briefly, blood was collected in tubes with a 1:5 ratio of ethylene diaminetetraacetic acid (EDTA)/citrate-theophylline-adenosinedipyridamole (CTAD) on days 1, 3 and 7 post-MI. Whole blood was centrifuged for 5 minutes at 500×g, and the plasma layer was separated and reserved at −80° C. To lyse red blood cells, the residual cell pellet was incubated with 0.5 ml of diluted red blood lysing buffer (BD pharm lyse) for 10 minutes with mild agitation. To end the lysis process, 0.5 ml of staining buffer (5% goat serum, 0.05% sodium azide in phosphate-buffered saline) was added to the suspension of red blood cell lysed blood. Then, the suspension was centrifuged at 400×g for 5 minutes, and the supernatant was removed. This step was repeated if the red blood cells were still detectable in the cell pellet. White blood cell pellet was washed twice in staining buffer to remove any residual lysis buffer. After supernatant removal, the pellet was resuspended in a pre-determined volume of staining buffer and counted. Cells of each blood sample were divided into two parts depending on cell counting to have ~$10^6$ live (trypan blue-negative) cells in each part. One portion collected for surface marker staining, and the other part incubated with cell lysis buffer (Life technologies) to lyse cells for 10 minutes with multiple aggressive agitations, and then kept at −80° C. for further gene expression analysis. Cells for staining were incubated immediately with conjugated primary antibodies against PERCPCY5.5-conjugated Ly6G/C (BD Pharmingen), PECY7-conjugated F4/80 (Biolegend), brilliant violet 421-conjugated CD11b (Biolegend), APC-CY7-conjugated CD45 (Biolegend), and PE-conjugated CD115 (Biolegend) for 30 minutes on ice. Following incubation, cells were washed twice with staining buffer and analyzed by an LSR II (Becton Dickinson) in the University of Kentucky Flow Cytometry Core. Using unstained cells and single fluorescent controls, laser calibration and compensations were performed for all experiments. Monocytes with the $CD45^{hi}/CD115^{hi}/Ly6-C^{hi}$ profile were identified as classical (pro-inflammatory), while cells with these markers $CD45^{hi}/CD115^{hi}/Ly6-C^{lo}$ were identified as non-classical (anti-inflammatory). Neutrophils were identified as $CD45^{hi}/CD115^{lo}/Ly6-C/G^{lo}$.

Heart

Phenotypic cell analysis of macrophages and neutrophils and gene expression analysis was conducted in the heart as previously described (Al-Darraji, Haydar et al. 2018). Briefly, mice were sacrificed, and hearts were rapidly isolated and placed in ice cold PBS (VWR International). Using a razor blade, the heart was minced manually. After mincing, tissue was incubated with a Collagenase B (Roche, Indianapolis, Ind.) and Dispase II (Roche, Indianapolis, Ind.) mixture at 37° C. for 30 minutes, with gentle agitation every 5-10 minutes. Tissue digestion ceased using cold staining buffer and the suspension was placed on ice and filtered using a 70 μm cell strainer, followed by centrifugation at 400×g for 5 mins at 4° C. Supernatant was discarded and the pellet was resuspended in 0.3 ml of staining buffer. Individual heart cells were divided into approximately three equal portions depending on cell counting with ~$10^6$ live (trypan blue-negative) cells in each. Two portions were used for cell staining while the remainder was incubated with cell lysis buffer (Life technologies) using multiple aggressive agitations, for 10 minutes and reserved at −80° C. for further gene expression analysis. Cells for flow cytometry were incubated immediately with conjugated primary antibodies against FITC-conjugated Ly6G (BD Pharmingen), PE-conjugated CD206 (Biolegend), PECY7-conjugated F4/80 (Biolegend), brilliant violet 421-conjugated CD11b (Biolegend), brilliant violet 510-conjugated CD11c (Biolegend), APC-CY7-conjugated CD45 (Biolegend), or PERCPCY5.5-conjugated Ly6G/C (BD Pharmingen), PECY7-conjugated F4/80 (Biolegend), brilliant violet 421-conjugated CD11b (Biolegend), APC-CY7-conjugated CD45 (Biolegend), and PE-conjugated CD115 (Biolegend) for 30 minutes on ice. Cells were then washed twice with staining buffer and analyzed by an LSR II (Becton Dickinson) in the University of Kentucky Flow Cytometry Core. Using unstained cells and single fluorescent controls, laser calibration and compensations were performed for all experiments. $CD45^{hi}/Ly6G^{lo}/F4-80^{hi}$ cells were identified as macrophages and further classified as pro-inflammatory or reparative based on the expression of CD206 and CD11c. Neutrophils were defined as $CD45^{hi}/CD115^{lo}/Ly6-C/G^{lo}$, CD206 was used to further identify N1 neutrophils.

Histology

Histological analysis was performed on deparaffinized and rehydrated sections as previously described (Al-Darraji, Haydar et al. 2018). Briefly, 30 day post-MI mice (N=6-10/treatment group) were sacrificed under isoflurane anesthesia and hearts were isolated. Hearts were perfused with PBS (VWR International) then by 10% buffered formalin (VWR International) at 75 mmHg. Perfused hearts were placed in 10% neutral buffered formalin (VWR) overnight at room temperature, then sectioned into 2-mm cross-sections starting at the level of coronary ligation then imbedded in paraffin and sectioned into 4-μm sections. Sections were stained with Masson's trichrome to evaluate scar size as previously described (Al-Darraji, Haydar et al. 2018). Digital images of stained sections were acquired, and areas of interest were assessed using NIH ImageJ (version 7) software. The LV area, LV cavity area, and infarct area were measured as previously described (Al-Darraji, Haydar et al. 2018). Scar size was presented as a percentage of the total LV volume.

Immunohistochemistry

Heart sections (N=4/treatment group) were prepared as described in the previous section. Immunostaining of heart sections was performed on deparaffinized and rehydrated sections as previously described (Al-Darraji, Haydar et al. 2018). Briefly, after deparaffinization and rehydration, sections were incubated with primary antibodies: rabbit anti-mouse IBA1 (Wako), goat anti-mouse CD206 (R and D Systems), and goat anti-mouse IL-1β (R & D Systems) overnight at 4° C., then washed and incubated with secondary antibodies conjugated to Alexa Fluor 488 or 594 (Invitrogen), followed by incubation with DAPI. In the peri-infarct area, 10-15 adjacent zones per section (1-2 sections/animal) were imaged at 40× magnification utilizing Nikon Confocal Microscope A1 in the University of Kentucky Confocal Microscopy facility. Nucleated cells that were antibody-positive were quantified using Cell Counter plugin for Nikon NIS-Elements (version AR 3.2). Findings are presented as total number of positive cells per high power field in the area of interest.

By using a similar protocol to the above, heart sections (N=5-7/treatment group) were prepared from mice sacrificed at day 30 post-MI. Sections were stained with FITC-conjugated isolectin B4 (FL1201, Vector Labs, Burlingame, Calif.). In the peri-infarct region, 10-15 adjacent zones per section (1-2 sections/animal) were imaged at 40× magnification utilizing Nikon Confocal Microscope A1. Quantification was performed using Cell Counter plugin for Nikon NIS-Elements (version AR 3.2). Findings are presented as total capillary density per $mm^2$ in the peri-infarct zone. All measurements were performed in the peri-infarcted areas only and analyzed by blinded observer.

Cell apoptosis was examined on deparaffinized and rehydrated sections from mice (N=4/treatment group) sacrificed at day 3, as previously described (Al-Darraji, Haydar et al. 2018). TUNEL and caspase-3 staining was performed in the Biospecimen Procurement and Translational Pathology Shared Resource Facility (BPTP SRF) at the University of Kentucky. Nucleated cells that stained positive were estimated. Quantification was performed using Cell Counter plugin for ImageJ (version 1.51d). Findings are presented as total positive cells per high power field in the peri-infract region. All measurements were obtained in the peri-infarcted areas only and analyzed by blinded observer.

Reverse Transcription Polymerase Chain Reaction (RT-PCR).

PureLink RNA Mini Kit (ThermoFisher Scientific) was used to isolate total mRNA from heart and blood cells according to manufacturer protocol. Isolated RNA was quantified using NanoDrop 8000 spectrophotometer (Thermofisher). Next, cDNA was generated using SuperScript VILO cDNA synthesis kit (Invitrogen). Using a QuantaStudio 7 Flex real-time thermocycler (Applied Biosystems by life technology), Reverse Transcription-Polymerase Chain Reaction (RT-PCR) was performed to measure the mRNA expression of markers identifying: inducible nitric oxide synthase (iNOS), tumor necrosis factor alpha (TNF-α), monocyte chemotactic protein-1 (MCP-1), transforming growth factor beta (TGF-β), interleukin-1 beta (IL-1β), interleukin-6 (IL-6), interleukin-4 (IL-4), chitinase-like3 Chil3 (YM1), interleukin-10 (IL-10), arginase-1 (ARG-1), and Peroxisome proliferator-activated receptor gamma (PPARg). We used the comparative Ct method for relative estimation of mRNA expression which was normalized to 18 s (a housekeeping gene). Certain strategies to avoid bias and error inducible by contaminated DNA were taken: (a) Primers were adjusted to bridge an intron for specific cDNA augmentation, (b) Appropriate negative control reactions (template free controls) were used, (c) Careful examination of the melting curve of augmented products (dissociation graphs) for consistency was performed, and (d) The probe Tm was at least 10° C. more than the primer Tm, while the melting temperature (Tm) was 57° C.-60° C.

Echocardiography

Mice were anaesthetized using 1%-3% isoflurane during Echocardiography to maintain heart rate of 450-500 BPM during imaging. A Vevo 3100 system coupled with a 15-7-MHz linear broadband transducer and a 12-5-MHz phased array transducer was used to perform Echocardiogram analyses. Heart function was examined at baseline (before cardiac surgery) then one-week and 4 weeks post-MI. During acquisition, a heating pad was used to preserve the body temperature at 37° C.; the temperature was continuously assessed by a rectal temperature probe. Using modified parasternal long-axis and short-axis, two-dimensional and Doppler echocardiography was used to assess the LV function and volume in M-mode. Tracings at the mid-papillary level to investigate the systolic and diastolic parameters and Teichholz formula were used to quantify LV function. Echocardiography imaging and analyses were carried out by a blinded investigator.

Luminex Assay

At 1 and 3 days post-MI, plasma was collected using the PB collection protocol detailed earlier. Inflammatory biomarkers (IL-12, IL-1β, IL-1α ITNF-α, MIP-1, MIP-1α, MIP1β, MIP2, IP-10, LIX, G-CSF, RANTES, and KC) were quantified using the Milliplex mouse cytokine magnetic kit (MILLIPLEX MAP for Luminex xMap Technology, Millipore, USA) according to the manufacturer's protocol.

Maestro In Vivo Fluorescence Imaging

Mice were placed inside the Maestro imaging system under isoflurane anesthesia. They were positioned so that the chest and abdomen of the animal were in the field of view. We used an orange filter (excitation 605 nm, emission 675 nm long pass) to capture the APC signal that comes from liposomes. Acquisition settings were in range from 640 to 820 nm in 10-nm steps. To enhance the quality of the images we adjusted various variables like stage height, focus, and exposure length, within time points. Images were taken with side-by-side Lazm and vehicle-injected control animals and were analyzed using Maestro software (Cambridge Research & Instrumentation, INC. (CRI), USA).

Cell Culture

We used a murine macrophage cell line, J774 monocyte/macrophage cell line (ATCC, Manassas, Va.), for in vitro experiments examining the immunomodulatory effects of free and liposomal AZM. Using DMEM media (supplemented with 10% FBS, 1% penicillin/streptomycin, 1% sodium pyruvate, L-Glutamine, and Glucose), cells were plated in 6 well plates at a concentration of $0.3 \times 10^6$ cells/well. After adhesion, cells were treated with 30 µM free or liposomal AZM (Sigma-Aldrich, St. Louis, Mo.) and 20 ng/ml IFNγ (eBioscience 14-8311-63) diluted in DMEM. Following overnight incubation at 37° C. with 5% CO2, cells were stimulated using 100 ng/ml of LPS (Invivogen) diluted in DMEM. Supernatant was collected 48 hours after stimulation to quantify pro- and anti-inflammatory cytokine (TNF-α and IL-10) concentration.

ELISA Assays

Levels of TNF-α and IL-10 were assessed in the supernatant from in vitro cell culture experiments using standard ELISA kits (BD Biosciences, San Deigo, Calif.) according to the manufacturer protocol. Results are presented for each cytokine (picogram/ml) with different treatments.

Non-Invasive Electrocardiogram (ECG) System

Mice were anesthetized with 2% isoflurane, then placed on the ECG platform. Electrodes were inserted subcutaneously on the two front paws and the left rear paw followed by ECG recording for 2-3 minutes. Once the recording was completed, the data were analyzed using Chart software (PhysioTel).

Statistical Analysis

Data were presented as mean±standard error of the mean (SEM). Unpaired Student t test or analysis of variance (one-way or multiple comparisons) were used for group comparisons, as appropriate. Two-sided Dunnett or Dunn tests for post hoc multiple comparison procedures were used, with control samples as the control category. P value less than 0.05 was considered statistically significant during the analyses. Statistical analyses were performed using the Prism 8 software package (GraphPad, La Jolla, Calif.).

Results

We observed a significant shift favoring anti-inflammatory/reparatory macrophages with both AZM formulations (free and liposomal). Cardiac inflammatory neutrophils were also decreased with AZM treatment and was paralleled with significant reduction in the infiltration of inflammatory monocytes. Modulation of the inflammatory cell response was associated with significant reduction in pro-inflammatory and equivalent increase in anti-inflammatory gene expression. Taken together, AZM treatment induced a systemic shift in post-MI inflammatory response. AZM effects resulted in reduced cardiac cell death and scar size, and enhanced angiogenesis. These protective effects led to improved functional/structural complications post-MI. importantly, liposomal formulation of AZM is protective from its cardiac off-target effects.

Lazm Formulation Accumulates in the Injured Myocardium, Particularly in Immune Cells.

Figure 1B:
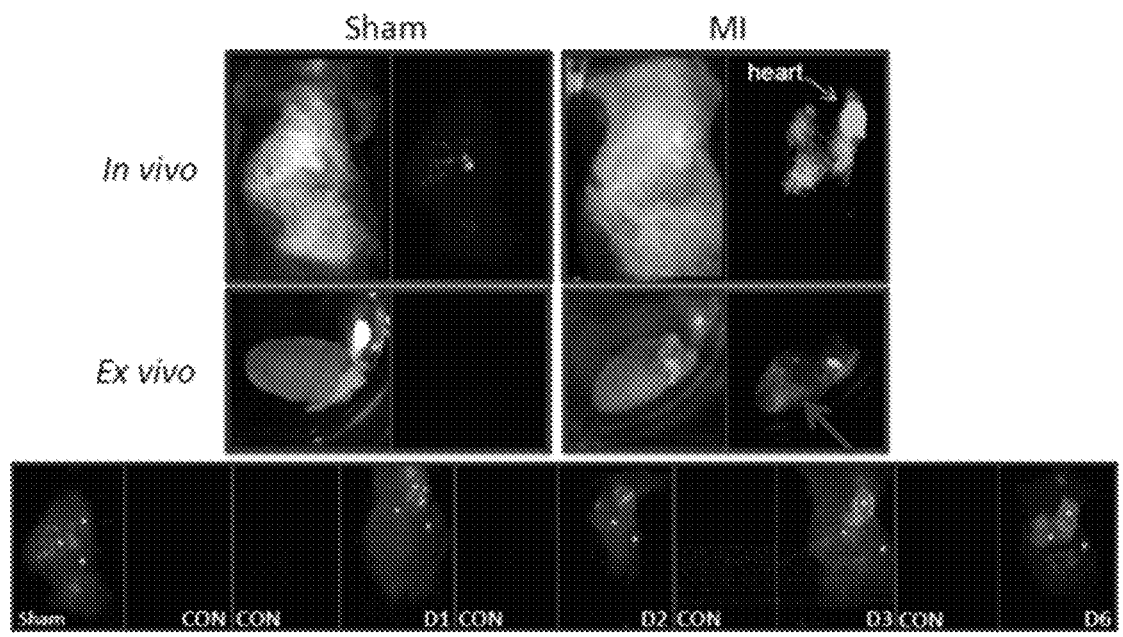
Figure 1C:
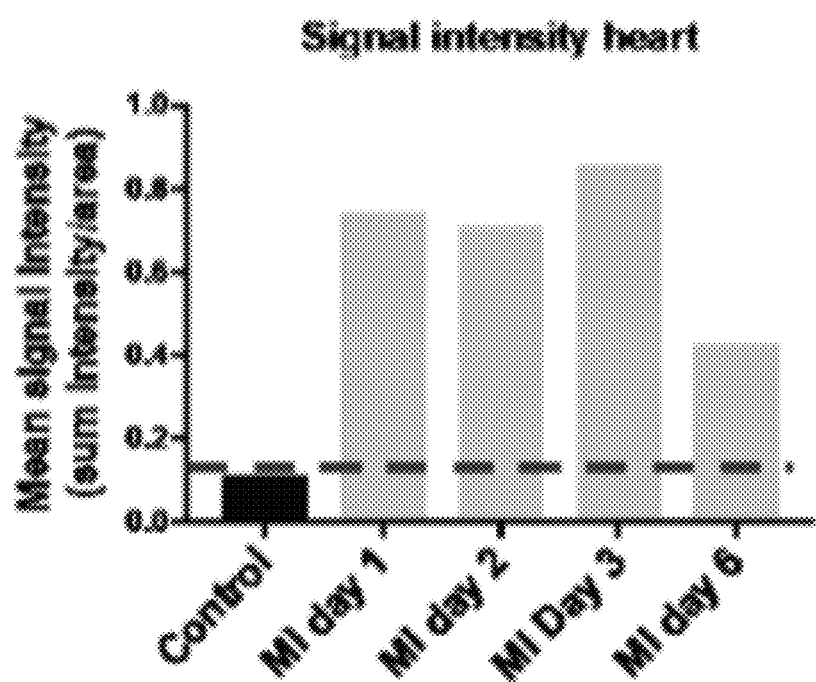

Several therapeutic agents have been tested to alleviate cardiac remodeling post-MI through systemic administration; however, they suffer limited efficacy due to poor bioavailability in the heart or dose-limiting adverse effects. The increased vascular permeability post-MI facilitates the accumulation of nanocarriers such as liposomes in the injured myocardium. In our studies, we elected to use non-PEGylated liposomes which are readily engulfed by phagocytes at sites of tissue injury. First, we were interested in determining whether Lazm accumulates in the injured heart after parenteral administration. A Maestro EX in vivo imaging system was utilized in combination with APC-labeled liposomes for visualization (FIG. 1B). We found that Lazm accumulates in the injured heart as early as the first day after infarct and peaks at day 3 after injury (FIG. 1C). The ex vivo imaging shows that these liposomes more likely accumulate in the infarct and peri-infarct regions of the heart, which is consistent with geographic accumulation of infiltrating phagocytes (FIG. 1B). Importantly, no signal was determined in the heart of sham operated mice either in vivo or ex vivo.

Figure 2:
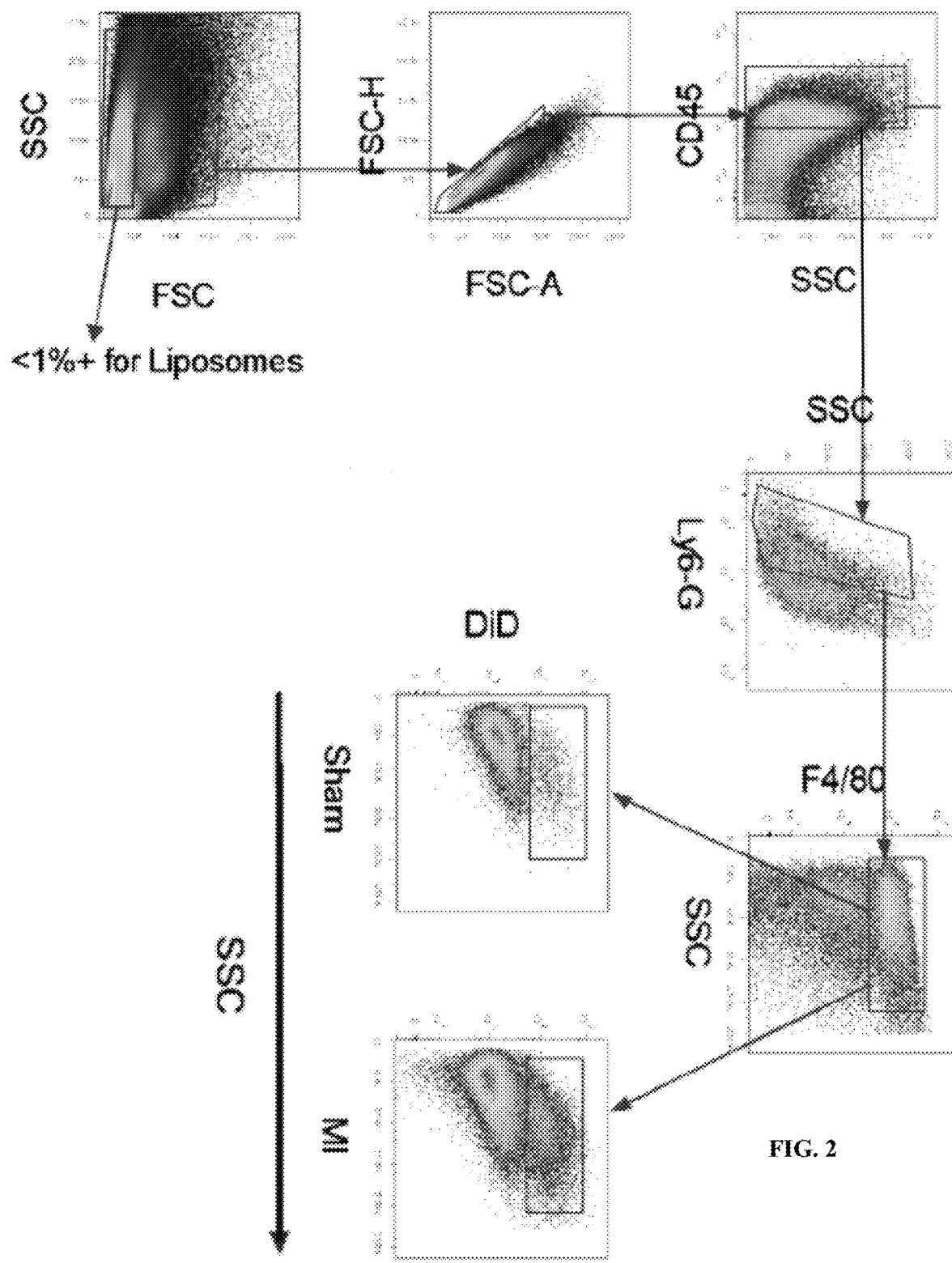
FIG. 2 shows graphs illustrating targeting of immune cells with labeled Lazm after infarction. FACS analysis with labeled Lazm at days 1 and 3 post-MI shows liposomes are accumulated in cardiac immune cells after IP or IV administration, with more significant effect after IV administration. Data suggests that Lazm liposomes begin to concentrate in the immune cells on day 1 post-MI using IV but not IP route. No significant accumulation was noted in non-immune cells (N=3 animals/group/timepoint, *P<0.05, P<0.01, and *P<0.001, and ****P<0.0001 compared to sham). Data presented as mean±SEM. IV, intravenous; IP, intraperitoneal; Lazm, liposomal azithromycin; Macs, macrophages; Control, mice did not receive liposomes.
Figure 3:
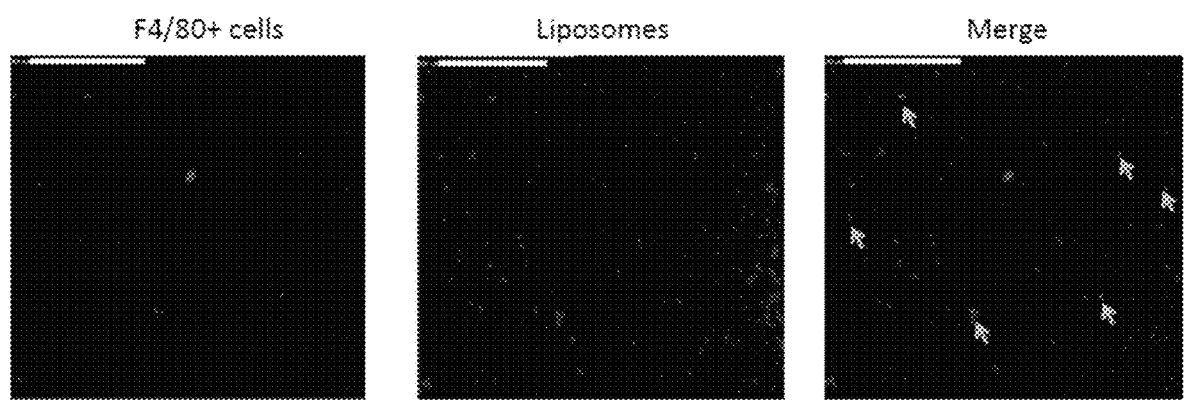
FIG. 3 shows images illustrating liposomes colocalizing with cardiac macrophages. Representative images from Celigo of heart cells of Lazm-treated mice show spatial localization of macrophages (orange) and liposomes (purple). Images show a remarkable localization of macrophages with liposomes. Lazm, liposomal azithromycin. In this experiment, a similar protocol to flow cytometry was used to prepare cell suspension; however, Celigo was used instead of flow cytometry to identify colocalization of different cell populations with liposomes (N=3 mice).

Post-infarcted myocardium contains diverse cell populations that may be targeted therapeutically to enhance cardiac recovery. Liposomal formulations have been extensively tested as targeted delivery tools for phagocytic cells, with lower immunogenicity, higher bioavailability and specificity, and greater drug stability. We examined liposomal accumulation in the heart at a cellular level using flow cytometry. FACS analysis of labeled Lazm shows that liposomes concentrate in phagocytes such as neutrophils and macrophages beginning on day 1 post-MI. Importantly, less than 1% of non-immune cells in the heart show liposomal uptake, implying preferential liposomal accumulation in the cells of interest (FIG. 2). These observations are confirmed using Celigo analyses which shows an enhanced liposomal colocalization with phagocytic cells isolated from the heart after MI (FIG. 3). These findings strongly indicate that our designed non-PEGylated liposomes accumulate at the peri-infarct region, particularly in phagocytic cells, early after MI. Liposomal accumulation exhibits temporal trends consistent with infiltration of inflammatory cells.

Hemodynamic Effects of Lazm.

Figure 4A:
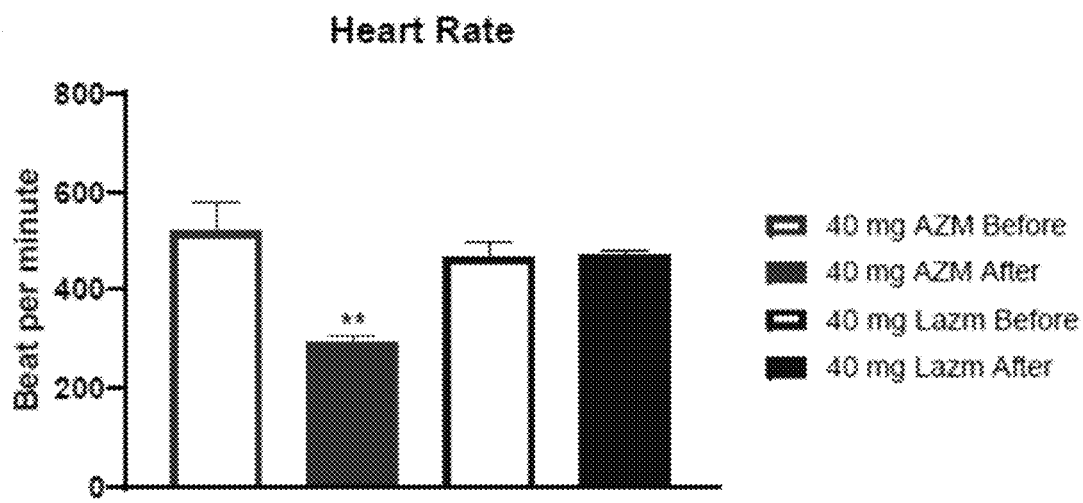
Figure 4B:
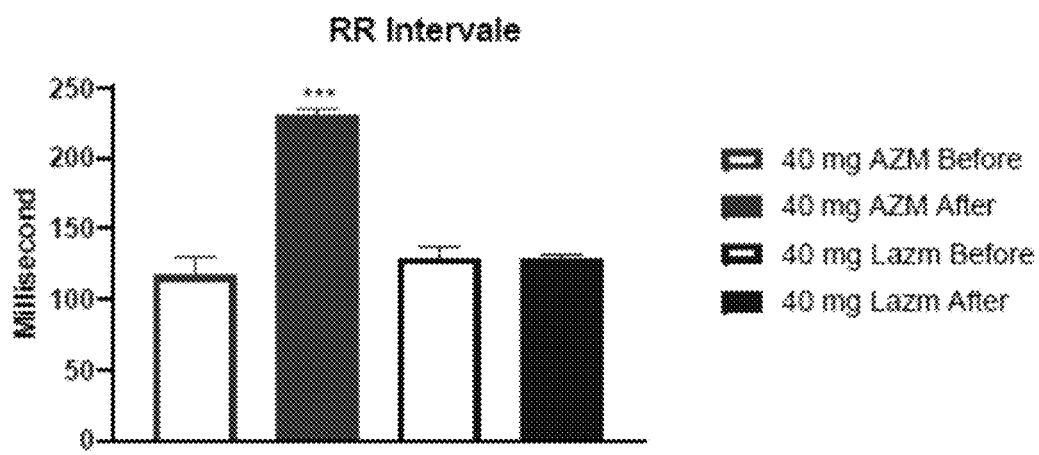

Studies show that AZM produces a negative inotropic effect and delays ventricular repolarization. These hemodynamic effects of AZM are probably mediated by a $Ca^{+2}$ channel-independent pathway and delayed rectifier K(+) current. Additionally, the cardiac action potential is much shorter in mice compared to humans. Therefore, we were interested in examining the potential arrhythmogenic and hemodynamic effects of AZM in the heart when administered post-MI. Baseline parameters were not different among the monitored groups. The retro-orbital administration of free AZM at 40 mg/kg remarkably reduces heart rate, RR, ejection fraction, and cardiac output interval compared with baseline (FIGS. 4A-E). Moreover, it is noted that the QT interval is also prolonged after free AZM administration (FIG. 4C). In contrast, administration of Lazm at the same dose does not induce any noticeable conduction or electrical changes in vivo (FIGS. 4A-C). These findings imply that the liposomal dosage form of AZM is indeed protective against hemodynamic drug modifications, which is most likely attributed to the specific delivery of AZM to immune cells, avoiding cardiomyocytes. It is likely that encapsulation of AZM rescues other adverse drug effects, making it an attractive method of delivery for clinical practice, especially in high risk patients.

Lazm Therapy Recruits Reparative Macrophages to the Infarcted Myocardium.

Figure 5A:
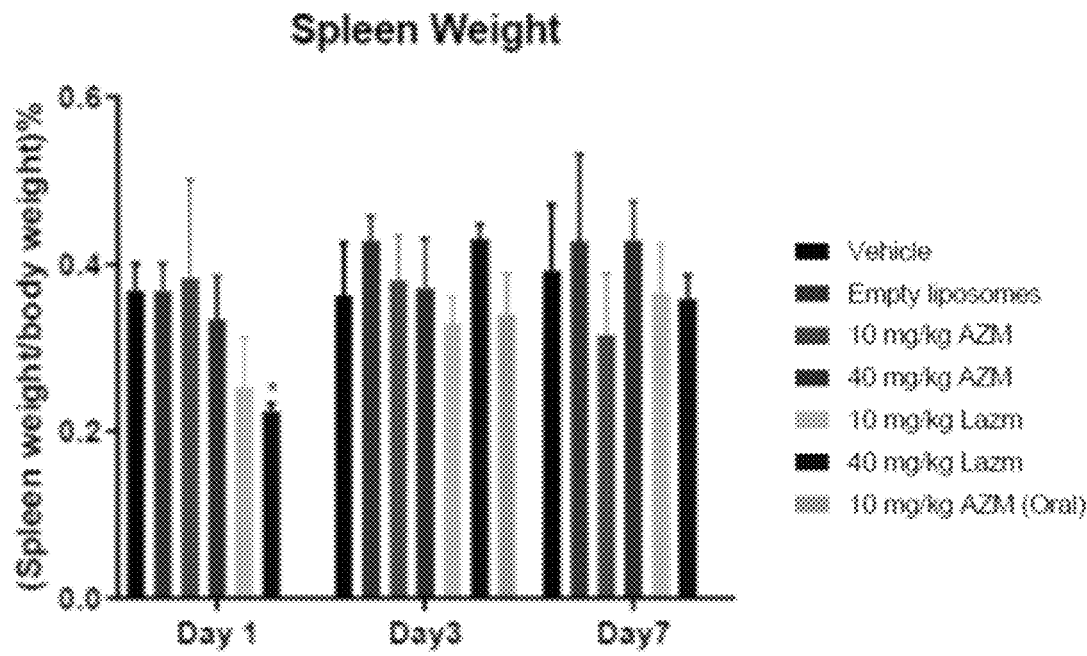
FIGS. 5A-B show graphs illustrating Lazm therapy rescuing heart and spleen from inflammatory induced hypertrophy. Quantitative assessment of (A) spleen and (B) heart as a percent of body weight suggests that Lazm therapy is protective against heart and spleen enlargement after infarction, indicative of less potent inflammation. (n=4 animals/group/timepoint, P*<0.05 and **P<0.01 compared to the vehicle control). Data presented as mean±SEM. AZM, azithromycin; Lazm, liposomal azithromycin; HT, heart.
Figure 5B:
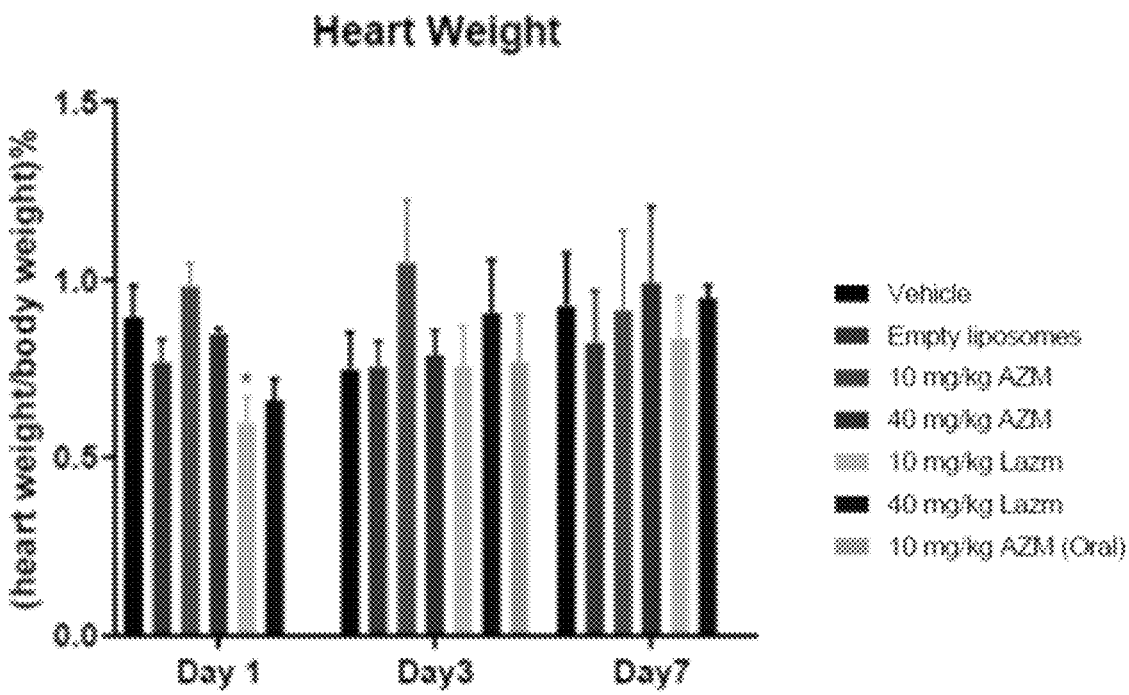
Figure 6A:
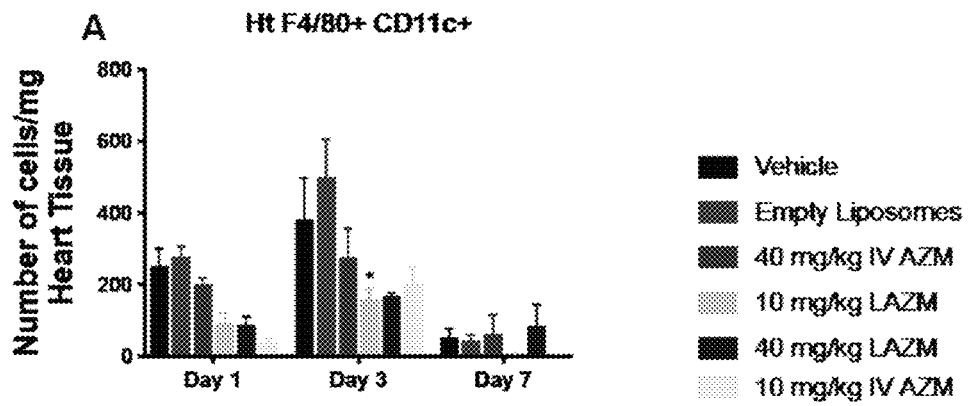
FIGS. 6A-C show graphs illustrating Lazm treatment shifting macrophages to the reparatory phenotype in the injured myocardium. Immunomodulation of macrophages by Lazm in heart tissue post-MI. FACS analyses for the relative expression of macrophage markers to assess their activation state in vehicle, free AZM, and Lazm treated groups. (A) Quantitative data suggests that inflammatory (F4/80+/CD11c+) macrophages markedly decrease in Lazm treated groups relative to controls starting at day1, with more profound effect on day 3 post-MI. (B) In contrast, the reparatory macrophages (CD206+) increase significantly at day 3 post-MI in the same groups of mice. (C) The immunomodulatory effects translate into a substantial reduction in the pro-/anti-inflammatory (CD11c+/CD206+) ratio at all tested timepoints post-MI. Less powerful immunomodulatory changes were noted with free AZM treatments. (N=4 animals/group/timepoint, P<0.01, *P<0.001, and ****P<0.0001 compared to the vehicle control). Data presented as mean±SEM. AZM, azithromycin; Lazm, liposomal azithromycin; Ht, heart.
Figure 6B:
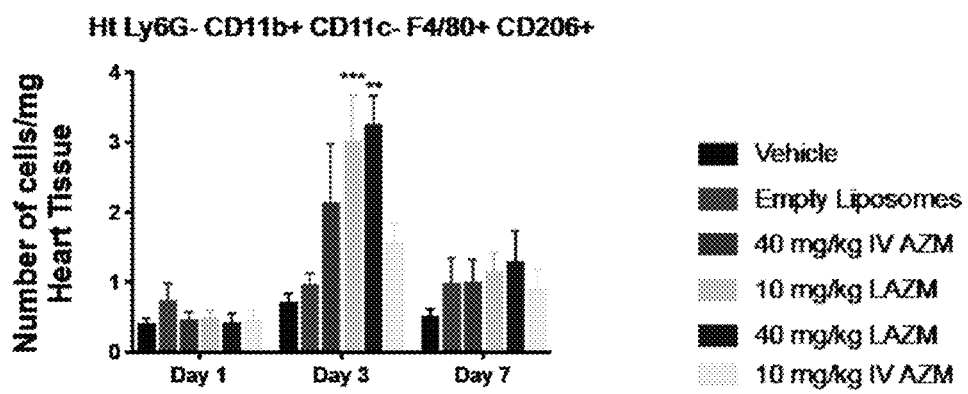
Figure 6C:
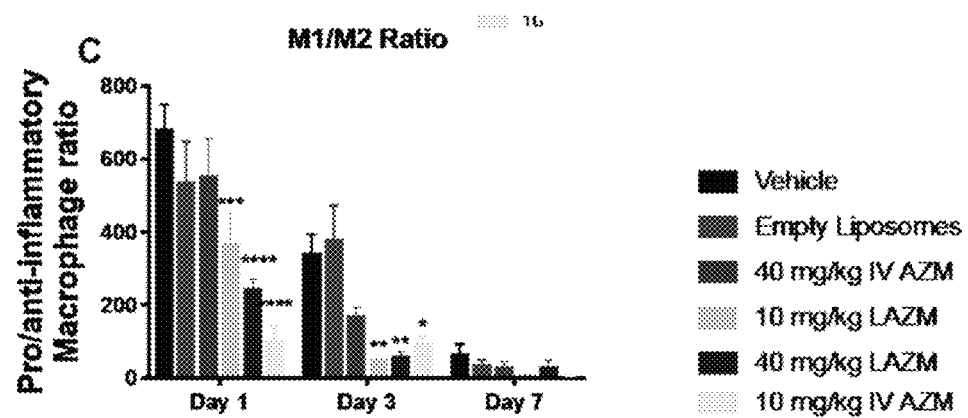

Macrophages are the primary cardiac immune cells during steady state and after ischemic injury, where they organize the ensuing inflammatory and healing events. We previously identified a cardioprotecive role of oral free AZM in the setting of MI via its immunomodulatory effects on macrophages in post-MI inflammation. However, the pre-MI administration and high dose of AZM limit the clinical translation of this previous study. Therefore, we used an encapsulated dosage form in an attempt to promote early cardiac bioavailability of AZM therapy. This is the first study to examine the anti-inflammatory and immunomodulation properties of liposomal AZM, which may potentially expand to other inflammatory pathologies. First, we find significantly lower heart weight in Lazm treated groups, suggestive of less tissue edema and potentially less inflammatory change (FIGS. 5A-B). In our investigation of macrophage phenotypes in the injured heart at multiple timepoints after injury using flow cytometry (FIGS. 6A-C), we observe a decrease in pro-inflammatory macrophages (CD45$^+$/Ly6G$^-$/F4-80$^+$/CD11c$^+$) at day 1 with a more profound effect on day 3 post-MI in Lazm treated groups compared to free AZM and control groups (FIG. 6A). Conversely, reparative macrophages (CD45$^+$/Ly6G$^-$/F4-80$^+$/CD11c$^-$/CD206$^+$) are significantly increased at day 3 in Lazm treated groups compared to free AZM and control groups (FIG. 6B). Collectively, these changes translate into a significant reduction in the ratio of pro-/anti-inflammatory macrophages in Lazm groups, indicating a shift in macrophage phenotype towards the reparative state (FIG. 6C).

Figure 7A:
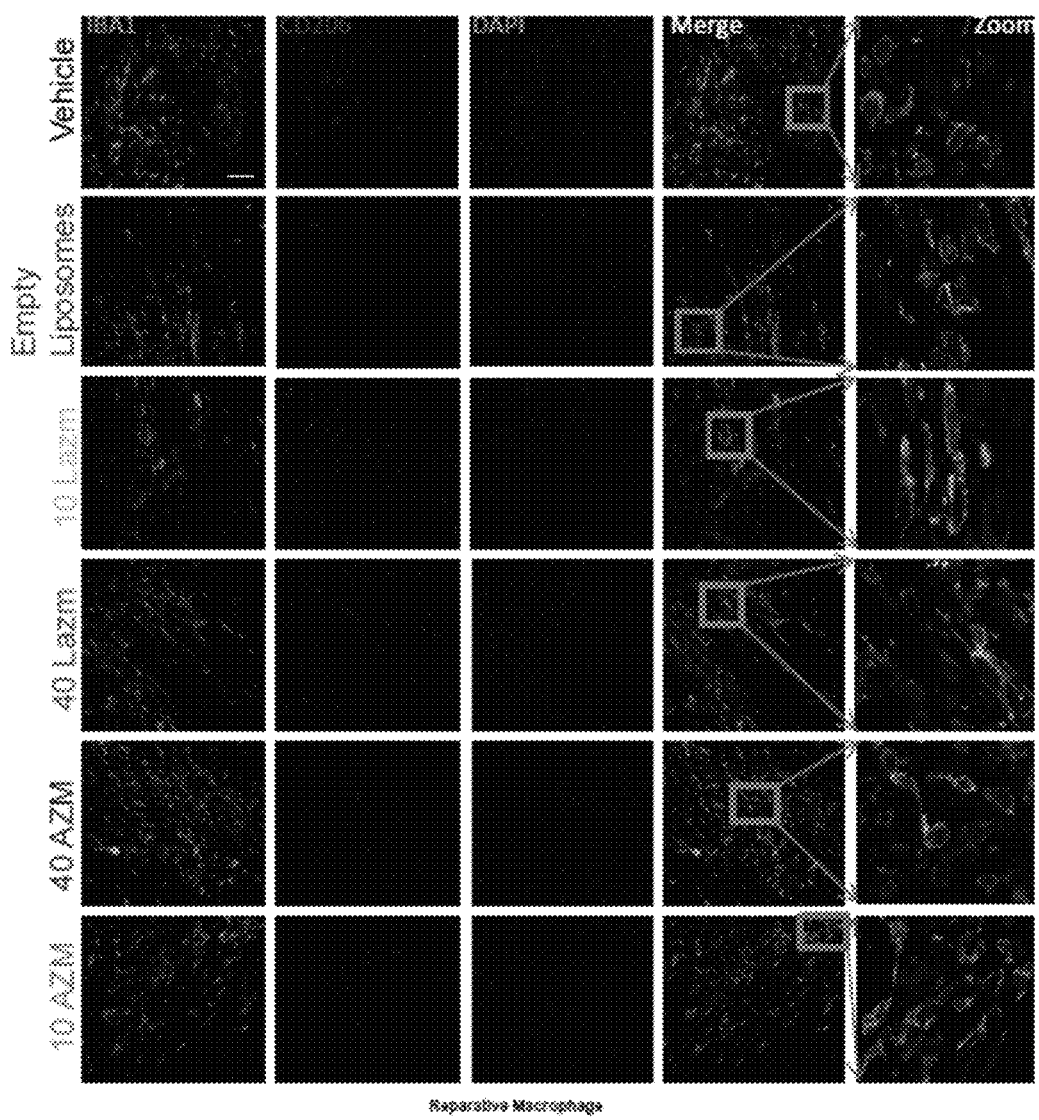
FIGS. 7A-B show images and graphs illustrating Lazm shifting macrophages towards the reparative phenotype in the ischemic heart. Immunohistochemical assessment of general and reparative macrophages (IBA1$^+$ and CD206$^+$, respectively) 3 days post-MI. (A) shows representative images from controls, free AZM, and Lazm treated mice illustrating IBA1 (green) and CD206 (red) positive macrophages in peri-infarct zones. Images show increased expression of CD206 by macrophages in free and liposomal AZM treated groups compared to controls. (B) represents quantitative assessment of IBA1 and CD206 3-days post-MI (n=4 animals/group, *P<0.001 and **P<0.0001 compared to vehicle control). Scale bars represent 50 µm. Data presented as mean±SEM. AZM, azithromycin; Lazm, liposomal azithromycin.
Figure 7B:
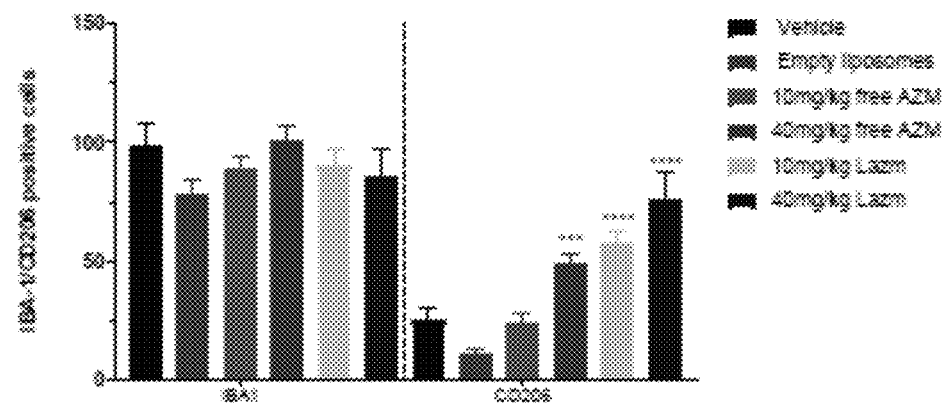
Figure 8A:
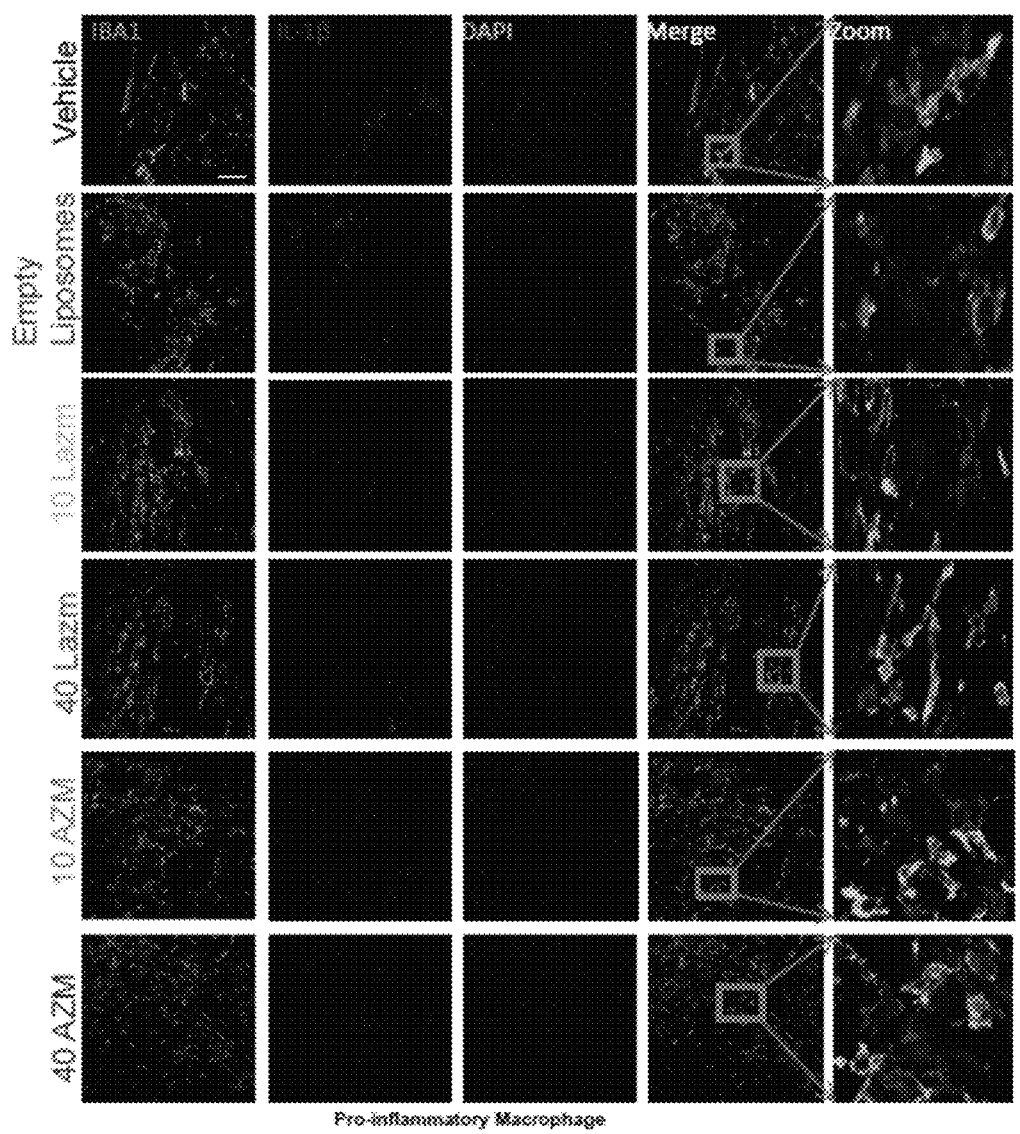
FIGS. 8A-B show Lazm reduces pro-inflammatory macrophages in the ischemic heart. Immunohistochemical assessment of a general macrophage marker (IBA1) co-localized with a pro-inflammatory cytokine (IL-1β) 3 days post-MI. (A) shows representative images from controls, free AZM, and Lazm treated mice illustrating IBA-1 (green) and IL-1β (red) positive macrophages in peri-infarct zones. Images indicate a marked reduction in the expression of IL-1β in macrophages with free and liposomal AZM treatments compared to controls. (B) represents quantitative assessment of IBA-1 and IL-1β 3-days post-MI (n=4 animals/group, *P<0.05 P<0.01, and **P<0.0001 compared to vehicle control). Scale bars represent 50 µm. Data presented as mean±SEM. AZM, azithromycin; Lazm, liposomal azithromycin.
Figure 8B:
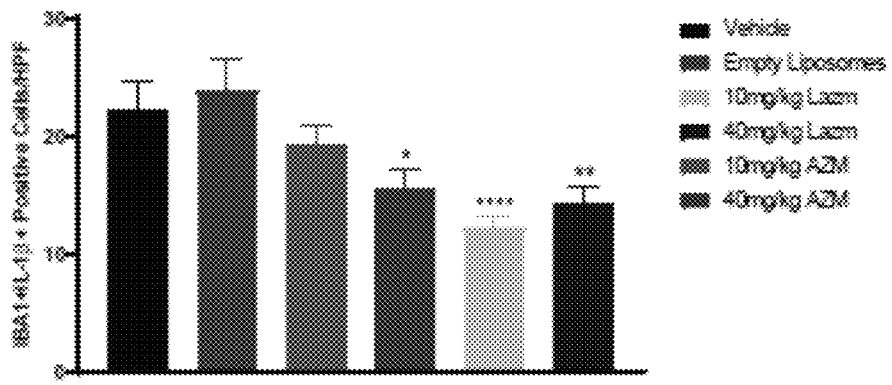

Repolarizing macrophages towards the anti-inflammatory activation state in peri-infarct zones can protect more cardiomyocytes from death, reducing infarct expansion and the subsequent adverse cardiac remodeling. To confirm the immunomodulatory effects of AZM on macrophages in the peri-infarct zone, we quantified cells expressing a general macrophage marker (IBA1), a reparative macrophage marker (CD206$^+$), and IL-1β s a marker of pro-inflammatory macrophages on day 3 post-MI using immunohistochemistry. We found a significant increase in reparative macrophages (CD206$^+$) in free and liposomal AZM treated mice compared to control groups (FIG. 7A). At the same time, we observe significantly higher numbers of pro-inflammatory macrophages (IBA1$^+$IL_1β$^+$) in the control groups (FIG. 8A). Generally, the total number of macrophages (IBA1$^+$ cells) were not different between groups, implying that Lazm therapy does not affect total macrophage count, but rather influences polarization in favor of the reparative phenotype, and the effect is increased with liposomal AZM (FIG. 7B). This observed shift in alternatively activated macrophages in AZM treated groups is observed in both our immunohistochemical and flow cytometric data. These effects may be therapeutically harnessed to resolve the detrimental inflammation post-MI.

Figure 9A:
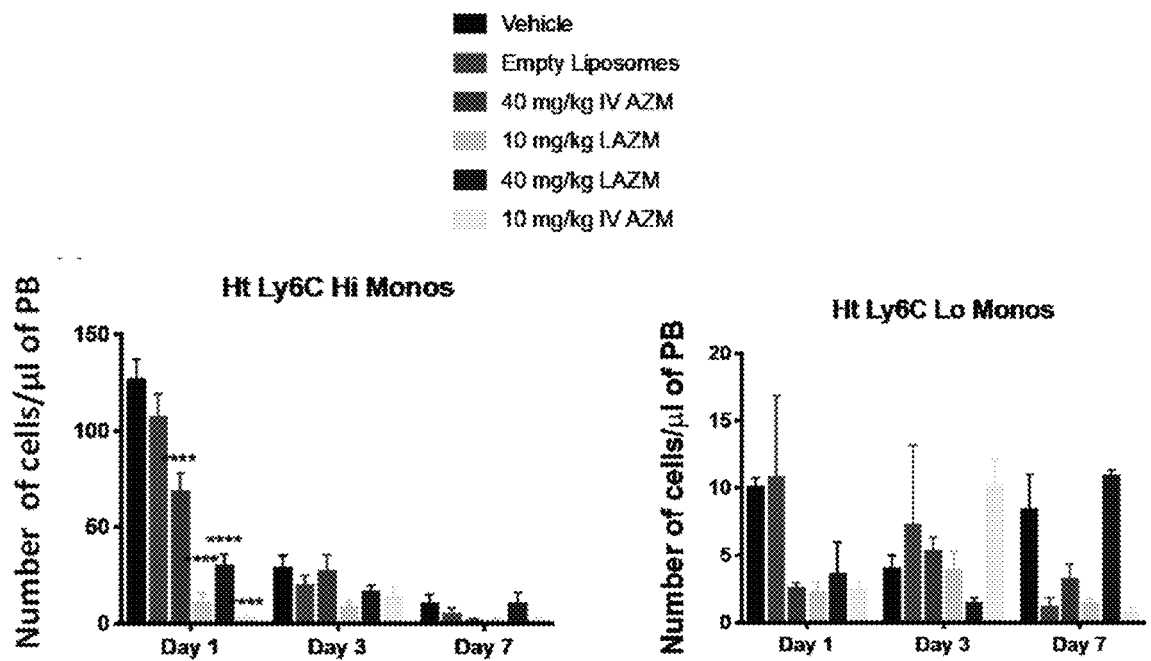
FIGS. 9A-B show graphs illustrating Lazm reducing inflammatory monocytes after infarct. Immunomodulation of monocytes by free and liposomal AZM in Ht and blood post-MI. FACS analyses for the relative expression of Ly6C to assess monocyte activation states in controls, free AZM, and Lazm treated groups of mice. (A) Quantitative data indicate that inflammatory monocytes (Ly6C$^{Hi}$) markedly decrease in liposomal and free AZM treated mice, with a more powerful effect in Lazm groups. (B) Very little change was noted in the blood. (N=4 animals/group/time point.
Figure 9B:
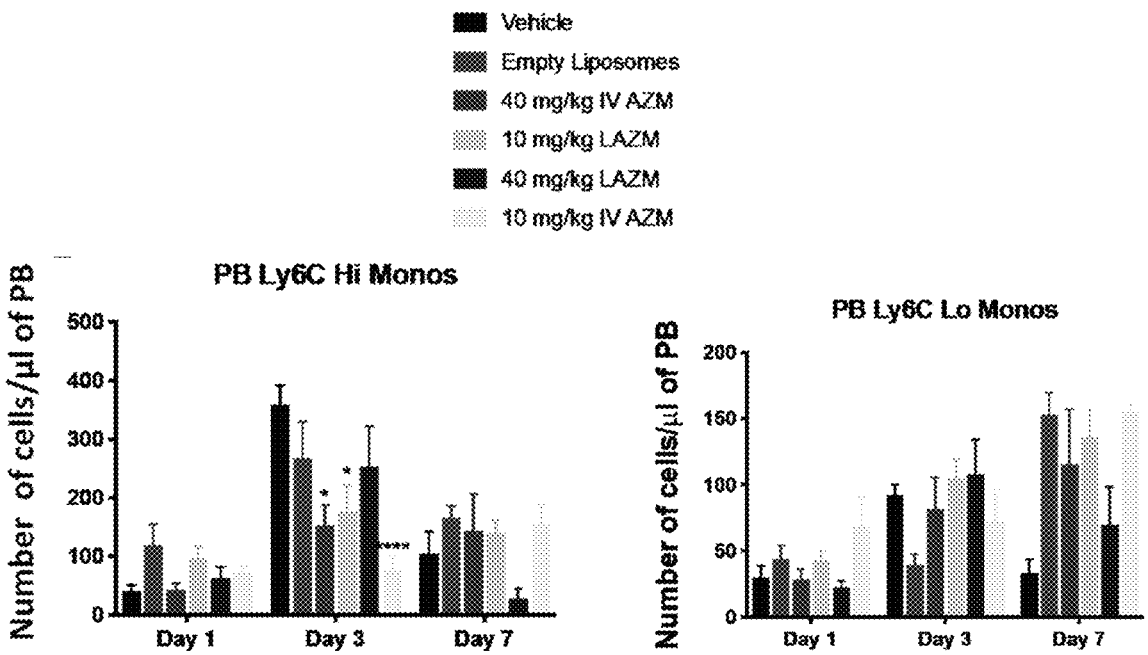

Monocytes dominate the infarcted heart following MI, providing a rich source of macrophages. Recruitment of the two subsets of monocytes (Ly6C$^{hi}$ and Ly6C$^{lo}$) to the heart occurs in two waves. These subpopulations mediate essential activities in early inflammation and the later reparative process. In the heart (FIG. 9A), we find that the Ly6C$^{hi}$ (CD45$^+$/Ly6C/G$^{hi}$/CD115$^{hi}$) monocytes (pro-inflammatory monocytes) significantly decrease in the first day after injury in liposomal and free AZM treated groups, an effect that disappears at later timepoints. In the blood (FIG. 9B), the Ly6C$^{hi}$ monocytes were considerably low on day 3 with comparable numbers on other days in the Lazm groups. These observations suggest that the liposomal and free AZM treatments can modulate other members of the immune response to MI both locally in the heart and systemically.
Lazm Treatment Reduces Neutrophils, Particularly N1.

Neutrophils orchestrate the clearance of dead cells and debris. Additionally, apoptotic neutrophils initiate anti-inflammatory changes in macrophages and hence contribute to the resolution of inflammation. Neutrophil (CD45$^+$/CD115$^{lo}$/Ly6G/C$^{lo}$) analysis in the heart and blood using flow cytometry reveals that Lazm treatment significantly reduces neutrophil counts during their peak at day 1 (FIG. 10A). However, we did not see significant changes in mice treated with free AZM.

To further investigate the immunomodulatory actions of AZM, we examined the distribution of N1 neutrophils (CD11b$^+$/Ly6G$^+$/CD206$^-$) in the heart over time (FIG. 10B). We find a substantial decrease in N1 neutrophils at day 1 Lazm treated groups (FIG. 10C), which may explain the reduction in total neutrophil number. These findings may represent a novel therapeutic avenue in the treatment of MI patients who experience prolonged neutrophilia after infarct.
Lazm Treatment Shifts Inflammatory Gene Expression Towards the Anti-Inflammatory State.

The gene expression profile of macrophages relates to the activation status of these cells. Pro-inflammatory macrophages produce large amounts of pro-inflammatory cytokines (IL-1β, TNF-α, IL-6) and toxic effector molecules (reactive oxygen species, nitric oxide). On the other hand, reparative macrophages are potent generators of anti-inflammatory cytokines (TGF-β and IL-10) in addition to the expression of scavenger, mannose, and galactose-type receptors. To identify whether liposomal formulation enhances the anti-inflammatory effects of AZM, we conducted in vitro experiments to identify the production of pro-inflammatory/anti-inflammatory cytokines in the J774 macrophage cell line. After 48 hours of stimulation, we observed accentuated immunomodulatory effects with liposomal AZM, confirmed through significant shift in the production of TNF-α and IL-10 towards the anti-inflammatory pattern (FIGS. 11A-B).

Figure 12A:
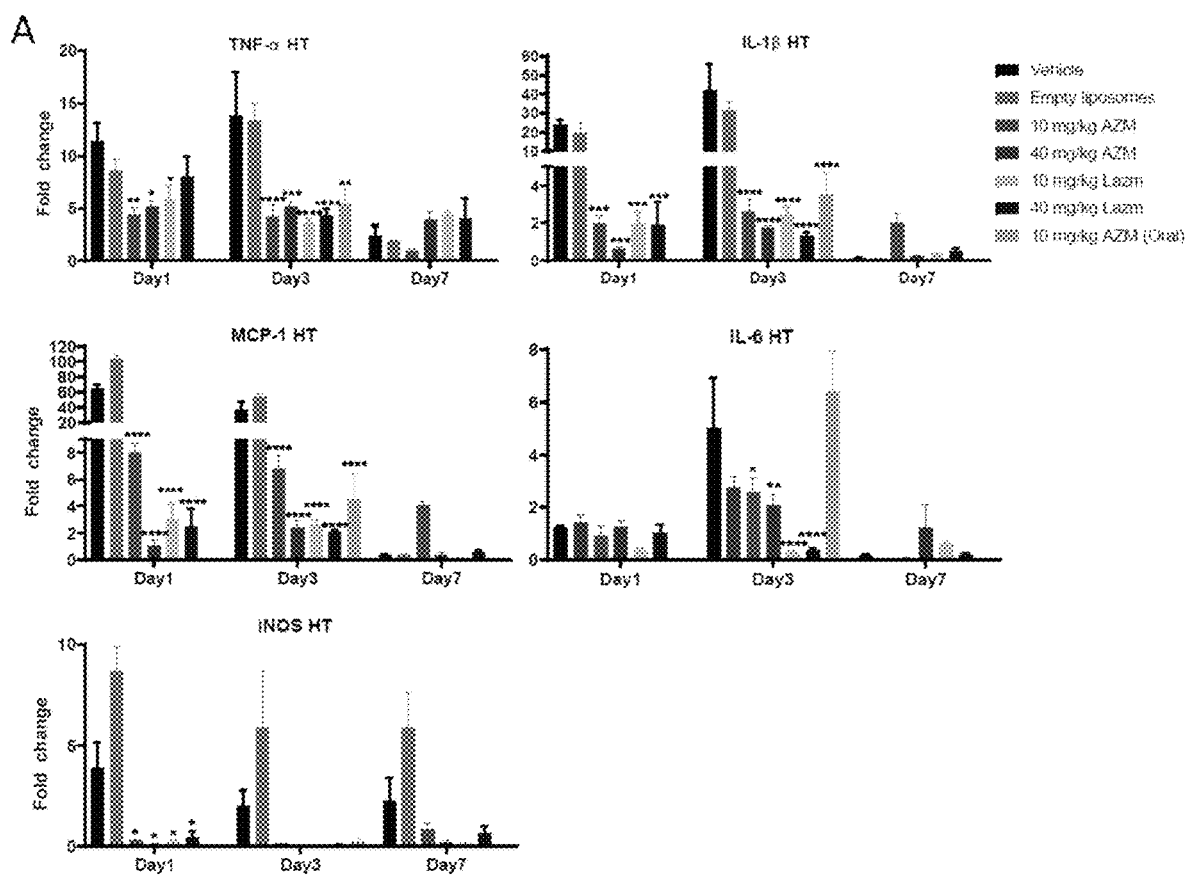
Figure 12B:
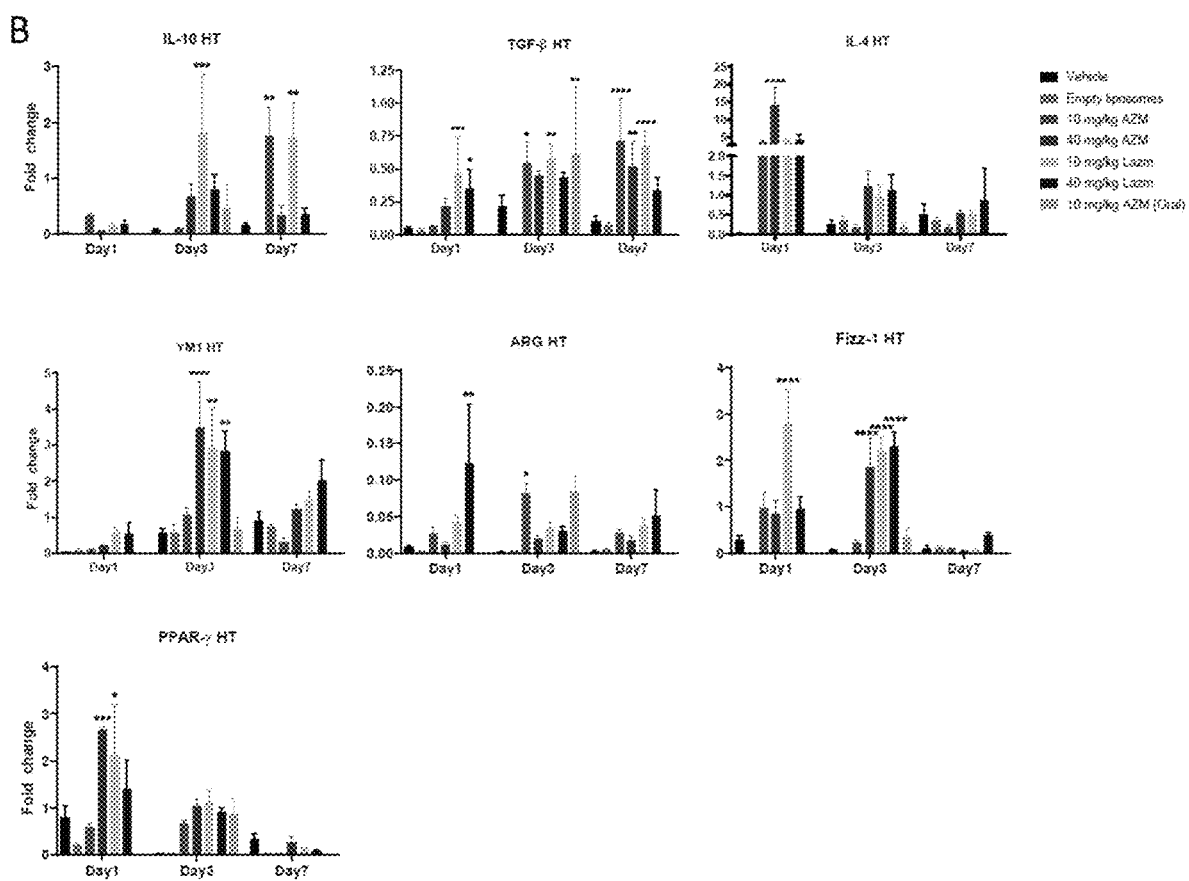
Figure 12C:
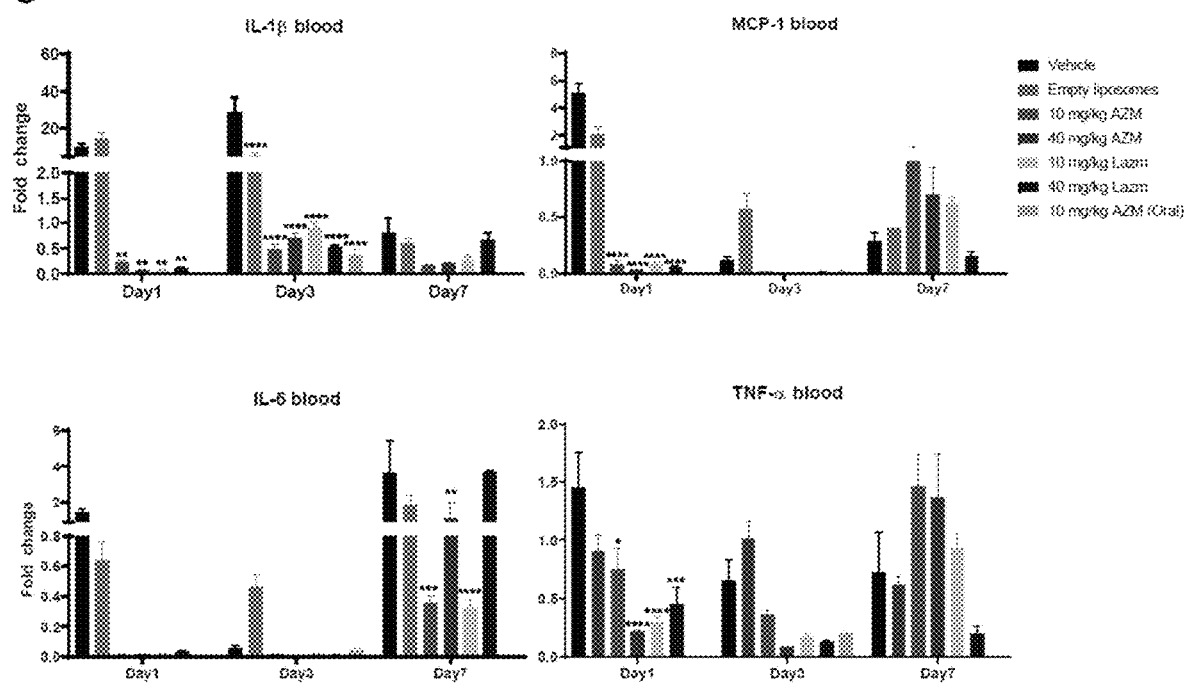
Figure 12D:
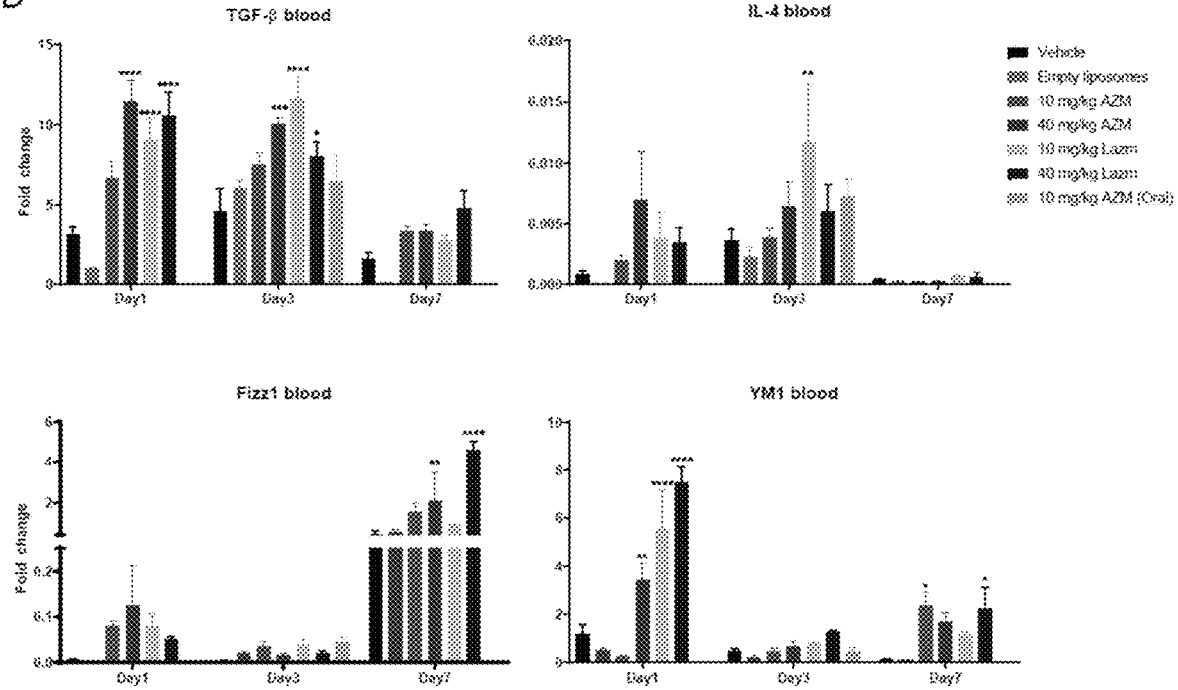

We also assessed the mRNA expression of inflammatory and reparative genes in the heart and blood cells using RT-PCR. We observed a significant shift in the gene expression profile towards the anti-inflammatory state associated with liposomal/free AZM treatment. In cardiac tissue, mRNA levels of iNOS (pro-inflammatory macrophage marker) and pro-inflammatory cytokines (MCP-1, TNF-α, IL-6, and IL-1β) are substantially downregulated in mice treated with free and liposomal AZM, particularly on days 1 and 3 post-infarct (FIG. 12A). Conversely, the expression of anti-inflammatory cytokines and reparative macrophages (TGF-β and IL-10, IL-4, ARG, Fizz1, PPARγ and YM1) are significantly upregulated in the same groups of mice with consistent effects up to day 7 (FIG. 12B). Interestingly, we observe a similar trend in the gene expression of cytokine and macrophage markers in PB cells in the same groups (FIGS. 12C-D), suggesting systemic anti-inflammatory and immunomodulatory effects of Lazm therapy in addition to local effects at the site of injury. Additionally, we observe that inflammatory cytokine and chemokine (IL-12, IL-1β, IL-1α ITNF-α, MIP-1, MIP-1α, MIP1β, MIP2,IP-10, LIX, G-CSF, RANTES, and KC) concentrations are reduced in plasma of AZM treated groups (FIG. 13). Based on our prior published studies, we see no changes at day 7 so we did not run that analysis. Collectively, these consistent results from multiple in vitro and in vivo studies suggest that AZM may have therapeutic clinical potential in MI patients.
Lazm Therapy Reduces Cell Death and Scar Size, and Increases Angiogenesis in the Infarcted Heart.

To identify the pro-survival effect of AZM therapies on cardiac cells post-MI, we assessed apoptosis in peri-infarct borders 3 days post-MI using caspase-3 (early apoptosis) and TUNEL (late apoptosis) assays. We observed that free and liposomal AZM therapy markedly reduce apoptosis in comparison to controls (FIGS. 14A-15B), likely related to pro-survival factors produced by reparative macrophages. We next assessed the infarct size 30 days post-MI using Masson's trichrome-stained sections from the heart. We found that Lazm treatment significantly reduces scar size in comparison to controls (FIGS. 16A-B). These data indicate that AZM preserves the heart from acute injury after ischemia as well as reduces susceptibility to chronic scar enlargement.

Reparative macrophages, through secretion of protective cytokines and pro-angiogenic factors such as VEGF, may promote reparative power. To determine blood vessels density at the infarct borders, we quantified isolectin-positive cells (a marker for endothelial cells) in the peri-infarct region 30 days post-MI. We observe a significant increase in density of newly formed blood vessels in the Lazm groups compared to controls (FIG. 17A-B). This is another important factor in AZM/Lazm therapy that may contribute to reduced scar size. The shift in macrophage phenotype may explain the reduction in apoptotic cells and enhanced angiogenesis and provide the mechanism for reduced scar size observed in these groups.

Lazm Therapy Enhances Cardiac Functional Recovery after MI.

Adverse cardiac remodeling and the ensuing heart failure post-MI are likely related to an imbalance between pro-inflammatory and pro-reparative phases after injury. By modulating the inflammatory response, we investigated the role of AZM in cardiac recovery after MI. We performed echocardiography at 1- and 4-weeks post-MI and analyzed cardiac function and remodeling. We observed a significant attenuation of LV functional decline in Lazm treated groups compared to controls (FIG. 18A). A similar trend was noted with other cardiac remodeling parameters such as LV end-systolic and LV end-diastolic diameters in the same groups (FIGS. 18B-C). Furthermore, we observed that the thickness of the infarcted wall was more preserved in Lazm treated groups (FIGS. 18D-E), which is consistent with our histological examination. Finally, survival rates indicate that the cardioprotective effects of AZM were translated into a remarkable reduction in mortality (FIG. 19).

Collectively, the immunomodulatory effects of Lazm therapy were potent at inducing favorable resolution of the overactive and/or extended pro-inflammatory cascades and their associated cardiac damage and impaired recovery. As a result, we found significant improvement in the the structural/functional complications post-MI.

Discussion

Macrophages are the primary immune cells in the heart post-MI, organizing the early inflammatory stage and the later reparative events. The two activation states of macrophages (pro-inflammatory vs. reparatory) make macrophages an attractive therapeutic target to induce earlier resolution of post-MI inflammation. We recently found that azithromycin (AZM) improves cardiac remodeling and recovery post-MI through shifting of macrophages to the reparatory state using a proof-of-concept experimental model. In this study, we utilized a clinically relevant experimental design using targeted liposomal AZM delivery to potentiate its bioavailability and immunomodulatory effects post-MI. Lazm enhanced resolution of post-MI inflammation as evidenced by a shift of pro-inflammatory to reparatory monocytes/macrophages. Neutrophils were substantially decreased as well, particularly the pro-inflammatory N1 neutrophils. These cellular changes were observed primarily at the site of cardiac injury and were paralleled by a shift towards anti-inflammatory cytokine production and cellular preservation, leading to reduced scar size, enhanced angiogenesis, and improved cardiac functional recovery. In addition to these findings, we observed that the liposomal formulation is protective from adverse drug effects such as conduction abnormality. These findings imply that low dose, post-MI treatment of Lazm is a promising therapeutic target in patients with MI.

Several therapeutic agents have been tested to alleviate cardiac remodeling post-MI through systemic administration, however; they had limited efficacy due to poor accumulation in the target site/cells, incompatible pharmacokinetic properties with MI, or dose-limiting adverse effects. As a result, an optimal drug delivery system should be capable of favorably accumulating therapeutic agents in the injured myocardium while upholding a reservoir that is not intensely processed by other non-targets. In the present work, in vivo imaging and flow cytometric analyses confirm that liposomes accumulate preferentially in the peri-infarct and infarct regions post-MI in the first 24 hours after infarct, indicating specific localization to the damaged myocardium. Flow cytometric analysis investigating the accumulation of liposomes in cardiac cells indicates that liposomes concentrate in immune cells, with less than 1% of non-immune cells testing positive for liposomes. This distribution strongly suggests that liposomes increase the on-target effects (enhanced efficacy), as well as reduce the off-target effects (less potential of adverse effects). Indeed, our in vivo electrophysiologic monitoring of the heart confirmed the reduction of conduction abnormalities observed with Lazm formulation compared to free AZM. By using non-PEGylated liposomes, inflammatory cells phagocytize Lazm in the leaky vasculature of the infarcted myocardium.

We previously demonstrated the immunomodulatory effectiveness of AZM as a potential therapy for cardioprotection after ischemic injury. In this earlier proof-of-concept study, pre-MI treatment was used to provide time for the drug to reach steady levels before MI induction. We also used a relatively high dose of AZM (160 mg/kg/day) consistent with previous animal studies. To avoid these translational barriers and warrant post-MI low dose AZM, we considered an encapsulated dosage form of AZM, which may enhance the immunomodulatory efficacy and facilitate faster mode of action of drugs as previously shown. Our data confirm enhanced pharmacological effects with low dose of Lazm compared to free AZM. On the other hand, using AZM could be related to cardiac conduction and hemodynamic changes. Therefore, we stopped pursuit of a long-term follow up study with free AZM due to profound adverse effects (FIG. 4). Our studies reveal that liposomal formulation is protective against adverse effects of free AZM such as the observed reduction in heart performance, presumably by reducing the uptake of AZM in non-immune cells in the heart.

It is widely accepted that neutrophils are the first immune cells to infiltrate the infarcted heart and their extended existence is associated with exacerbation of cardiac injury after ischemia. We showed in our first study that neutrophil counts are substantially decreased in mice receiving AZM, which is related to enhanced apoptosis. Recently, research shows that there are two activation states of neutrophils in the ischemic heart: early pro-inflammatory (N1) and late anti-inflammatory (N2). Interestingly, PB neutrophils are CD206−, becoming CD206+ in the heart, which indicates the plasticity of neutrophils and their ability to change in response to the surrounding microenvironment. Here, we observed that N1 neutrophils are significantly decreased with Lazm therapy, which perhaps attributable to the apoptotic effects of AZM or reduced neutrophils recruitment due to suppressed production of chemokines such as Macrophage Inflammatory Protein (MW) and Keratinocyte Chemoattractant (KC). It is possible that removal of apoptotic cells from the injured myocardium is an essential cellular mechanism to resolve inflammation by shifting macrophage phenotype. Additionally, we observed a significant reduction in cardiac Ly6C$^{hi}$ monocytes with liposomal and free AZM, suggesting a possible mechanism for the reduced number of pro-inflammatory macrophages. This phenomenon is most likely related to the diminished expression of MCP-1 in the heart and blood.

The post-MI healing phase is primarily organized by reparative macrophages. This could explain the attenuated cardiac recovery with macrophage depletion and the improved outcomes with the adoptive transfer of alternatively activated macrophages. Furthermore, multiple studies have demonstrated the therapeutic utility of shifting macrophages to the reparative phenotype post-MI. We found that liposomal and free AZM treatment was associated with higher anti-inflammatory (IBA1+CD206+ cells) and lower pro-inflammatory (IBA1+IL-1β+) macrophages after MI in peri-infarct regions. Additionally, we observed a significant reduction in apoptosis at day 3 post-MI in the same regions, which could be attributed to pro-survival factors released from reparative macrophages. These data confirm our observations in flow cytometry and analysis of inflammatory mediators. Changes in post-MI inflammation were translated into smaller scar, better cardiac function, and more newly formed blood vessels after MI. Collectively, we observed a global trend with AZM in shifting immune cells to the anti-inflammatory state.

Immune cell modulation was associated with significant downregulations in the inflammatory genes, and upregulations in the anti-inflammatory genes. Inflammatory cytokines as IL-1β, TNF-α, IL-6, and MCP-1 as well as M1 macrophages marker, iNOS, were markedly reduced in the early time points post-MI. These changes could explain the reduced infiltration of inflammatory cells into the heart. As an example, MCP-1 derives mobilization of Ly6C$^{hi}$ monocytes to the heart after infarction where they differentiate into M1 macrophages. Furthermore, reduction of MCP-1 promotes alternative activation of macrophages. Moreover, it was shown that IL-1β promotes generation of chemotactic mediators inducing myocardial injury via recruiting more immune cells to the heart. Indeed, we observed a robust decrease in the expression of IL-1β, which, at least partially, contributes to the improvement of outcomes in this study. Recently, it has been found that targeting IL-1β with monoclonal antibody, canakinumab, significantly decreases cardiovascular events reoccurrence. On the other hand, anti-inflammatory genes such as TGF-β, IL-4, and IL-10, as well as M2 macrophage markers as FIZZ1, YM1, PPAR-γ, and ARG are upregulated by free and liposomal AZM treatments. These mediators have been shown to exert multiple beneficial functions in the myocardium following MI. IL-10 modifies monocytes-macrophages function, morphology, and phenotype. Secretion of IL-1α, IL-1β, TNF-α, IL-6, and IL-8 is inhibited by IL-10 in activated monocytes. Furthermore, IL-10 could participate in matrix remodeling via enhancing tissue inhibitor of metallopeptidase 1 (TIMP-1) synthesis, thus stabilizing the ECM. TGF-β is an essential regulator for transition from inflammation to healing and organized scar formation. Through activation of endothelial mononuclear cells, TGF-β inhibits production of various pro-inflammatory cytokines and chemokines. Additionally, TGF-β stimulates fibroblasts to produce ECM proteins (collagen, fibronectin, tenascin, and proteoglycans). Moreover, TGF-β reduces the expression of proteinases (plasminogen activator and collagenase) and enhances the production of proteinases inhibitors (plasminogen activator inhibitor and TIMP-1), suppressing matrix break down and helping scar maturation. We noticed that the expression of IL-10 and TGF-β was increased with free and liposomal AZM therapy, which could explain the reduction in heart failure and mortality observed in our study. Interestingly, changes in pro-inflammatory and anti-inflammatory genes are consistent between heart and peripheral blood, suggesting systemic effect moderating the severity of the post-MI inflammation. This feature is also important from a clinical prospective since it provides a more feasible way to monitor the pharmacological effects of AZM.

In summary, this Example demonstrates that AZM is a potent immunomodulatory agent for the detrimental post-MI inflammatory response. This is the first study to demonstrate the immunomodulatory properties of liposomal AZM, which has wide therapeutic applications beyond the cardiovascular field. As such, it is expected that liposomal AZM would be beneficial as anti-inflammatory drug carriers in other sterile inflammatory diseases that share similar inflammatory profile with MI such as ischemic stroke and spinal cord injury. Moreover, this Example is the first to demonstrate that targeted AZM delivery using liposomal formulations achieve more effective immunomodulatory effects with less cardiac side effects. Immunomodulatory effects of AZM are time-and dose-dependent and we were able to enhance them by improving the pharmacokinetics and pharmacodynamics of the drug through liposomal formulations. The other important finding in the study is the excellent translatable potential of liposomal AZM (low dose, post-injury) in ischemic heart disease. We noted that low dose of Lazm, started after MI, effectively resolve post-MI inflammation and improve adverse cardiac remodeling with lower risk of adverse effects. Interestingly, we observed also that the liposomal encapsulation is truly protective from the potential unwanted effects of AZM, which is highly recommended to introduce to clinical applications. Our findings strongly support using AZM as a novel and clinically relevant therapy to improve cardiac recovery and reduce heart failure post-MI in humans. In addition, other criteria like AZM is a widely prescribed antibiotic and liposomes are effective drug delivery systems for multiple therapeutic agents form a paving way for rapid clinical translation of our findings. Finally, the prepared liposomes in this study can be harnessed to deliver other therapeutic agents to the injured myocardium.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

Akgur, F. M., M. F. Brown, G. B. Zibari, J. C. McDonald, C. J. Epstein, C. R. Ross and D. N. Granger (2000). "Role of superoxide in hemorrhagic shock-induced P-selectin expression." *Am J Physiol Heart Circ Physiol* 279(2): H791-797.

Al-Darraji, A., D. Haydar, L. Chelvaraj an, H. Tripathi, B. Levitan, E. Gao, V. J. Venditto, J. C. Gensel, D. J. Feola and A. Abdel-Latif (2018). "Azithromycin therapy reduces cardiac inflammation and mitigates adverse cardiac remodeling after myocardial infarction: Potential therapeutic targets in ischemic heart disease." PLoS One 13(7): e0200474.

Amantea, D., M. Certo, F. Petrelli, C. Tassorelli, G. Micieli, M. T. Corasaniti, P. Puccetti, F. Fallarino and G. Bagetta (2016). "Azithromycin protects mice against ischemic stroke injury by promoting macrophage transition towards M2 phenotype." Exp Neurol 275 Pt 1: 116-125.

Andrassy, M., H. C. Volz, J. C. Igwe, B. Funke, S. N. Eichberger, Z. Kaya, S. Buss, F. Autschbach, S. T. Pleger, I. K. Lukic, F. Bea, S. E. Hardt, P. M. Humpert, M. E. Bianchi, H. Mairbaurl, P. P. Nawroth, A. Remppis, H. A. Katus and A. Bierhaus (2008). "High-mobility group box-1 in ischemia-reperfusion injury of the heart." Circulation 117(25): 3216-3226.

Anversa, P., G. Olivetti and J. M. Capasso (1991). "Cellular basis of ventricular remodeling after myocardial infarction." Am J Cardiol 68(14): 7D-16D.

Anzai, A., T. Anzai, S. Nagai, Y. Maekawa, K. Naito, H. Kaneko, Y. Sugano, T. Takahashi, H. Abe, S. Mochizuki, M. Sano, T. Yoshikawa, Y. Okada, S. Koyasu, S. Ogawa and K. Fukuda (2012). "Regulatory role of dendritic cells in postinfarction healing and left ventricular remodeling." Circulation 125(10): 1234-1245.

Aoki, Y. and P. N. Kao (1999). "Erythromycin inhibits transcriptional activation of NF-kappaB, but not NFAT, through calcineurin-independent signaling in T cells." Antimicrob Agents Chemother 43(11): 2678-2684.

Aoshiba, K., A. Nagai and K. Konno (1995). "Erythromycin shortens neutrophil survival by accelerating apoptosis." Antimicrob Agents Chemother 39(4): 872-877.

Arai, M., D. J. Lefer, T. So, A. DiPaula, T. Aversano and L. C. Becker (1996). "An anti-CD18 antibody limits infarct size and preserves left ventricular function in dogs with ischemia and 48-hour reperfusion." J Am Coll Cardiol 27(5): 1278-1285.

Arslan, F., D. P. de Kleijn and G. Pasterkamp (2011). "Innate immune signaling in cardiac ischemia." Nat Rev Cardiol 8(5): 292-300.

Aurora, A. B., E. R. Porrello, W. Tan, A. I. Mahmoud, J. A. Hill, R. Bassel-Duby, H. A. Sadek and E. N. Olson (2014). "Macrophages are required for neonatal heart regeneration." J Clin Invest 124(3): 1382-1392.

Bassols, A. and J. Massague (1988). "Transforming growth factor beta regulates the expression and structure of extracellular matrix chondroitin/dermatan sulfate proteoglycans." J Biol Chem 263(6): 3039-3045.

Bauersachs, J., P. Galuppo, D. Fraccarollo, M. Christ and G. Ertl (2001). "Improvement of left ventricular remodeling and function by hydroxymethylglutaryl coenzyme a reductase inhibition with cerivastatin in rats with heart failure after myocardial infarction." Circulation 104(9): 982-985.

Beltrami, C. A., N. Finato, M. Rocco, G. A. Feruglio, C. Puricelli, E. Cigola, F. Quaini, E. H. Sonnenblick, G. Olivetti and P. Anversa (1994). "Structural basis of end-stage failure in ischemic cardiomyopathy in humans." Circulation 89(1): 151-163.

Ben-Mordechai, T., D. Palevski, Y. Glucksam-Galnoy, I. Elron-Gross, R. Margalit and J. Leor (2015). "Targeting macrophage subsets for infarct repair." J Cardiovasc Pharmacol Ther 20(1): 36-51.

Bevilacqua, M. P., J. S. Pober, D. L. Mendrick, R. S. Cotran and M. A. Gimbrone, Jr. (1987). "Identification of an inducible endothelial-leukocyte adhesion molecule." Proc Natl Acad Sci U S A 84(24): 9238-9242.

Birdsall, H. H., D. M. Green, J. Trial, K. A. Youker, A. R. Burns, C. R. MacKay, G. J. LaRosa, H. K. Hawkins, C. W. Smith, L. H. Michael, M. L. Entman and R. D. Rossen (1997). "Complement C5a, TGF-beta 1, and MCP-1, in sequence, induce migration of monocytes into ischemic canine myocardium within the first one to five hours after reperfusion." Circulation 95(3): 684-692.

Bornmann, C., R. Graeser, N. Esser, V. Ziroli, P. Jantscheff, T. Keck, C. Unger, U. T. Hopt, U. Adam, C. Schaechtele, U. Massing and E. von Dobschuetz (2008). "A new liposomal formulation of Gemcitabine is active in an orthotopic mouse model of pancreatic cancer accessible to bioluminescence imaging." Cancer Chemother Pharmacol 61(3): 395-405.

Bournazou, I., J. D. Pound, R. Duffin, S. Bournazos, L. A. Melville, S. B. Brown, A. G. Rossi and C. D. Gregory (2009). "Apoptotic human cells inhibit migration of granulocytes via release of lactoferrin." J Clin Invest 119(1): 20-32.

Bujak, M., M. Dobaczewski, C. Gonzalez-Quesada, Y. Xia, T. Leucker, P. Zymek, V. Veeranna, A. M. Tager, A. D. Luster and N. G. Frangogiannis (2009). "Induction of the CXC chemokine interferon-gamma-inducible protein 10 regulates the reparative response following myocardial infarction." Circ Res 105(10): 973-983.

Bujak, M. and N. G. Frangogiannis (2007). "The role of TGF-beta signaling in myocardial infarction and cardiac remodeling." Cardiovasc Res 74(2): 184-195.

Bujak, M. and N. G. Frangogiannis (2009). "The role of IL-1 in the pathogenesis of heart disease." Arch Immunol Ther Exp (Warsz) 57(3): 165-176.

Bulkley, B. H. and W. C. Roberts (1974). "Steroid therapy during acute myocardial infarction. A cause of delayed healing and of ventricular aneurysm." Am J Med 56(2): 244-250.

Carbone, F., A. Nencioni, F. Mach, N. Vuilleumier and F. Montecucco (2013). "Pathophysiological role of neutrophils in acute myocardial infarction." Thromb Haemost 110(3): 501-514.

Caride, V. J., J. Twickler and B. L. Zaret (1984). "Liposome kinetics in infarcted canine myocardium." J Cardiovasc Pharmacol 6(6): 996-1005.

Charrois, G. J. and T. M. Allen (2003). "Multiple injections of pegylated liposomal Doxorubicin: pharmacokinetics and therapeutic activity." J Pharmacol Exp Ther 306(3): 1058-1067.

Chatelain, P., J. G. Latour, D. Tran, M. de Lorgeril, G. Dupras and M. Bourassa (1987). "Neutrophil accumulation in experimental myocardial infarcts: relation with extent of injury and effect of reperfusion." Circulation 75(5): 1083-1090.

Chen, B. and N. G. Frangogiannis (2016). "Macrophages in the Remodeling Failing Heart." Circ Res 119(7): 776-778.

Chen, B. and N. G. Frangogiannis (2017). "Immune cells in repair of the infarcted myocardium." Microcirculation 24(1).

Chen, W., A. Saxena, N. Li, J. Sun, A. Gupta, D. W. Lee, Q. Tian, M. Dobaczewski and N. G. Frangogiannis (2012). "Endogenous IRAK-M attenuates postinfarction remodeling through effects on macrophages and fibroblasts." Arterioscler Thromb Vasc Biol 32(11): 2598-2608.

Cheraghi, M., B. Negandari, H. Daraee and A. Eatemadi (2017). "Heart targeted nanoliposomal/nanoparticles drug delivery: An updated review." *Biomed Pharmacother* 86: 316-323.

Chia, S., J. T. Nagurney, D. F. Brown, O. C. Raffel, F. Bamberg, F. Senatore, F. J. Wackers and I. K. Jang (2009). "Association of leukocyte and neutrophil counts with infarct size, left ventricular function and outcomes after percutaneous coronary intervention for ST-elevation myocardial infarction." *Am J Cardiol* 103(3): 333-337.

Christia, P. and N. G. Frangogiannis (2013). "Targeting inflammatory pathways in myocardial infarction." *Eur J Clin Invest* 43(9): 986-995.

Cigana, C., B. M. Assael and P. Melotti (2007). "Azithromycin selectively reduces tumor necrosis factor alpha levels in cystic fibrosis airway epithelial cells." *Antimicrob Agents Chemother* 51(3): 975-981.

Cochain, C., C. Auvynet, L. Poupel, J. Vilar, E. Dumeau, A. Richart, A. Recalde, Y. Zouggari, K. Y. Yin, P. Bruneval, G. Renault, C. Marchiol, P. Bonnin, B. Levy, R. Bonecchi, M. Locati, C. Combadiere and J. S. Silvestre (2012). "The chemokine decoy receptor D6 prevents excessive inflammation and adverse ventricular remodeling after myocardial infarction." *Arterioscler Thromb Vasc Biol* 32(9): 2206-2213.

Colotta, F., F. Re, N. Polentarutti, S. Sozzani and A. Mantovani (1992). "Modulation of granulocyte survival and programmed cell death by cytokines and bacterial products." *Blood* 80(8): 2012-2020.

Cory, T. J., S. E. Birket, B. S. Murphy, D. Hayes, Jr., M. I. Anstead, J. F. Kanga, R. J. Kuhn, H. M. Bush and D. J. Feola (2014). "Impact of azithromycin treatment on macrophage gene expression in subjects with cystic fibrosis." *J Cyst Fibros* 13(2): 164-171.

Courties, G., T. Heidt, M. Sebas, Y. Iwamoto, D. Jeon, J. Truelove, B. Tricot, G. Wojtkiewicz, P. Dutta, H. B. Sager, A. Borodovsky, T. Novobrantseva, B. Klebanov, K. Fitzgerald, D. G. Anderson, P. Libby, F. K. Swirski, R. Weissleder and M. Nahrendorf (2014). "In vivo silencing of the transcription factor IRF5 reprograms the macrophage phenotype and improves infarct healing." *J Am Coll Cardiol* 63(15): 1556-1566.

Crawford, M. H., F. L. Grover, W. P. Kolb, C. A. McMahan, R. A. O'Rourke, L. M. McManus and R. N. Pinckard (1988). "Complement and neutrophil activation in the pathogenesis of ischemic myocardial injury." *Circulation* 78(6): 1449-1458.

Cuartero, M. I., I. Ballesteros, A. Moraga, F. Nombela, J. Vivancos, J. A. Hamilton, A. L. Corbi, I. Lizasoain and M. A. Moro (2013). "N2 neutrophils, novel players in brain inflammation after stroke: modulation by the PPAR-gamma agonist rosiglitazone." *Stroke* 44(12): 3498-3508.

Cynamon, M. H., S. P. Klemens and C. E. Swenson (1992). "TLC G-65 in combination with other agents in the therapy of Mycobacterium avium infection in beige mice." *J Antimicrob Chemother* 29(6): 693-699.

Czermak, B. J., A. B. Lentsch, N. M. Bless, H. Schmal, H. P. Friedl and P. A. Ward (1998). "Role of complement in in vitro and in vivo lung inflammatory reactions." *J Leukoc Biol* 64(1): 40-48.

Dasa, S. S. K., R. Suzuki, M. Gutknecht, L. T. Brinton, Y. Tian, E. Michaelsson, L. Lindfors, A. L. Klibanov, B. A. French and K. A. Kelly (2015). "Development of target-specific liposomes for delivering small molecule drugs after reperfused myocardial infarction." *J Control Release* 220(Pt A): 556-567.

de Couto, G., W. Liu, E. Tseliou, B. Sun, N. Makkar, H. Kanazawa, M. Arditi and E. Marban (2015). "Macrophages mediate cardioprotective cellular postconditioning in acute myocardial infarction." *J Clin Invest* 125(8): 3147-3162.

de Lemos, J. A., D. A. Morrow, M. A. Blazing, P. Jarolim, S. D. Wiviott, M. S. Sabatine, R. M. Califf and E. Braunwald (2007). "Serial measurement of monocyte chemoattractant protein-1 after acute coronary syndromes: results from the A to Z trial." *J Am Coll Cardiol* 50(22): 2117-2124.

Del Maestro, R., H. H. Thaw, J. Bjork, M. Planker and K. E. Arfors (1980). "Free radicals as mediators of tissue injury." *Acta Physiol Scand Suppl* 492: 43-57.

Deniset, J. F. and P. Kubes (2016). "Recent advances in understanding neutrophils." *F1000Res* 5: 2912.

Desaki, M., H. Takizawa, T. Ohtoshi, T. Kasama, K. Kobayashi, T. Sunazuka, S. Omura, K. Yamamoto and K. Ito (2000). "Erythromycin suppresses nuclear factor-kappaB and activator protein-1 activation in human bronchial epithelial cells." *Biochem Biophys Res Commun* 267(1): 124-128.

Dewald, O., G. Ren, G. D. Duerr, M. Zoerlein, C. Klemm, C. Gersch, S. Tincey, L. H. Michael, M. L. Entman and N. G. Frangogiannis (2004). "Of mice and dogs: species-specific differences in the inflammatory response following myocardial infarction." *Am J Pathol* 164(2): 665-677.

Dewald, O., P. Zymek, K. Winkelmann, A. Koerting, G. Ren, T. Abou-Khamis, L. H. Michael, B. J. Rollins, M. L. Entman and N. G. Frangogiannis (2005). "CCL2/Monocyte Chemoattractant Protein-1 regulates inflammatory responses critical to healing myocardial infarcts." *Circ Res* 96(8): 881-889.

Dhalla, N. S., A. B. Elmoselhi, T. Hata and N. Makino (2000). "Status of myocardial antioxidants in ischemia-reperfusion injury." *Cardiovasc Res* 47(3): 446-456.

Dinarello, C. A. (2005). "Blocking IL-1 in systemic inflammation." *J Exp Med* 201(9): 1355-1359.

Dobaczewski, M., C. Gonzalez-Quesada and N. G. Frangogiannis (2010). "The extracellular matrix as a modulator of the inflammatory and reparative response following myocardial infarction." *J Mol Cell Cardiol* 48(3): 504-511.

Dobaczewski, M., Y. Xia, M. Bujak, C. Gonzalez-Quesada and N. G. Frangogiannis (2010). "CCR5 signaling suppresses inflammation and reduces adverse remodeling of the infarcted heart, mediating recruitment of regulatory T cells." *Am J Pathol* 176(5): 2177-2187.

Doring, Y., M. Drechsler, O. Soehnlein and C. Weber (2015). "Neutrophils in atherosclerosis: from mice to man." *Arterioscler Thromb Vasc Biol* 35(2): 288-295.

Dreyer, W. J., L. H. Michael, T. Nguyen, C. W. Smith, D. C. Anderson, M. L. Entman and R. D. Rossen (1992). "Kinetics of C5a release in cardiac lymph of dogs experiencing coronary artery ischemia-reperfusion injury." *Circ Res* 71(6): 1518-1524.

Dunlay, S. M., S. A. Weston, M. M. Redfield, J. M. Killian and V. L. Roger (2008). "Tumor necrosis factor-alpha and mortality in heart failure: a community study." *Circulation* 118(6): 625-631.

Dutta, P. and M. Nahrendorf (2015). "Monocytes in myocardial infarction." *Arterioscler Thromb Vasc Biol* 35(5): 1066-1070.

Entman, M. L. and C. W. Smith (1994). "Postreperfusion inflammation: a model for reaction to injury in cardiovascular disease." *Cardiovasc Res* 28(9): 1301-1311.

Epelman, S., K. J. Lavine, A. E. Beaudin, D. K. Sojka, J. A. Carrero, B. Calderon, T. Brija, E. L. Gautier, S. Ivanov, A. T. Satpathy, J. D. Schilling, R. Schwendener, I. Sergin, B. Razani, E. C. Forsberg, W. M. Yokoyama, E. R. Unanue, M. Colonna, G. J. Randolph and D. L. Mann (2014). "Embryonic and adult-derived resident cardiac macrophages are maintained through distinct mechanisms at steady state and during inflammation." *Immunity* 40(1): 91-104.

Epelman, S., P. P. Liu and D. L. Mann (2015). "Role of innate and adaptive immune mechanisms in cardiac injury and repair." *Nat Rev Immunol* 15(2): 117-129.

Faxon, D. P., R. J. Gibbons, N. A. Chronos, P. A. Gurbel, F. Sheehan and H. -M. Investigators (2002). "The effect of blockade of the CD11/CD18 integrin receptor on infarct size in patients with acute myocardial infarction treated with direct angioplasty: the results of the HALT-MI study." *J Am Coll Cardiol* 40(7): 1199-1204.

Feola, D. J., B. A. Garvy, T. J. Cory, S. E. Birket, H. Hoy, D. Hayes, Jr. and B. S. Murphy (2010). "Azithromycin alters macrophage phenotype and pulmonary compartmentalization during lung infection with Pseudomonas." *Antimicrob Agents Chemother* 54(6): 2437-2447.

Fischer, P. and D. Hilfiker-Kleiner (2008). "Role of gp130-mediated signalling pathways in the heart and its impact on potential therapeutic aspects." *Br J Pharmacol* 153 Suppl 1: S414-427.

Fishbein, M. C., D. Maclean and P. R. Maroko (1978). "The histopathologic evolution of myocardial infarction." *Chest* 73(6): 843-849.

Flynn, P. J., W. K. Becker, G. M. Vercellotti, D. J. Weisdorf, P. R. Craddock, D. E. Hammerschmidt, R. C. Lillehei and H. S. Jacob (1984). "Ibuprofen inhibits granulocyte responses to inflammatory mediators. A proposed mechanism for reduction of experimental myocardial infarct size." *Inflammation* 8(1): 33-44.

Foulds, G., R. M. Shepard and R. B. Johnson (1990). "The pharmacokinetics of azithromycin in human serum and tissues." *J Antimicrob Chemother* 25 Suppl A: 73-82.

Frangogiannis, N. G. (2006). "Targeting the inflammatory response in healing myocardial infarcts." *Curr Med Chem* 13(16): 1877-1893.

Frangogiannis, N. G. (2007). "Chemokines in ischemia and reperfusion." *Thromb Haemost* 97(5): 738-747.

Frangogiannis, N. G. (2012). "Regulation of the inflammatory response in cardiac repair." *Circ Res* 110(1): 159-173.

Frangogiannis, N. G. (2014). "The immune system and the remodeling infarcted heart: cell biological insights and therapeutic opportunities." *J Cardiovasc Pharmacol* 63(3): 185-195.

Frangogiannis, N. G. (2014). "The inflammatory response in myocardial injury, repair, and remodelling." *Nat Rev Cardiol* 11(5): 255-265.

Frangogiannis, N. G. (2015). "Inflammation in cardiac injury, repair and regeneration." *Curr Opin Cardiol* 30(3): 240-245.

Frangogiannis, N. G. (2018). "Cardiac fibrosis: Cell biological mechanisms, molecular pathways and therapeutic opportunities." *Mol Aspects Med*.

Frangogiannis, N. G. and M. L. Entman (2005). "Chemokines in myocardial ischemia." *Trends Cardiovasc Med* 15(5): 163-169.

Frangogiannis, N. G., M. L. Lindsey, L. H. Michael, K. A. Youker, R. B. Bressler, L. H. Mendoza, R. N. Spengler, C. W. Smith and M. L. Entman (1998). "Resident cardiac mast cells degranulate and release preformed TNF-alpha, initiating the cytokine cascade in experimental canine myocardial ischemia/reperfusion." *Circulation* 98(7): 699-710.

Frangogiannis, N. G., L. H. Mendoza, M. Lewallen, L. H. Michael, C. W. Smith and M. L. Entman (2001). "Induction and suppression of interferon-inducible protein 10 in reperfused myocardial infarcts may regulate angiogenesis." *FASEB J* 15(8): 1428-1430.

Frangogiannis, N. G., L. H. Mendoza, M. L. Lindsey, C. M. Ballantyne, L. H. Michael, C. W. Smith and M. L. Entman (2000). "IL-10 is induced in the reperfused myocardium and may modulate the reaction to injury." *J Immunol* 165(5): 2798-2808.

Frangogiannis, N. G., C. W. Smith and M. L. Entman (2002). "The inflammatory response in myocardial infarction." *Cardiovasc Res* 53(1): 31-47.

Frangogiannis, N. G., K. A. Youker, R. D. Rossen, M. Gwechenberger, M. H. Lindsey, L. H. Mendoza, L. H. Michael, C. M. Ballantyne, C. W. Smith and M. L. Entman (1998). "Cytokines and the microcirculation in ischemia and reperfusion." *J Mol Cell Cardiol* 30(12): 2567-2576.

Frantz, S., K. Hu, B. Bayer, S. Gerondakis, J. Strotmann, A. Adamek, G. Ertl and J. Bauersachs (2006). "Absence of NF-kappaB subunit p50 improves heart failure after myocardial infarction." *FASEB J* 20(11): 1918-1920.

Fridovich, I. (1978). "The biology of oxygen radicals." *Science* 201(4359): 875-880.

Frodermann, V. and M. Nahrendorf (2017). "Neutrophil-macrophage cross-talk in acute myocardial infarction." *Eur Heart J* 38(3): 198-200.

Fuchs, M., A. Hilfiker, K. Kaminski, D. Hilfiker-Kleiner, Z. Guener, G. Klein, E. Podewski, B. Schieffer, S. Rose-John and H. Drexler (2003). "Role of interleukin-6 for LV remodeling and survival after experimental myocardial infarction." *FASEB J* 17(14): 2118-2120.

Gabizon, A., H. Shmeeda and Y. Barenholz (2003). "Pharmacokinetics of pegylated liposomal Doxorubicin: review of animal and human studies." *Clin Pharmacokinet* 42(5): 419-436.

Gallagher, K. P., A. J. Buda, D. Pace, R. A. Gerren and M. Shlafer (1986). "Failure of superoxide dismutase and catalase to alter size of infarction in conscious dogs after 3 hours of occlusion followed by reperfusion." *Circulation* 73(5): 1065-1076.

Gao, E., Y. H. Lei, X. Shang, Z. M. Huang, L. Zuo, M. Boucher, Q. Fan, J. K. Chuprun, X. L. Ma and W. J. Koch (2010). "A novel and efficient model of coronary artery ligation and myocardial infarction in the mouse." *Circ Res* 107(12): 1445-1453.

Gardner, P. R. and I. Fridovich (1992). "Inactivation-reactivation of aconitase in *Escherichia coli*. A sensitive measure of superoxide radical." *J Biol Chem* 267(13): 8757-8763.

Garlichs, C. D., S. Eskafi, I. Cicha, A. Schmeisser, B. Walzog, D. Raaz, C. Stumpf, A. Yilmaz, J. Bremer, J. Ludwig and W. G. Daniel (2004). "Delay of neutrophil apoptosis in acute coronary syndromes." *J Leukoc Biol* 75(5): 828-835.

Gensel, J. C., T. J. Kopper, B. Zhang, M. B. Orr and W. M. Bailey (2017). "Predictive screening of M1 and M2 macrophages reveals the immunomodulatory effectiveness of post spinal cord injury azithromycin treatment." *Sci Rep* 7: 40144.

Gensel, J. C. and B. Zhang (2015). "Macrophage activation and its role in repair and pathology after spinal cord injury." *Brain Res* 1619: 1-11.

Gersch, C., O. Dewald, M. Zoerlein, L. H. Michael, M. L. Entman and N. G. Frangogiannis (2002). "Mast cells and macrophages in normal C57/BL/6 mice." *Histochem Cell Biol* 118(1): 41-49.

Gibbs, D. F., T. P. Shanley, R. L. Warner, H. S. Murphy, J. Varani and K. J. Johnson (1999). "Role of matrix metalloproteinases in models of macrophage-dependent acute lung injury. Evidence for alveolar macrophage as source of proteinases." *Am J Respir Cell Mol Biol* 20(6): 1145-1154.

Ginhoux, F., M. Greter, M. Leboeuf, S. Nandi, P. See, S. Gokhan, M. F. Mehler, S. J. Conway, L. G. Ng, E. R. Stanley, I. M. Samokhvalov and M. Merad (2010). "Fate mapping analysis reveals that adult microglia derive from primitive macrophages." *Science* 330(6005): 841-845.

Gleissner, C. A., I. Shaked, K. M. Little and K. Ley (2010). "CXC chemokine ligand 4 induces a unique transcriptome in monocyte-derived macrophages." *J Immunol* 184(9): 4810-4818.

Godwin, J. W., A. R. Pinto and N. A. Rosenthal (2013). "Macrophages are required for adult salamander limb regeneration." *Proc Natl Acad Sci U S A* 110(23): 9415-9420.

Gombozhapova, A., Y. Rogovskaya, V. Shurupov, M. Rebenkova, J. Kzhyshkowska, S. V. Popov, R. S. Karpov and V. Ryabov (2017). "Macrophage activation and polarization in post-infarction cardiac remodeling." *J Biomed Sci* 24(1): 13.

Gordon, J. R. and S. J. Galli (1990). "Mast cells as a source of both preformed and immunologically inducible TNF-alpha/cachectin." *Nature* 346(6281): 274-276.

Gordon, J. W., J. A. Shaw and L. A. Kirshenbaum (2011). "Multiple facets of NF-kappaB in the heart: to be or not to NF-kappaB." *Circ Res* 108(9): 1122-1132.

Gosselin, D., V. M. Link, C. E. Romanoski, G. J. Fonseca, D. Z. Eichenfield, N. J. Spann, J. D. Stender, H. B. Chun, H. Garner, F. Geissmann and C. K. Glass (2014). "Environment drives selection and function of enhancers controlling tissue-specific macrophage identities." *Cell* 159(6): 1327-1340.

Granger, D. N. (1988). "Role of xanthine oxidase and granulocytes in ischemia-reperfusion injury." *Am J Physiol* 255(6 Pt 2): H1269-1275.

Griselli, M., J. Herbert, W. L. Hutchinson, K. M. Taylor, M. Sohail, T. Krausz and M. B. Pepys (1999). "C-reactive protein and complement are important mediators of tissue damage in acute myocardial infarction." *J Exp Med* 190(12): 1733-1740.

Guasti, L., F. Dentali, L. Castiglioni, L. Maroni, F. Marino, A. Squizzato, W. Ageno, M. Gianni, G. Gaudio, A. M. Grandi, M. Cosentino and A. Venco (2011). "Neutrophils and clinical outcomes in patients with acute coronary syndromes and/or cardiac revascularisation. A systematic review on more than 34,000 subjects." *Thromb Haemost* 106(4): 591-599.

Guillen, I., M. Blanes, M. J. Gomez-Lechon and J. V. Castell (1995). "Cytokine signaling during myocardial infarction: sequential appearance of IL-1 beta and IL-6." *Am J Physiol* 269(2 Pt 2): R229-235.

Hamid, T., Y. Gu, R. V. Ortines, C. Bhattacharya, G. Wang, Y. T. Xuan and S. D. Prabhu (2009). "Divergent tumor necrosis factor receptor-related remodeling responses in heart failure: role of nuclear factor-kappaB and inflammatory activation." *Circulation* 119(10): 1386-1397.

Han, Y., J. Jing, S. Tu, F. Tian, H. Xue, W. Chen, J. Chen, J. H. Reiber and Y. Chen (2014). "ST elevation acute myocardial infarction accelerates non-culprit coronary lesion atherosclerosis." *Int J Cardiovasc Imaging* 30(2): 253-261.

Hanna, R. N., L. M. Carlin, H. G. Hubbeling, D. Nackiewicz, A. M. Green, J. A. Punt, F. Geissmann and C. C. Hedrick (2011). "The transcription factor NR4A1 (Nur77) controls bone marrow differentiation and the survival of Ly6C-monocytes." *Nat Immunol* 12(8): 778-785.

Hansen, P. R. (1995). "Role of neutrophils in myocardial ischemia and reperfusion." *Circulation* 91(6): 1872-1885.

Harel-Adar, T., T. Ben Mordechai, Y. Amsalem, M. S. Feinberg, J. Leor and S. Cohen (2011). "Modulation of cardiac macrophages by phosphatidylserine-presenting liposomes improves infarct repair." *Proc Natl Acad Sci U S A* 108(5): 1827-1832.

Hartman, M. H. T., H. E. Groot, I. M. Leach, J. C. Karper and P. van der Harst (2018). "Translational overview of cytokine inhibition in acute myocardial infarction and chronic heart failure." *Trends Cardiovasc Med* 28(6): 369-379.

Hazlett, L. D., S. A. McClellan, R. P. Barrett, X. Huang, Y. Zhang, M. Wu, N. van Rooijen and E. Szliter (2010). "IL-33 shifts macrophage polarization, promoting resistance against *Pseudomonas aeruginosa* keratitis." *Invest Ophthalmol Vis Sci* 51(3): 1524-1532.

Heidenreich, P. A., N. M. Albert, L. A. Allen, D. A. Bluemke, J. Butler, G. C. Fonarow, J. S. Ikonomidis, O. Khavjou, M. A. Konstam, T. M. Maddox, G. Nichol, M. Pham, I. L. Pina, J. G. Trogdon, C. American Heart Association Advocacy Coordinating, T. Council on Arteriosclerosis, B. Vascular, R. Council on Cardiovascular, Intervention, C. Council on Clinical, E. Council on, Prevention and C. Stroke (2013). "Forecasting the impact of heart failure in the United States: a policy statement from the American Heart Association." *Circ Heart Fail* 6(3): 606-619.

Heidt, T., G. Courties, P. Dutta, H. B. Sager, M. Sebas, Y. Iwamoto, Y. Sun, N. Da Silva, P. Panizzi, A. M. van der Laan, F. K. Swirski, R. Weissleder and M. Nahrendorf (2014). "Differential contribution of monocytes to heart macrophages in steady-state and after myocardial infarction." *Circ Res* 115(2): 284-295.

Heo, S. C., Y. W. Kwon, I. H. Jang, G. O. Jeong, T. W. Lee, J. W. Yoon, H. J. Shin, H. C. Jeong, Y. Ahn, T. H. Ko, S. C. Lee, J. Han and J. H. Kim (2017). "Formyl Peptide Receptor 2 Is Involved in Cardiac Repair After Myocardial Infarction Through Mobilization of Circulating Angiogenic Cells." *Stem Cells* 35(3): 654-665.

Hess, M. L. and R. C. Kukrej a (1995). "Free radicals, calcium homeostasis, heat shock proteins, and myocardial stunning." *Ann Thorac Surg* 60(3): 760-766.

Hettinger, J., D. M. Richards, J. Hansson, M. M. Barra, A. C. Joschko, J. Krijgsveld and M. Feuerer (2013). "Origin of monocytes and macrophages in a committed progenitor." *Nat Immunol* 14(8): 821-830.

Heusch, G. and B. J. Gersh (2017). "The pathophysiology of acute myocardial infarction and strategies of protection beyond reperfusion: a continual challenge." *Eur Heart J* 38(11): 774-784.

Hilgendorf, I., L. M. Gerhardt, T. C. Tan, C. Winter, T. A. Holderried, B. G. Chousterman, Y. Iwamoto, R. Liao, A. Zirlik, M. Scherer-Crosbie, C. C. Hedrick, P. Libby, M. Nahrendorf, R. Weissleder and F. K. Swirski (2014). "Ly-6Chigh monocytes depend on Nr4a1 to balance both inflammatory and reparative phases in the infarcted myocardium." *Circ Res* 114(10): 1611-1622.

Hill, J. H. and P. A. Ward (1971). "The phlogistic role of C3 leukotactic fragments in myocardial infarcts of rats." *J Exp Med* 133(4): 885-900.

Hodge, S., G. Hodge, S. Brozyna, H. Jersmann, M. Holmes and P. N. Reynolds (2006). "Azithromycin increases phagocytosis of apoptotic bronchial epithelial cells by alveolar macrophages." *Eur Respir J* 28(3): 486-495.

Hofmann, U. and S. Frantz (2015). "Role of lymphocytes in myocardial injury, healing, and remodeling after myocardial infarction." *Circ Res* 116(2): 354-367.

Honold, L. and M. Nahrendorf (2018). "Resident and Monocyte-Derived Macrophages in Cardiovascular Disease." *Circ Res* 122(1): 113-127.

Horckmans, M., L. Ring, J. Duchene, D. Santovito, M. J. Schloss, M. Drechsler, C. Weber, O. Soehnlein and S. Steffens (2017). "Neutrophils orchestrate post-myocardial infarction healing by polarizing macrophages towards a reparative phenotype." *Eur Heart J* 38(3): 187-197.

Huebener, P., T. Abou-Khamis, P. Zymek, M. Bujak, X. Ying, K. Chatila, S. Haudek, G. Thakker and N. G. Frangogiannis (2008). "CD44 is critically involved in infarct healing by regulating the inflammatory and fibrotic response." *J Immunol* 180(4): 2625-2633.

Hulsmans, M., S. Clauss, L. Xiao, A. D. Aguirre, K. R. King, A. Hanley, W. J. Hucker, E. M. Wulfers, G. Seemann, G. Courties, Y. Iwamoto, Y. Sun, A. J. Savol, H. B. Sager, K. J. Lavine, G. A. Fishbein, D. E. Capen, N. Da Silva, L. Miquerol, H. Wakimoto, C. E. Seidman, J. G. Seidman, R. I. Sadreyev, K. Naxerova, R. N. Mitchell, D. Brown, P. Libby, R. Weissleder, F. K. Swirski, P. Kohl, C. Vinegoni, D. J. Milan, P. T. Ellinor and M. Nahrendorf (2017). "Macrophages Facilitate Electrical Conduction in the Heart." *Cell* 169(3): 510-522 e520.

Hulsmans, M., F. Sam and M. Nahrendorf (2016). "Monocyte and macrophage contributions to cardiac remodeling." *J Mol Cell Cardiol* 93: 149-155.

Huynh, M. L., V. A. Fadok and P. M. Henson (2002). "Phosphatidylserine-dependent ingestion of apoptotic cells promotes TGF-beta1 secretion and the resolution of inflammation." *J Clin Invest* 109(1): 41-50.

Ikeuchi, M., H. Tsutsui, T. Shiomi, H. Matsusaka, S. Matsushima, J. Wen, T. Kubota and A. Takeshita (2004). "Inhibition of TGF-beta signaling exacerbates early cardiac dysfunction but prevents late remodeling after infarction." *Cardiovasc Res* 64(3): 526-535.

Imamura, Y., K. Yanagihara, Y. Mizuta, M. Seki, H. Ohno, Y. Higashiyama, Y. Miyazaki, K. Tsukamoto, Y. Hirakata, K. Tomono, J. Kadota and S. Kohno (2004). "Azithromycin inhibits MUC5AC production induced by the Pseudomonas aeruginosa autoinducer N-(3-Oxododecanoyl) homoserine lactone in NCI-H292 Cells." *Antimicrob Agents Chemother* 48(9): 3457-3461.

Inamura, K., N. Ohta, S. Fukase, N. Kasajima and M. Aoyagi (2000). "The effects of erythromycin on human peripheral neutrophil apoptosis." *Rhinology* 38(3): 124-129.

Ishikawa, S., T. Noma, H. Y. Fu, T. Matsuzaki, M. Ishizawa, K. Ishikawa, K. Murakami, N. Nishimoto, A. Nishiyama and T. Minamino (2017). "Apoptosis inhibitor of macrophage depletion decreased M1 macrophage accumulation and the incidence of cardiac rupture after myocardial infarction in mice." *PLoS One* 12(11): e0187894.

Ito, B. R., H. Tate, M. Kobayashi and W. Schaper (1987). "Reversibly injured, postischemic canine myocardium retains normal contractile reserve." *Circ Res* 61(6): 834-846.

Ivetic Tkalcevic, V., B. Bosnjak, B. Hrvacic, M. Bosnar, N. Marjanovic, Z. Ferencic, K. Situm, O. Culic, M. J. Parnham and V. Erakovic (2006). "Anti-inflammatory activity of azithromycin attenuates the effects of lipopolysaccharide administration in mice." *Eur J Pharmacol* 539(1-2): 131-138.

Jiang, C., W. E. Finkbeiner, J. H. Widdicombe, S. L. Fang, K. X. Wang, J. B. Nietupski, K. M. Hehir and S. H. Cheng (1999). "Restoration of cyclic adenosine monophosphate-stimulated chloride channel activity in human cystic fibrosis tracheobronchial submucosal gland cells by adenovirus-mediated and cationic lipid-mediated gene transfer." *Am J Respir Cell Mol Biol* 20(6): 1107-1115.

Jolly, S. R., W. J. Kane, M. B. Bailie, G. D. Abrams and B. R. Lucchesi (1984). "Canine myocardial reperfusion injury. Its reduction by the combined administration of superoxide dismutase and catalase." *Circ Res* 54(3): 277-285.

Jugdutt, B. I., G. M. Hutchins, B. H. Bulkley and L. C. Becker (1980). "Salvage of ischemic myocardium by ibuprofen during infarction in the conscious dog." *Am J Cardiol* 46(1): 74-82.

Jugdutt, B. I. and B. L. Michorowski (1987). "Role of infarct expansion in rupture of the ventricular septum after acute myocardial infarction: a two-dimensional echocardiographic study." *Clin Cardiol* 10(11): 641-652.

Kain, V., K. A. Ingle, R. A. Colas, J. Dalli, S. D. Prabhu, C. N. Serhan, M. Joshi and G. V. Halade (2015). "Resolvin D1 activates the inflammation resolving response at splenic and ventricular site following myocardial infarction leading to improved ventricular function." *J Mol Cell Cardiol* 84: 24-35.

Kain, V., F. Liu, V. Kozlovskaya, K. A. Ingle, S. Bolisetty, A. Agarwal, S. Khedkar, S. D. Prabhu, E. Kharlampieva and G. V. Halade (2017). "Resolution Agonist 15-epi-Lipoxin A4 Programs Early Activation of Resolving Phase in Post-Myocardial Infarction Healing." *Sci Rep* 7(1): 9999.

Kalogeris, T., C. P. Baines, M. Krenz and R. J. Korthuis (2012). "Cell biology of ischemia/reperfusion injury." *Int Rev Cell Mol Biol* 298: 229-317.

Kaneko, Y., K. Yanagihara, M. Seki, M. Kuroki, Y. Miyazaki, Y. Hirakata, H. Mukae, K. Tomono, J. Kadota and S. Kohno (2003). "Clarithromycin inhibits overproduction of muc5ac core protein in murine model of diffuse panbronchiolitis." *Am J Physiol Lung Cell Mol Physiol* 285(4): L847-853.

Kanoh, S. and B. K. Rubin (2010). "Mechanisms of action and clinical application of macrolides as immunomodulatory medications." *Clin Microbiol Rev* 23(3): 590-615.

Kawaguchi, M., M. Takahashi, T. Hata, Y. Kashima, F. Usui, H. Morimoto, A. Izawa, Y. Takahashi, J. Masumoto, J. Koyama, M. Hongo, T. Noda, J. Nakayama, J. Sagara, S. Taniguchi and U. Ikeda (2011). "Inflammasome activation of cardiac fibroblasts is essential for myocardial ischemia/reperfusion injury." *Circulation* 123(6): 594-604.

Kelly, C., C. Jefferies and S. A. Cryan (2011). "Targeted liposomal drug delivery to monocytes and macrophages." *J Drug Deliv* 2011: 727241.

Keyes, K. T., Y. Ye, Y. Lin, C. Zhang, J. R. Perez-Polo, P. Gjorstrup and Y. Birnbaum (2010). "Resolvin E1 protects the rat heart against reperfusion injury." *Am J Physiol Heart Circ Physiol* 299(1): H153-164.

Kierstead, P. H., H. Okochi, V. J. Venditto, T. C. Chuong, S. Kivimae, J. M. J. Frechet and F. C. Szoka (2015). "The effect of polymer backbone chemistry on the induction of the accelerated blood clearance in polymer modified liposomes." *J Control Release* 213: 1-9.

Kilgore, K. S., G. S. Friedrichs, J. W. Homeister and B. R. Lucchesi (1994). "The complement system in myocardial ischaemia/reperfusion injury." *Cardiovasc Res* 28(4): 437-444.

Klyachkin, Y. M., P. R. Nagareddy, S. Ye, M. Wysoczynski, A. Asfour, E. Gao, M. Sunkara, J. A. Brandon, R. Annabathula, R. Ponnapureddy, M. Solanki, Z. H. Pervaiz, S. S. Smyth, M. Z. Ratajczak, A. J. Morris and A. Abdel-Latif (2015). "Pharmacological Elevation of Circulating Bioactive Phosphosphingolipids Enhances Myocardial Recovery After Acute Infarction." *Stem Cells Transl Med* 4(11): 1333-1343.

Kobara, M., K. Noda, M. Kitamura, A. Okamoto, T. Shiraishi, H. Toba, H. Matsubara and T. Nakata (2010). "Antibody against interleukin-6 receptor attenuates left ventricular remodelling after myocardial infarction in mice." *Cardiovasc Res* 87(3): 424-430.

Koch, C. C., D. J. Esteban, A. C. Chin, M. E. Olson, R. R. Read, H. Ceri, D. W. Morck and A. G. Buret (2000). "Apoptosis, oxidative metabolism and interleukin-8 production in human neutrophils exposed to azithromycin: effects of Streptococcus pneumoniae." *J Antimicrob Chemother* 46(1): 19-26.

Korf-Klingebiel, M., M. R. Reboll, S. Klede, T. Brod, A. Pich, F. Polten, L. C. Napp, J. Bauersachs, A. Ganser, E. Brinkmann, I. Reimann, T. Kempf, H. W. Niessen, J. Mizrahi, H. J. Schonfeld, A. Iglesias, M. Bobadilla, Y. Wang and K. C. Wollert (2015). "Myeloid-derived growth factor (C19orf10) mediates cardiac repair following myocardial infarction." *Nat Med* 21(2): 140-149.

Kupatt, C., H. Habazettl, A. Goedecke, D. A. Wolf, S. Zahler, P. Boekstegers, R. A. Kelly and B. F. Becker (1999). "Tumor necrosis factor-alpha contributes to ischemia- and reperfusion-induced endothelial activation in isolated hearts." *Circ Res* 84(4): 392-400.

Kzhyshkowska, J., A. Gratchev and S. Goerdt (2006). "Stabilin-1, a homeostatic scavenger receptor with multiple functions." *J Cell Mol Med* 10(3): 635-649.

Lacraz, S., L. P. Nicod, R. Chicheportiche, H. G. Welgus and J. M. Dayer (1995). "IL-10 inhibits metalloproteinase and stimulates TIMP-1 production in human mononuclear phagocytes." *J Clin Invest* 96(5): 2304-2310.

Laiho, M., O. Saksela, P. A. Andreasen and J. Keski-Oja (1986). "Enhanced production and extracellular deposition of the endothelial-type plasminogen activator inhibitor in cultured human lung fibroblasts by transforming growth factor-beta." *J Cell Biol* 103(6 Pt 1): 2403-2410.

Lakshminarayanan, V., D. W. Beno, R. H. Costa and K. A. Roebuck (1997). "Differential regulation of interleukin-8 and intercellular adhesion molecule-1 by H2O2 and tumor necrosis factor-alpha in endothelial and epithelial cells." *J Biol Chem* 272(52): 32910-32918.

Lakshminarayanan, V., E. A. Drab-Weiss and K. A. Roebuck (1998). "H2O2 and tumor necrosis factor-alpha induce differential binding of the redox-responsive transcription factors AP-1 and NF-kappaB to the interleukin-8 promoter in endothelial and epithelial cells." *J Biol Chem* 273(49): 32670-32678.

Lambert, J. M., E. F. Lopez and M. L. Lindsey (2008). "Macrophage roles following myocardial infarction." *Int J Cardiol* 130(2): 147-158.

Lara-Pezzi, E., P. Menasche, J. H. Trouvin, L. Badimon, J. P. Ioannidis, J. C. Wu, J. A. Hill, W. J. Koch, A. F. De Felice, P. de Waele, V. Steenwinckel, R. J. Hajjar and A. M. Zeiher (2015). "Guidelines for translational research in heart failure." *J Cardiovasc Transl Res* 8(1): 3-22.

Lavin, Y., D. Winter, R. Blecher-Gonen, E. David, H. Keren-Shaul, M. Merad, S. Jung and I. Amit (2014). "Tissue-resident macrophage enhancer landscapes are shaped by the local microenvironment." *Cell* 159(6): 1312-1326.

Leblond, A. L., K. Klinkert, K. Martin, E. C. Turner, A. H. Kumar, T. Browne and N. M. Caplice (2015). "Systemic and Cardiac Depletion of M2 Macrophage through CSF-1R Signaling Inhibition Alters Cardiac Function Post Myocardial Infarction." *PLoS One* 10(9): e0137515.

Lee, S. H., P. L. Wolf, R. Escudero, R. Deutsch, S. W. Jamieson and P. A. Thistlethwaite (2000). "Early expression of angiogenesis factors in acute myocardial ischemia and infarction." *N Engl J Med* 342(9): 626-633.

Lefer, A. M., P. Tsao, N. Aoki and M. A. Palladino, Jr. (1990). "Mediation of cardioprotection by transforming growth factor-beta." *Science* 249(4964): 61-64.

Lefer, D. J. and D. N. Granger (2000). "Oxidative stress and cardiac disease." *Am J Med* 109(4): 315-323.

Leid, J., J. Carrelha, H. Boukarabila, S. Epelman, S. E. Jacobsen and K. J. Lavine (2016). "Primitive Embryonic Macrophages are Required for Coronary Development and Maturation." *Circ Res* 118(10): 1498-1511.

Leme, C. V., L. S. Raposo, M. T. Ruiz, J. M. Biselli, A. L. Galbiatti, J. V. Maniglia, E. C. Pavarino-Bertelli and E. M. Goloni-Bertollo (2010). "[GSTM1 and GSTT1 genes analysis in head and neck cancer patients]." *Rev Assoc Med Bras* (1992) 56(3): 299-303.

Lenardo, M. J. and D. Baltimore (1989). "NF-kappa B: a pleiotropic mediator of inducible and tissue-specific gene control." *Cell* 58(2): 227-229.

Leor, J., L. Rozen, A. Zuloff-Shani, M. S. Feinberg, Y. Amsalem, I. M. Barbash, E. Kachel, R. Holbova, Y. Mardor, D. Daniels, A. Ocherashvilli, A. Orenstein and D. Danon (2006). "Ex vivo activated human macrophages improve healing, remodeling, and function of the infarcted heart." *Circulation* 114(1 Suppl): I94-100.

Leuschner, F., P. J. Rauch, T. Ueno, R. Gorbatov, B. Marinelli, W. W. Lee, P. Dutta, Y. Wei, C. Robbins, Y. Iwamoto, B. Sena, A. Chudnovskiy, P. Panizzi, E. Keliher, J. M. Higgins, P. Libby, M. A. Moskowitz, M. J. Pittet, F. K. Swirski, R. Weissleder and M. Nahrendorf (2012). "Rapid monocyte kinetics in acute myocardial infarction are sustained by extramedullary monocytopoiesis." *J Exp Med* 209(1): 123-137.

Levchenko, T. S., W. C. Hartner and V. P. Torchilin (2012). "Liposomes in diagnosis and treatment of cardiovascular disorders." *Methodist Debakey Cardiovasc J* 8(1): 36-41.

Li, J., L. F. Brown, M. G. Hibberd, J. D. Grossman, J. P. Morgan and M. Simons (1996). "VEGF, flk-1, and flt-1 expression in a rat myocardial infarction model of angiogenesis." *Am J Physiol* 270(5 Pt 2): H1803-1811.

Liaudet, L. and N. Rosenblatt-Velin (2013). "Role of innate immunity in cardiac inflammation after myocardial infarction." *Front Biosci* (Schol Ed) 5: 86-104.

Lindsey, M. L., J. J. Saucerman and K. Y. DeLeon-Pennell (2016). "Knowledge gaps to understanding cardiac macrophage polarization following myocardial infarction." *Biochim Biophys Acta* 1862(12): 2288-2292.

Liu, J., H. Wang and J. Li (2016). "Inflammation and Inflammatory Cells in Myocardial Infarction and Reperfusion Injury: A Double-Edged Sword." *Clin Med Insights Cardiol* 10: 79-84.

Lorchner, H., J. Poling, P. Gajawada, Y. Hou, V. Polyakova, S. Kostin, J. M. Adrian-Segarra, T. Boettger, A.

Wietelmann, H. Warnecke, M. Richter, T. Kubin and T. Braun (2015). "Myocardial healing requires Reg3beta-dependent accumulation of macrophages in the ischemic heart." *Nat Med* 21(4): 353-362.

Lucchesi, B. R. (1990). "Myocardial ischemia, reperfusion and free radical injury." *Am J Cardiol* 65(19): 141-231.

Lucchesi, B. R. and K. S. Kilgore (1997). "Complement inhibitors in myocardial ischemia/reperfusion injury." *Immunopharmacology* 38(1-2): 27-42.

Lucchesi, B. R., S. W. Werns and J. C. Fantone (1989). "The role of the neutrophil and free radicals in ischemic myocardial injury." *J Mol Cell Cardiol* 21(12): 1241-1251.

Ma, Y., Y. A. Chiao, R. Clark, E. R. Flynn, A. Yabluchanskiy, O. Ghasemi, F. Zouein, M. L. Lindsey and Y. F. Jin (2015). "Deriving a cardiac ageing signature to reveal MMP-9-dependent inflammatory signalling in senescence." *Cardiovasc Res* 106(3): 421-431.

Ma, Y., A. J. Mouton and M. L. Lindsey (2018). "Cardiac macrophage biology in the steady-state heart, the aging heart, and following myocardial infarction." *Transl Res* 191: 15-28.

Ma, Y., A. Yabluchanskiy, R. P. Iyer, P. L. Cannon, E. R. Flynn, M. Jung, J. Henry, C. A. Cates, K. Y. Deleon-Pennell and M. L. Lindsey (2016). "Temporal neutrophil polarization following myocardial infarction." *Cardiovasc Res* 110(1): 51-61.

Ma, Y., A. Yabluchanskiy and M. L. Lindsey (2013). "Neutrophil roles in left ventricular remodeling following myocardial infarction." *Fibrogenesis Tissue Repair* 6(1): 11.

Maekawa, Y., T. Anzai, T. Yoshikawa, Y. Asakura, T. Takahashi, S. Ishikawa, H. Mitamura and S. Ogawa (2002). "Prognostic significance of peripheral monocytosis after reperfused acute myocardial infarction:a possible role for left ventricular remodeling." *J Am Coll Cardiol* 39(2): 241-246.

Mahbub, S., C. R. Deburghgraeve and E. J. Kovacs (2012). "Advanced age impairs macrophage polarization." *J Interferon Cytokine Res* 32(1): 18-26.

Mantovani, A. (2008). "From phagocyte diversity and activation to probiotics: back to Metchnikoff." *Eur J Immunol* 38(12): 3269-3273.

Mantovani, A., S. K. Biswas, M. R. Galdiero, A. Sica and M. Locati (2013). "Macrophage plasticity and polarization in tissue repair and remodelling." *J Pathol* 229(2): 176-185.

Mantovani, A., A. Sica, S. Sozzani, P. Allavena, A. Vecchi and M. Locati (2004). "The chemokine system in diverse forms of macrophage activation and polarization." *Trends Immunol* 25(12): 677-686.

Margulis, K., E. A. Neofytou, R. E. Beygui and R. N. Zare (2015). "Celecoxib Nanoparticles for Therapeutic Angiogenesis." *ACS Nano* 9(9): 9416-9426.

Martinez, F. O., S. Gordon, M. Locati and A. Mantovani (2006). "Transcriptional profiling of the human monocyte-to-macrophage differentiation and polarization: new molecules and patterns of gene expression." *J Immunol* 177(10): 7303-7311.

Martinez, F. O., A. Sica, A. Mantovani and M. Locati (2008). "Macrophage activation and polarization." *Front Biosci* 13: 453-461.

Maxwell, S. R. and G. Y. Lip (1997). "Reperfusion injury: a review of the pathophysiology, clinical manifestations and therapeutic options." *Int J Cardiol* 58(2): 95-117.

McGrath-Morrow, S. A. and J. L. Stahl (2000). "G(1) Phase growth arrest and induction of p21(Waf1/Cip1/Sdi1) in IB3-1 cells treated with 4-sodium phenylbutyrate." *J Pharmacol Exp Ther* 294(3): 941-947.

Medzhitov, R. and T. Horng (2009). "Transcriptional control of the inflammatory response." *Nat Rev Immunol* 9(10): 692-703.

Mehta, J. L. and D. Y. Li (1999). "Inflammation in ischemic heart disease: response to tissue injury or a pathogenetic villain?" *Cardiovasc Res* 43(2): 291-299.

Mezzaroma, E., S. Toldo, D. Farkas, I. M. Seropian, B. W. Van Tassell, F. N. Salloum, H. R. Kannan, A. C. Menna, N. F. Voelkel and A. Abbate (2011). "The inflammasome promotes adverse cardiac remodeling following acute myocardial infarction in the mouse." *Proc Natl Acad Sci U S A* 108(49): 19725-19730.

Milla, C., S. Yang, D. N. Cornfield, M. L. Brennan, S. L. Hazen, A. Panoskaltsis-Mortari, B. R. Blazar and I. Y. Haddad (2004). "Myeloperoxidase deficiency enhances inflammation after allogeneic marrow transplantation." *Am J Physiol Lung Cell Mol Physiol* 287(4): L706-714.

Misra, A., S. B. Haudek, P. Knuefermann, J. G. Vallejo, Z. J. Chen, L. H. Michael, N. Sivasubramanian, E. N. Olson, M. L. Entman and D. L. Mann (2003). "Nuclear factor-kappaB protects the adult cardiac myocyte against ischemia-induced apoptosis in a murine model of acute myocardial infarction." *Circulation* 108(25): 3075-3078.

Molawi, K., Y. Wolf, P. K. Kandalla, J. Favret, N. Hagemeyer, K. Frenzel, A. R. Pinto, K. Klapproth, S. Henri, B. Malissen, H. R. Rodewald, N. A. Rosenthal, M. Bajenoff, M. Prinz, S. Jung and M. H. Sieweke (2014). "Progressive replacement of embryo-derived cardiac macrophages with age." *J Exp Med* 211(11): 2151-2158.

Morishita, R., T. Sugimoto, M. Aoki, I. Kida, N. Tomita, A. Moriguchi, K. Maeda, Y. Sawa, Y. Kaneda, J. Higaki and T. Ogihara (1997). "In vivo transfection of cis element "decoy" against nuclear factor-kappaB binding site prevents myocardial infarction." *Nat Med* 3(8): 894-899.

Moro, C., M. G. Jouan, A. Rakotovao, M. C. Toufektsian, O. Ormezzano, N. Nagy, A. Tosaki, J. de Leiris and F. Boucher (2007). "Delayed expression of cytokines after reperfused myocardial infarction: possible trigger for cardiac dysfunction and ventricular remodeling." *Am J Physiol Heart Circ Physiol* 293(5): H3014-3019.

Mosmann, T. R. (1994). "Properties and functions of interleukin-10." *Adv Immunol* 56: 1-26.

Mouton, A. J., O. J. Rivera and M. L. Lindsey (2018). "Myocardial infarction remodeling that progresses to heart failure: a signaling misunderstanding." *Am J Physiol Heart Circ Physiol* 315(1): H71-H79.

Mueller, T. M., M. L. Marcus, H. E. Mayer, J. K. Williams and K. Hermsmeyer (1981). "Liposome concentration in canine ischemic myocardium and depolarized myocardial cells." *Circ Res* 49(2): 405-415.

Mulder, R., A. Banete and S. Basta (2014). "Spleen-derived macrophages are readily polarized into classically activated (M1) or alternatively activated (M2) states." *Immunobiology* 219(10): 737-745.

Mullane, K. M., R. Kraemer and B. Smith (1985). "Myeloperoxidase activity as a quantitative assessment of neutrophil infiltration into ischemic myocardium." *J Pharmacol Methods* 14(3): 157-167.

Mullane, K. M., N. Read, J. A. Salmon and S. Moncada (1984). "Role of leukocytes in acute myocardial infarction in anesthetized dogs: relationship to myocardial salvage by anti-inflammatory drugs." *J Pharmacol Exp Ther* 228(2): 510-522.

Murphy, B. S., V. Sundareshan, T. J. Cory, D. Hayes, Jr., M. I. Anstead and D. J. Feola (2008). "Azithromycin alters macrophage phenotype." *J Antimicrob Chemother* 61(3): 554-560.

Murray, P. J., J. E. Allen, S. K. Biswas, E. A. Fisher, D. W. Gilroy, S. Goerdt, S. Gordon, J. A. Hamilton, L. B. Ivashkiv, T. Lawrence, M. Locati, A. Mantovani, F. O. Martinez, J. L. Mege, D. M. Mosser, G. Natoli, J. P. Saeij, J. L. Schultze, K. A. Shirey, A. Sica, J. Suttles, I. Udalova, J. A. van Ginderachter, S. N. Vogel and T. A. Wynn (2014). "Macrophage activation and polarization: nomenclature and experimental guidelines." *Immunity* 41(1): 14-20.

Nahrendorf, M. and F. K. Swirski (2013). "Monocyte and macrophage heterogeneity in the heart." *Circ Res* 112 (12): 1624-1633.

Nahrendorf, M. and F. K. Swirski (2016). "Abandoning M1/M2 for a Network Model of Macrophage Function." *Circ Res* 119(3): 414-417.

Nahrendorf, M., F. K. Swirski, E. Aikawa, L. Stangenberg, T. Wurdinger, J. L. Figueiredo, P. Libby, R. Weissleder and M. J. Pittet (2007). "The healing myocardium sequentially mobilizes two monocyte subsets with divergent and complementary functions." *J Exp Med* 204(12): 3037-3047.

Nathan, C. and A. Ding (2010). "Nonresolving inflammation." *Cell* 140(6): 871-882.

Ngkelo, A., A. Richart, J. A. Kirk, P. Bonnin, J. Vilar, M. Lemitre, P. Marck, M. Branchereau, S. Le Gall, N. Renault, C. Guerin, M. J. Ranek, A. Kervadec, L. Danelli, G. Gautier, U. Blank, P. Launay, E. Camerer, P. Bruneval, P. Menasche, C. Heymes, E. Luche, L. Casteilla, B. Cousin, H. R. Rodewald, D. A. Kass and J. S. Silvestre (2016). "Mast cells regulate myofilament calcium sensitization and heart function after myocardial infarction." *J Exp Med* 213(7): 1353-1374.

Nian, M., P. Lee, N. Khaper and P. Liu (2004). "Inflammatory cytokines and postmyocardial infarction remodeling." *Circ Res* 94(12): 1543-1553.

Oh, Y. K., D. E. Nix and R. M. Straubinger (1995). "Formulation and efficacy of liposome-encapsulated antibiotics for therapy of intracellular Mycobacterium avium infection." *Antimicrob Agents Chemother* 39(9): 2104-2111.

Ohara, H., Y. Nakamura, Y. Watanabe, X. Cao, Y. Yamazaki, H. Izumi-Nakaseko, K. Ando, H. Yamazaki, J. Yamazaki, T. Ikeda and A. Sugiyama (2015). "Azithromycin Can Prolong QT Interval and Suppress Ventricular Contraction, but Will Not Induce Torsade de Pointes." *Cardiovasc Toxicol* 15(3): 232-240.

Okada, H., G. Takemura, K. Kosai, Y. Li, T. Takahashi, M. Esaki, K. Yuge, S. Miyata, R. Maruyama, A. Mikami, S. Minatoguchi, T. Fujiwara and H. Fujiwara (2005). "Postinfarction gene therapy against transforming growth factor-beta signal modulates infarct tissue dynamics and attenuates left ventricular remodeling and heart failure."*Circulation* 111(19): 2430-2437.

Ong, S. B., S. Hernandez-Resendiz, G. E. Crespo-Avilan, R. T. Mukhametshina, X. Y. Kwek, H. A. Cabrera-Fuentes and D. J. Hausenloy (2018). "Inflammation following acute myocardial infarction: Multiple players, dynamic roles, and novel therapeutic opportunities." *Pharmacol Ther* 186: 73-87.

Ortega-Gomez, A., M. Perretti and O. Soehnlein (2013). "Resolution of inflammation: an integrated view." *EMBO Mol Med* 5(5): 661-674.

Oyama, J., C. Blais, Jr., X. Liu, M. Pu, L. Kobzik, R. A. Kelly and T. Bourcier (2004). "Reduced myocardial ischemia-reperfusion injury in toll-like receptor 4-deficient mice." *Circulation* 109(6): 784-789.

Panizzi, P., F. K. Swirski, J. L. Figueiredo, P. Waterman, D. E. Sosnovik, E. Aikawa, P. Libby, M. Pittet, R. Weissleder and M. Nahrendorf (2010). "Impaired infarct healing in atherosclerotic mice with Ly-6C(hi) monocytosis." *J Am Coll Cardiol* 55(15): 1629-1638.

Patel, K. D., G. A. Zimmerman, S. M. Prescott, R. P. McEver and T. M. McIntyre (1991). "Oxygen radicals induce human endothelial cells to express GMP-140 and bind neutrophils." *J Cell Biol* 112(4): 749-759.

Pelegrin, P. and A. Surprenant (2009). "Dynamics of macrophage polarization reveal new mechanism to inhibit IL-1beta release through pyrophosphates." *EMBO J* 28(14): 2114-2127.

Perlman, R. L. (2016). "Mouse models of human disease: An evolutionary perspective." *Evol Med Public Health* 2016(1): 170-176.

Pesce, J., M. Kaviratne, T. R. Ramalingam, R. W. Thompson, J. F. Urban, Jr., A. W. Cheever, D. A. Young, M. Collins, M. J. Grusby and T. A. Wynn (2006). "The IL-21 receptor augments Th2 effector function and alternative macrophage activation." *J Clin Invest* 116(7): 2044-2055.

Peters, D. H., H. A. Friedel and D. McTavish (1992). "Azithromycin. A review of its antimicrobial activity, pharmacokinetic properties and clinical efficacy." *Drugs* 44(5): 750-799.

Petrie, T. A., N. S. Strand, C. T. Yang, J. S. Rabinowitz and R. T. Moon (2014). "Macrophages modulate adult zebrafish tail fin regeneration." *Development* 141(13): 2581-2591.

Pfeffer, M. A. (1995). "Left ventricular remodeling after acute myocardial infarction."*Annu Rev Med* 46: 455-466.

Pfeffer, M. A. and E. Braunwald (1990). "Ventricular remodeling after myocardial infarction. Experimental observations and clinical implications." *Circulation* 81(4): 1161-1172.

Pfeffer, M. A., J. M. Pfeffer, M. C. Fishbein, P. J. Fletcher, J. Spadaro, R. A. Kloner and E. Braunwald (1979). "Myocardial infarct size and ventricular function in rats." *Circ Res* 44(4): 503-512.

Pfeffer, M. A., J. M. Pfeffer, C. Steinberg and P. Finn (1985). "Survival after an experimental myocardial infarction: beneficial effects of long-term therapy with captopril." *Circulation* 72(2): 406-412.

Pinckard, R. N., M. S. Olson, P. C. Giclas, R. Terry, J. T. Boyer and R. A. O'Rourke (1975). "Consumption of classical complement components by heart subcellular membranes in vitro and in patients after acute myocardial infarction." *J Clin Invest* 56(3): 740-750.

Pinto, A. R., R. Paolicelli, E. Salimova, J. Gospocic, E. Slonimsky, D. Bilbao-Cortes, J. W. Godwin and N. A. Rosenthal (2012). "An abundant tissue macrophage population in the adult murine heart with a distinct alternatively-activated macrophage profile." *PLoS One* 7(5): e36814.

Porrello, E. R., A. I. Mahmoud, E. Simpson, J. A. Hill, J. A. Richardson, E. N. Olson and H. A. Sadek (2011). "Transient regenerative potential of the neonatal mouse heart." *Science* 331(6020): 1078-1080.

Porrello, E. R., A. I. Mahmoud, E. Simpson, B. A. Johnson, D. Grinsfelder, D. Canseco, P. P. Mammen, B. A. Rothermel, E. N. Olson and H. A. Sadek (2013). "Regulation of neonatal and adult mammalian heart regeneration by the miR-15 family." *Proc Natl Acad Sci U S A* 110(1): 187-192.

Prabhu, S. D. and N. G. Frangogiannis (2016). "The Biological Basis for Cardiac Repair After Myocardial Infarction: From Inflammation to Fibrosis." *Circ Res* 119(1): 91-112.

Protti, A., H. Mongue-Din, K. J. Mylonas, A. Sirker, C. M. Sag, M. M. Swim, L. Maier, G. Sawyer, X. Dong, R. Botnar, J. Salisbury, G. A. Gray and A. M. Shah (2016). "Bone marrow transplantation modulates tissue macrophage phenotype and enhances cardiac recovery after subsequent acute myocardial infarction." *J Mol Cell Cardiol* 90: 120-128.

Proudfoot, A. E., T. M. Handel, Z. Johnson, E. K. Lau, P. LiWang, I. Clark-Lewis, F. Borlat, T. N. Wells and M. H. Kosco-Vilbois (2003). "Glycosaminoglycan binding and oligomerization are essential for the in vivo activity of certain chemokines." *Proc Natl Acad Sci U S A* 100(4): 1885-1890.

Qin, C. X., S. B. Finlayson, A. Al-Sharea, M. Tate, M. J. De Blasio, M. Deo, S. Rosli, D. Prakoso, C. J. Thomas, H. Kiriazis, E. Gould, Y. H. Yang, E. F. Morand, M. Perretti, A. J. Murphy, X. J. Du, X. M. Gao and R. H. Ritchie (2017). "Endogenous Annexin-A1 Regulates Haematopoietic Stem Cell Mobilisation and Inflammatory Response Post Myocardial Infarction in Mice In Vivo." *Sci Rep* 7(1): 16615.

Ramirez, T. A., R. P. Iyer, 0. Ghasemi, E. F. Lopez, D. B. Levin, J. Zhang, R. Zamilpa, Y. M. Chou, Y. F. Jin and M. L. Lindsey (2014). "Aliskiren and valsartan mediate left ventricular remodeling post-myocardial infarction in mice through MMP-9 effects." *J Mol Cell Cardiol* 72: 326-335.

Ramjee, V., D. Li, L. J. Manderfield, F. Liu, K. A. Engleka, H. Aghajanian, C. B. Rodell, W. Lu, V. Ho, T. Wang, L. Li, A. Singh, D. M. Cibi, J. A. Burdick, M. K. Singh, R. Jain and J. A. Epstein (2017). "Epicardial YAP/TAZ orchestrate an immunosuppressive response following myocardial infarction." *J Clin Invest* 127(3): 899-911.

Rapp, R. P. (1998). "Pharmacokinetics and pharmacodynamics of intravenous and oral azithromycin: enhanced tissue activity and minimal drug interactions." *Ann Pharmacother* 32(7-8): 785-793.

Reimer, K. A., C. E. Murry and V. J. Richard (1989). "The role of neutrophils and free radicals in the ischemic-reperfused heart: why the confusion and controversy?" *J Mol Cell Cardiol* 21(12): 1225-1239.

Ribeiro, C. M., H. Hurd, Y. Wu, M. E. Martino, L. Jones, B. Brighton, R. C. Boucher and W. K. O'Neal (2009). "Azithromycin treatment alters gene expression in inflammatory, lipid metabolism, and cell cycle pathways in well-differentiated human airway epithelia." *PLoS One* 4(6): e5806.

Richard, V. J., C. E. Murry, R. B. Jennings and K. A. Reimer (1988). "Therapy to reduce free radicals during early reperfusion does not limit the size of myocardial infarcts caused by 90 minutes of ischemia in dogs." *Circulation* 78(2): 473-480.

Ridker, P. M., B. M. Everett, T. Thuren, J. G. MacFadyen, W. H. Chang, C. Ballantyne, F. Fonseca, J. Nicolau, W. Koenig, S. D. Anker, J. J. P. Kastelein, J. H. Cornel, P. Pais, D. Pella, J. Genest, R. Cifkova, A. Lorenzatti, T. Forster, Z. Kobalava, L. Vida-Simiti, M. Flather, H. Shimokawa, H. Ogawa, M. Dellborg, P. R. F. Rossi, R. P. T. Troquay, P. Libby, R. J. Glynn and C. T. Group (2017). "Antiinflammatory Therapy with Canakinumab for Atherosclerotic Disease." *N Engl J Med* 377(12): 1119-1131.

Robbins, C. S., A. Chudnovskiy, P. J. Rauch, J. L. Figueiredo, Y. Iwamoto, R. Gorbatov, M. Etzrodt, G. F. Weber, T. Ueno, N. van Rooij en, M. J. Mulligan-Kehoe, P. Libby, M. Nahrendorf, M. J. Pittet, R. Weissleder and F. K. Swirski (2012). "Extramedullary hematopoiesis generates Ly-6C(high) monocytes that infiltrate atherosclerotic lesions." *Circulation* 125(2): 364-374.

Romson, J. L., B. G. Hook, S. L. Kunkel, G. D. Abrams, M. A. Schork and B. R. Lucchesi (1983). "Reduction of the extent of ischemic myocardial injury by neutrophil depletion in the dog." *Circulation* 67(5): 1016-1023.

Romson, J. L., B. G. Hook, V. H. Rigot, M. A. Schork, D. P. Swanson and B. R. Lucchesi (1982). "The effect of ibuprofen on accumulation of indium-111-labeled platelets and leukocytes in experimental myocardial infarction." *Circulation* 66(5): 1002-1011.

Rose, P. G. (2005). "Pegylated liposomal doxorubicin: optimizing the dosing schedule in ovarian cancer." *Oncologist* 10(3): 205-214.

Rubin, B. K. and M. O. Henke (2004). "Immunomodulatory activity and effectiveness of macrolides in chronic airway disease." *Chest* 125(2 Suppl): 70S-78S.

Sager, H. B., M. Hulsmans, K. J. Lavine, M. B. Moreira, T. Heidt, G. Courties, Y. Sun, Y. Iwamoto, B. Tricot, O. F. Khan, J. E. Dahlman, A. Borodovsky, K. Fitzgerald, D. G. Anderson, R. Weissleder, P. Libby, F. K. Swirski and M. Nahrendorf (2016). "Proliferation and Recruitment Contribute to Myocardial Macrophage Expansion in Chronic Heart Failure." *Circ Res* 119(7): 853-864.

Saini, H. K., Y. J. Xu, M. Zhang, P. P. Liu, L. A. Kirshenbaum and N. S. Dhalla (2005). "Role of tumour necrosis factor-alpha and other cytokines in ischemia-reperfusion-induced injury in the heart." *Exp Clin Cardiol* 10(4): 213-222.

Saxena, A., M. Dobaczewski, V. Rai, Z. Hague, W. Chen, N. Li and N. G. Frangogiannis (2014). "Regulatory T cells are recruited in the infarcted mouse myocardium and may modulate fibroblast phenotype and function." *Am J Physiol Heart Circ Physiol* 307(8): H1233-1242.

Schjerning Olsen, A. M., E. L. Fosbol, J. Lindhardsen, F. Folke, M. Charlot, C. Selmer, M. Lamberts, J. Bjerring Olesen, L. Kober, P. R. Hansen, C. Torp-Pedersen and G. H. Gislason (2011). "Duration of treatment with non-steroidal anti-inflammatory drugs and impact on risk of death and recurrent myocardial infarction in patients with prior myocardial infarction: a nationwide cohort study." *Circulation* 123(20): 2226-2235.

Schnoor, M., P. Cullen, J. Lorkowski, K. Stolle, H. Robenek, D. Troyer, J. Rauterberg and S. Lorkowski (2008). "Production of type VI collagen by human macrophages: a new dimension in macrophage functional heterogeneity." *J Immunol* 180(8): 5707-5719.

Schroder, K. and J. Tschopp (2010). "The inflammasomes." *Cell* 140(6): 821-832.

Schulz, C., E. Gomez Perdiguero, L. Chorro, H. Szabo-Rogers, N. Cagnard, K. Kierdorf, M. Prinz, B. Wu, S. E. Jacobsen, J. W. Pollard, J. Frampton, K. J. Liu and F. Geissmann (2012). "A lineage of myeloid cells independent of Myb and hematopoietic stem cells." *Science* 336(6077): 86-90.

Scott, R. C., J. M. Rosano, Z. Ivanov, B. Wang, P. L. Chong, A. C. Issekutz, D. L. Crabbe and M. F. Kiani (2009). "Targeting VEGF-encapsulated immunoliposomes to MI heart improves vascularity and cardiac function." *FASEB J* 23(10): 3361-3367.

Sellak, H., E. Franzini, J. Hakim and C. Pasquier (1994). "Reactive oxygen species rapidly increase endothelial ICAM-1 ability to bind neutrophils without detectable upregulation." *Blood* 83(9): 2669-2677.

Serbina, N. V. and E. G. Pamer (2006). "Monocyte emigration from bone marrow during bacterial infection requires signals mediated by chemokine receptor CCR2." *Nat Immunol* 7(3): 311-317.

Serhan, C. N. and J. Savill (2005). "Resolution of inflammation: the beginning programs the end." *Nat Immunol* 6(12): 1191-1197.

Seropian, I. M., S. Toldo, B. W. Van Tassell and A. Abbate (2014). "Anti-inflammatory strategies for ventricular remodeling following ST-segment elevation acute myocardial infarction." *J Am Coll Cardiol* 63(16): 1593-1603.

Shinkai, M., G. H. Foster and B. K. Rubin (2006). "Macrolide antibiotics modulate ERK phosphorylation and IL-8 and GM-CSF production by human bronchial epithelial cells." *Am J Physiol Lung Cell Mol Physiol* 290(1): L75-85.

Sica, A., K. Matsushima, J. Van Damme, J. M. Wang, N. Polentarutti, E. Dejana, F. Colotta and A. Mantovani (1990). "IL-1 transcriptionally activates the neutrophil chemotactic factor/IL-8 gene in endothelial cells." *Immunology* 69(4): 548-553.

Simpson, P. J., J. C. Fantone, J. K. Mickelson, K. P. Gallagher and B. R. Lucchesi (1988). "Identification of a time window for therapy to reduce experimental canine myocardial injury: suppression of neutrophil activation during 72 hours of reperfusion." *Circ Res* 63(6): 1070-1079.

Simpson, P. J., R. F. Todd, 3rd, J. K. Mickelson, J. C. Fantone, K. P. Gallagher, K. A. Lee, Y. Tamura, M. Cronin and B. R. Lucchesi (1990). "Sustained limitation of myocardial reperfusion injury by a monoclonal antibody that alters leukocyte function." *Circulation* 81(1): 226-237.

Siwik, D. A. and W. S. Colucci (2004). "Regulation of matrix metalloproteinases by cytokines and reactive oxygen/nitrogen species in the myocardium." *Heart Fail Rev* 9(1): 43-51.

Skyschally, A., R. Schulz and G. Heusch (2008). "Pathophysiology of myocardial infarction: protection by ischemic pre- and postconditioning." *Herz* 33(2): 88-100.

Smith, C. W., S. D. Marlin, R. Rothlein, C. Toman and D. C. Anderson (1989). "Cooperative interactions of LFA-1 and Mac-1 with intercellular adhesion molecule-1 in facilitating adherence and transendothelial migration of human neutrophils in vitro." *J Clin Invest* 83(6): 2008-2017.

Smith, C. W., R. Rothlein, B. J. Hughes, M. M. Mariscalco, H. E. Rudloff, F. C. Schmalstieg and D. C. Anderson (1988). "Recognition of an endothelial determinant for CD 18-dependent human neutrophil adherence and transendothelial migration." *J Clin Invest* 82(5): 1746-1756.

Snyderman, R. and E. J. Goetzl (1981). "Molecular and cellular mechanisms of leukocyte chemotaxis." *Science* 213(4510): 830-837.

Soehnlein, O. and L. Lindbom (2010). "Phagocyte partnership during the onset and resolution of inflammation." *Nat Rev Immunol* 10(6): 427-439.

Soehnlein, O., A. Zernecke, E. E. Eriksson, A. G. Rothfuchs, C. T. Pham, H. Herwald, K. Bidzhekov, M. E. Rottenberg, C. Weber and L. Lindbom (2008). "Neutrophil secretion products pave the way for inflammatory monocytes." *Blood* 112(4): 1461-1471.

Song, E., N. Ouyang, M. Horbelt, B. Antus, M. Wang and M. S. Exton (2000). "Influence of alternatively and classically activated macrophages on fibrogenic activities of human fibroblasts." *Cell Immunol* 204(1): 19-28.

Souders, C. A., S. L. Bowers and T. A. Baudino (2009). "Cardiac fibroblast: the renaissance cell." *Circ Res* 105(12): 1164-1176.

Spatz, E. S., A. L. Beckman, Y. Wang, N. R. Desai and H. M. Krumholz (2016). "Geographic Variation in Trends and Disparities in Acute Myocardial Infarction Hospitalization and Mortality by Income Levels, 1999-2013." *JAMA Cardiol* 1(3): 255-265.

Stancovski, I. and D. Baltimore (1997). "NF-kappaB activation: the I kappaB kinase revealed?" *Cell* 91(3): 299-302.

Strieter, R. M., S. L. Kunkel, H. J. Showell and R. M. Marks (1988). "Monokine-induced gene expression of a human endothelial cell-derived neutrophil chemotactic factor." *Biochem Biophys Res Commun* 156(3): 1340-1345.

Sunderkotter, C., M. Goebeler, K. Schulze-Osthoff, R. Bhardwaj and C. Sorg (1991). "Macrophage-derived angiogenesis factors." *Pharmacol Ther* 51(2): 195-216.

Swirski, F. K. and M. Nahrendorf (2013). "Macrophage-stem cell crosstalk after myocardial infarction." *J Am Coll Cardiol* 62(20): 1902-1904.

Swirski, F. K., M. Nahrendorf, M. Etzrodt, M. Wildgruber, V. Cortez-Retamozo, P. Panizzi, J. L. Figueiredo, R. H. Kohler, A. Chudnovskiy, P. Waterman, E. Aikawa, T. R. Mempel, P. Libby, R. Weissleder and M. J. Pittet (2009). "Identification of splenic reservoir monocytes and their deployment to inflammatory sites." *Science* 325(5940): 612-616.

Tahto, E., R. Jadric, L. Pojskic and E. Kicic (2017). "Neutrophil-to-lymphocyte Ratio and Its Relation with Markers of Inflammation and Myocardial Necrosis in Patients with Acute Coronary Syndrome." *Med Arch* 71(5): 312-315.

Takahama, H., T. Minamino, H. Asanuma, M. Fujita, T. Asai, M. Wakeno, H. Sasaki, H. Kikuchi, K. Hashimoto, N. Oku, M. Asakura, J. Kim, S. Takashima, K. Komamura, M. Sugimachi, N. Mochizuki and M. Kitakaze (2009). "Prolonged targeting of ischemic/reperfused myocardium by liposomal adenosine augments cardioprotection in rats." *J Am Coll Cardiol* 53(8): 709-717.

Tamoutounour, S., M. Guilliams, F. Montanana Sanchis, H. Liu, D. Terhorst, C. Malosse, E. Pollet, L. Ardouin, H. Luche, C. Sanchez, M. Dalod, B. Malissen and S. Henri (2013). "Origins and functional specialization of macrophages and of conventional and monocyte-derived dendritic cells in mouse skin." *Immunity* 39(5): 925-938.

Tanaka, S., K. Kitagawa, S. Sugiura, E. Matsuoka-Omura, T. Sasaki, Y. Yagita and M. Hori (2004). "Infiltrating macrophages as in vivo targets for intravenous gene delivery in cerebral infarction." *Stroke* 35(8): 1968-1973.

ter Horst, E. N., N. Hakimzadeh, A. M. van der Laan, P. A. Krijnen, H. W. Niessen and J. J. Piek (2015). "Modulators of Macrophage Polarization Influence Healing of the Infarcted Myocardium." *Int J Mol Sci* 16(12): 29583-29591.

Thelen, M., P. Peveri, P. Kernen, V. von Tscharner, A. Walz and M. Baggiolini (1988). "Mechanism of neutrophil activation by NAF, a novel monocyte-derived peptide agonist." *FASEB J* 2(11): 2702-2706.

Timmers, L., G. Pasterkamp, V. C. de Hoog, F. Arslan, Y. Appelman and D. P. de Kleijn (2012). "The innate immune response in reperfused myocardium." *Cardiovasc Res* 94(2): 276-283.

Tsai, W. C., M. L. Rodriguez, K. S. Young, J. C. Deng, V. J. Thannickal, K. Tateda, M. B. Hershenson and T. J.

Standiford (2004). "Azithromycin blocks neutrophil recruitment in *Pseudomonas* endobronchial infection." *Am J Respir Crit Care Med* 170(12): 1331-1339.

Tsujioka, H., T. Imanishi, H. Ikejima, A. Kuroi, S. Takarada, T. Tanimoto, H. Kitabata, K. Okochi, Y. Arita, K. Ishibashi, K. Komukai, H. Kataiwa, N. Nakamura, K. Hirata, A. Tanaka and T. Akasaka (2009). "Impact of heterogeneity of human peripheral blood monocyte subsets on myocardial salvage in patients with primary acute myocardial infarction." *J Am Coll Cardiol* 54(2): 130-138.

Ungureanu, V. (2010). "[Macrolides, lincosamides, streptogramines (MLS): mechanisms of action and resistance]." *Bacteriol Virusol Parazitol Epidemiol* 55(2): 131-138.

Uraizee, A., K. A. Reimer, C. E. Murry and R. B. Jennings (1987). "Failure of superoxide dismutase to limit size of myocardial infarction after 40 minutes of ischemia and 4 days of reperfusion in dogs." *Circulation* 75(6): 1237-1248.

Vakeva, A. P., A. Agah, S. A. Rollins, L. A. Matis, L. Li and G. L. Stahl (1998). "Myocardial infarction and apoptosis after myocardial ischemia and reperfusion: role of the terminal complement components and inhibition by anti-05 therapy." *Circulation* 97(22): 2259-2267.

van Amerongen, M. J., M. C. Harmsen, N. van Rooijen, A. H. Petersen and M. J. van Luyn (2007). "Macrophage depletion impairs wound healing and increases left ventricular remodeling after myocardial injury in mice." *Am J Pathol* 170(3): 818-829.

Van der Borght, K., C. L. Scott, V. Nindl, A. Bouche, L. Martens, D. Sichien, J. Van Moorleghem, M. Vanheerswynghels, S. De Prijck, Y. Saeys, B. Ludewig, T. Gillebert, M. Guilliams, P. Carmeliet and B. N. Lambrecht (2017). "Myocardial Infarction Primes Autoreactive T Cells through Activation of Dendritic Cells." *Cell Rep* 18(12): 3005-3017.

van der Laan, A. M., M. Nahrendorf and J. J. Piek (2012). "Healing and adverse remodelling after acute myocardial infarction: role of the cellular immune response." *Heart* 98(18): 1384-1390.

Varano, G. P., V. Parisi, A. Adornetto, F. Cavaliere, D. Amantea, C. Nucci, M. T. Corasaniti, L. A. Morrone, G. Bagetta and R. Russo (2017). "Post-ischemic treatment with azithromycin protects ganglion cells against retinal ischemia/reperfusion injury in the rat." *Mol Vis* 23: 911-921.

Varda-Bloom, N., J. Leor, D. G. Ohad, Y. Hasin, M. Amar, R. Fixler, A. Battler, M. Eldar and D. Hasin (2000). "Cytotoxic T lymphocytes are activated following myocardial infarction and can recognize and kill healthy myocytes in vitro." *J Mol Cell Cardiol* 32(12): 2141-2149.

Verdouw, P. D., M. A. van den Doel, S. de Zeeuw and D. J. Duncker (1998). "Animal models in the study of myocardial ischaemia and ischaemic syndromes." *Cardiovasc Res* 39(1): 121-135.

von Hundelshausen, P. and C. Weber (2007). "Platelets as immune cells: bridging inflammation and cardiovascular disease." *Circ Res* 100(1): 27-40.

Wan, E., X. Y. Yeap, S. Dehn, R. Terry, M. Novak, S. Zhang, S. Iwata, X. Han, S. Homma, K. Drosatos, J. Lomasney, D. M. Engman, S. D. Miller, D. E. Vaughan, J. P. Morrow, R. Kishore and E. B. Thorp (2013). "Enhanced efferocytosis of apoptotic cardiomyocytes through myeloid-epithelial-reproductive tyrosine kinase links acute inflammation resolution to cardiac repair after infarction." *Circ Res* 113(8): 1004-1012.

Wang, P., H. Chen, H. Qin, S. Sankarapandi, M. W. Becher, P. C. Wong and J. L. Zweier (1998). "Overexpression of human copper, zinc-superoxide dismutase (SOD1) prevents postischemic injury." *Proc Natl Acad Sci U S A* 95(8): 4556-4560.

Weirather, J., U. D. Hofmann, N. Beyersdorf, G. C. Ramos, B. Vogel, A. Frey, G. Ertl, T. Kerkau and S. Frantz (2014). "Foxp3+ CD4+ T cells improve healing after myocardial infarction by modulating monocyte/macrophage differentiation." *Circ Res* 115(1): 55-67.

Weisman, H. F., T. Bartow, M. K. Leppo, H. C. Marsh, Jr., G. R. Carson, M. F. Concino, M. P. Boyle, K. H. Roux, M. L. Weisfeldt and D. T. Fearon (1990). "Soluble human complement receptor type 1: in vivo inhibitor of complement suppressing post-ischemic myocardial inflammation and necrosis." *Science* 249(4965): 146-151.

Weisser, S. B., N. van Rooij en and L. M. Sly (2012). "Depletion and reconstitution of macrophages in mice." *J Vis Exp* (66): 4105.

White, H. D. and D. P. Chew (2008). "Acute myocardial infarction." *Lancet* 372(9638): 570-584.

Writing Group, M., D. Mozaffarian, E. J. Benjamin, A. S. Go, D. K. Arnett, M. J. Blaha, M. Cushman, S. R. Das, S. de Ferranti, J. P. Despres, H. J. Fullerton, V. J. Howard, M. D. Huffman, C. R. Isasi, M. C. Jimenez, S. E. Judd, B. M. Kissela, J. H. Lichtman, L. D. Lisabeth, S. Liu, R. H. Mackey, D. J. Magid, D. K. McGuire, E. R. Mohler, 3rd, C. S. Moy, P. Muntner, M. E. Mussolino, K. Nasir, R. W. Neumar, G. Nichol, L. Palaniappan, D. K. Pandey, M. J. Reeves, C. J. Rodriguez, W. Rosamond, P. D. Sorlie, J. Stein, A. Towfighi, T. N. Turan, S. S. Virani, D. Woo, R. W. Yeh, M. B. Turner, C. American Heart Association Statistics and S. Stroke Statistics (2016). "Heart Disease and Stroke Statistics-2016 Update: A Report From the American Heart Association." *Circulation* 133(4): e38-360.

Xia, Y., V. L. Dawson, T. M. Dawson, S. H. Snyder and J. L. Zweier (1996). "Nitric oxide synthase generates superoxide and nitric oxide in arginine-depleted cells leading to peroxynitrite-mediated cellular injury." *Proc Natl Acad Sci U S A* 93(13): 6770-6774.

Xue, J., S. V. Schmidt, J. Sander, A. Draffehn, W. Krebs, I. Quester, D. De Nardo, T. D. Gohel, M. Emde, L. Schmidleithner, H. Ganesan, A. Nino-Castro, M. R. Mallmann, L. Labzin, H. Theis, M. Kraut, M. Beyer, E. Latz, T. C. Freeman, T. Ulas and J. L. Schultze (2014). "Transcriptome-based network analysis reveals a spectrum model of human macrophage activation." *Immunity* 40(2): 274-288.

Yamaryo, T., K. Oishi, H. Yoshimine, Y. Tsuchihashi, K. Matsushima and T. Nagatake (2003). "Fourteen-member macrolides promote the phosphatidylserine receptor-dependent phagocytosis of apoptotic neutrophils by alveolar macrophages." *Antimicrob Agents Chemother* 47(1): 48-53.

Yan, X., A. Anzai, Y. Katsumata, T. Matsuhashi, K. Ito, J. Endo, T. Yamamoto, A. Takeshima, K. Shinmura, W. Shen, K. Fukuda and M. Sano (2013). "Temporal dynamics of cardiac immune cell accumulation following acute myocardial infarction." *J Mol Cell Cardiol* 62: 24-35.

Yang, Z., B. Zingarelli and C. Szabo (2000). "Crucial role of endogenous interleukin-10 production in myocardial ischemia/reperfusion injury." *Circulation* 101(9): 1019-1026.

Yasojima, K., K. S. Kilgore, R. A. Washington, B. R. Lucchesi and P. L. McGeer (1998). "Complement gene expression by rabbit heart: upregulation by ischemia and reperfusion." *Circ Res* 82(11): 1224-1230.

Yellon, D. M. and D. J. Hausenloy (2007). "Myocardial reperfusion injury." *N Engl J Med* 357(11): 1121-1135.

Zarogoulidis, P., N. Papanas, I. Kioumis, E. Chatzaki, E. Maltezos and K. Zarogoulidis (2012). "Macrolides: from in vitro anti-inflammatory and immunomodulatory properties to clinical practice in respiratory diseases." *Eur J Clin Pharmacol* 68(5): 479-503.

Zhang, B., W. M. Bailey, T. J. Kopper, M. B. Orr, D. J. Feola and J. C. Gensel (2015). "Azithromycin drives alternative macrophage activation and improves recovery and tissue sparing in contusion spinal cord injury." *J Neuroinflammation* 12: 218.

Zigmond, E., C. Varol, J. Farache, E. Elmaliah, A. T. Satpathy, G. Friedlander, M. Mack, N. Shpigel, I. G. Boneca, K. M. Murphy, G. Shakhar, Z. Halpern and S. Jung (2012). "Ly6C hi monocytes in the inflamed colon give rise to proinflammatory effector cells and migratory antigen-presenting cells." *Immunity* 37(6): 1076-1090.

Zimmermann, P., V. C. Ziesenitz, N. Curtis and N. Ritz (2018). "The Immunomodulatory Effects of Macrolides-A Systematic Review of the Underlying Mechanisms." *Front Immunol* 9: 302.

Zlatanova, I., C. Pinto and J. S. Silvestre (2016). "Immune Modulation of Cardiac Repair and Regeneration: The Art of Mending Broken Hearts." *Front Cardiovasc Med* 3: 40.

Zouggari, Y., H. Ait-Oufella, P. Bonnin, T. Simon, A. P. Sage, C. Guerin, J. Vilar, G. Caligiuri, D. Tsiantoulas, L. Laurans, E. Dumeau, S. Kotti, P. Bruneval, I. F. Charo, C. J. Binder, N. Danchin, A. Tedgui, T. F. Tedder, J. S. Silvestre and Z. Mallat (2013). "B lymphocytes trigger monocyte mobilization and impair heart function after acute myocardial infarction." *Nat Med* 19(10): 1273-1280.

Zweier, J. L. (1988). "Measurement of superoxide-derived free radicals in the reperfused heart. Evidence for a free radical mechanism of reperfusion injury." *J Biol Chem* 263(3): 1353-1357.

Zymek, P., M. Bujak, K. Chatila, A. Cieslak, G. Thakker, M. L. Entman and N. G. Frangogiannis (2006). "The role of platelet-derived growth factor signaling in healing myocardial infarcts." *J Am Coll Cardiol* 48(11): 2315-2323.

Zymek, P., D. Y. Nah, M. Bujak, G. Ren, A. Koerting, T. Leucker, P. Huebener, G. Taffet, M. Entman and N. G. Frangogiannis (2007). "Interleukin-10 is not a critical regulator of infarct healing and left ventricular remodeling." *Cardiovasc Res* 74(2): 313-322.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

What is claimed is:

1. A method of treating a subject following myocardial infarction, the method comprising:
   administering a pharmaceutically effective amount of a negatively charged non-PEGylated liposome to the subject;
   wherein the non-PEGylated liposome comprises liposomal azithromycin; and
   wherein administering the negatively charged non-PEGylated liposome repolarizes macrophages towards an anti-inflammatory activation state, reducing the ratio of pro-/anti-inflammatory macrophages.

2. The method of claim 1, wherein the liposomal azithromycin includes azithromycin encapsulated in a liposome.

3. The method of claim 1, wherein the azithromycin is included at between 10 and 30 mol % based upon phospholipid content.

4. The method of claim 1, wherein administering the non-PEGylated liposome reduces susceptibility to chronic scar enlargement.

5. The method of claim 1, wherein administering the non-PEGylated liposome decreases inflammatory change in the heart.

6. The method of claim 1, wherein administering the non-PEGylated liposome reduces the ratio without affecting total macrophage count.

7. The method of claim 6, wherein administering the non-PEGylated liposome decreases pro-inflammatory macrophages.

8. The method of claim 7, wherein the pro-inflammatory macrophages include $CD45^+/Ly6G^-/F4-80^+/CD11c^+$.

9. The method of claim 6, wherein administering the non-PEGylated liposome increases reparative macrophages.

10. The method of claim 9, wherein the reparative macrophages include $CD45+/Ly6G^-/F4-80^+/CD11c^-/CD206^+$.

* * * * *